US012774441B2

(12) United States Patent
Veraitch et al.

(10) Patent No.: US 12,774,441 B2
(45) Date of Patent: Oct. 27, 2026

(54) APPARATUS FOR, AND A METHOD OF, PROCESSING CELLS

(71) Applicant: Oribiotech LTD, London (GB)

(72) Inventors: Farlan Veraitch, London (GB); William Raimes, London (GB); Gary Kipling, London (GB); Adam Hiles, Berkhamsted (GB); Philip Wood, Uttlesford (GB); Simon Collings, Datchet (GB); Nicholas Brown, Datchet (GB); Luke Williams, Datchet (GB); Stephen Knowles, Datchet (GB); George Sydney McLean, London (GB)

(73) Assignee: Oribiotech LTD, London (GB)

( * ) Notice: Subject to any disclaimer, the term of this patent is extended or adjusted under 35 U.S.C. 154(b) by 916 days.

(21) Appl. No.: 17/758,686

(22) PCT Filed: Jan. 12, 2021

(86) PCT No.: PCT/GB2021/050065
§ 371 (c)(1),
(2) Date: Jul. 12, 2022

(87) PCT Pub. No.: WO2021/144560
PCT Pub. Date: Jul. 22, 2021

(65) Prior Publication Data
US 2024/0228933 A1 Jul. 11, 2024

(30) Foreign Application Priority Data
Jan. 13, 2020 (GB) ..................................... 2000481

(51) Int. Cl.
*C12M 3/04* (2006.01)
*C12M 1/34* (2006.01)
*C12M 3/00* (2006.01)

(52) U.S. Cl.
CPC ............ *C12M 27/10* (2013.01); *C12M 23/46* (2013.01); *C12M 41/00* (2013.01)

(58) Field of Classification Search
None
See application file for complete search history.

(56) References Cited

U.S. PATENT DOCUMENTS 6,544,788 B2 4/2003 Singh
2015/0252317 A1 9/2015 Ipkens et al.
(Continued)

FOREIGN PATENT DOCUMENTS

EP 0968760 A1 * 1/2000 .............. B01F 31/55
EP 2020433 A2 2/2009
(Continued)

OTHER PUBLICATIONS

International Search Report for International Application No. PCT/GN2021/050065, mailed Apr. 9, 2021, 3 pages.
(Continued)

*Primary Examiner* — William H. Beisner
(74) *Attorney, Agent, or Firm* — TraskBritt

(57) ABSTRACT

There is provided an apparatus for use in cell processing comprising: a holding element arranged to receive a top section of a container within a first plane; a moveable plate, spaced apart from the holding element, arranged to operably engage a base section of a container, the moveable plate defining a second plane substantially parallel to the first plane; and an actuation mechanism operably coupled to the moveable plate to rotate the moveable plate about at least one axis within the second plane, thereby reducing a distance between at least a portion of the second plane and the first plane. There is also provided a method of processing cells.

29 Claims, 42 Drawing Sheets

(56) References Cited

U.S. PATENT DOCUMENTS

| | | | |
|---|---|---|---|
| 2016/0108352 A1 | 4/2016 | Zimmermann et al. |
| 2017/0313967 A1 | 11/2017 | Andersson et al. |
| 2019/0143284 A1 | 5/2019 | Lee et al. |
| 2019/0241851 A1 | 8/2019 | Valat et al. |

FOREIGN PATENT DOCUMENTS

| | | | | | |
|---|---|---|---|---|---|
| EP | 3115450 | A1 | | 1/2017 | |
| JP | 59016532 | A | * | 1/1984 | ............ A61M 1/025 |
| JP | 03-007575 | A | | 1/1991 | |
| JP | H037575 | | * | 1/1991 | .............. C12M 3/00 |
| JP | 3152029 | U | | 6/2009 | |
| JP | 2017-195857 | A | | 11/2017 | |
| JP | 2018-019631 | A | | 2/2018 | |
| KR | 10-2014-0134436 | A | | 11/2014 | |
| WO | 00/53303 | A1 | | 9/2000 | |
| WO | 00/66706 | A1 | | 11/2000 | |
| WO | 2016/185221 | A1 | | 11/2016 | |
| WO | 2017/090757 | A1 | | 6/2017 | |
| WO | 2018/087558 | A1 | | 5/2018 | |
| WO | 2018/229740 | A2 | | 12/2018 | |
| WO | 2019/077003 | A1 | | 4/2019 | |
| WO | 2020/141325 | A1 | | 7/2020 | |

OTHER PUBLICATIONS

International Written Opinion for International Application No. PCT/GN2021/050065, mailed Apr. 9, 2021, 7 pages.

Japanese Notice of Reasons for Refusal for Japanese Application No. 2022-542746, dated Jan. 28, 2025, 10 pages with English translation.

United Kingdom Patent Examination Report for United Kingdom Patent Application No. GB2000481.8, dated Dec. 1, 2021, 4 pages.

United Kingdom Search Report for United Kingdom Patent Application No. GB2000481.8, dated Jun. 7, 2021, 4 pages.

Chinese First Office Action for Chinese Application No. 202180020800.8, dated Oct. 16, 2025, 16 pages with English translation.

Australian Patent Examination Report No. 2 for Australian Application No. 2021208672, dated Dec. 22, 2025, 6 pages.

* cited by examiner (a)

(b)

(c)

APPARATUS FOR, AND A METHOD OF, PROCESSING CELLS

CROSS-REFERENCE TO RELATED APPLICATIONS

This application is a national phase entry under 35 U.S.C. § 371 of International Patent Application PCT/GB2021/050065, filed Jan. 12, 2021, designating the United States of America and published as International Patent Publication WO 2021/144560 A1 on Jul. 22, 2021, which claims the benefit under Article 8 of the Patent Cooperation Treaty to United Kingdom Patent Application Serial No. 2000481.8, filed Jan. 13, 2020.

TECHNICAL FIELD

The disclosure relates to an apparatus for use in performing one or more unit operations in cell processing. Additionally, the disclosure relates to a method of processing cells.

BACKGROUND

There may be any number of unit operations within a cell processing method. Such unit operations vary based upon the cells and the media, amongst other variables. Some cell processing methods may include cell and/or gene therapy manufacture, biofuel production, small molecule production, screening and process development, amongst others.

For example, there may be a need for an algae bioreactor for producing a biofuel therein, an apparatus for carrying out one or more operations in cell and/or gene therapy manufacture, an apparatus for producing small molecules from *E. coli*, an apparatus for deriving primary cells from solid biopsies and single organoid culture, and an apparatus for use in screening and process development.

In one particular non-limiting example, there may be a need for an apparatus for use in performing one or more unit operations in cell and/or gene therapy manufacture. In such examples, cell and gene therapy manufacturing processes are often complex and include manual or semi-automated steps across several devices. Equipment systems used in various steps, that is in several unit operations, of cell-based therapeutic products (CTP) manufacturing may include devices for cell collection, cell isolation, cell selection, cell expansion, cell washing and volume reduction, cell storage and cell transportation. The unit operations can vary immensely based on the manufacturing model, for example, autologous verses allogenic, cell type, intended purpose, amongst other factors. Additionally, cells are "living" entities sensitive to even the simplest manipulations, such as different environments in a cell transferring procedure. The role of cell manufacturing equipment in ensuring scalability and reproducibility is an important factor for cell and/or gene therapy manufacturing.

Moreover, cell-based therapeutic products have gained significant momentum, thus there is an ever increasing need for improved cell manufacturing equipment for various cell manufacturing procedures, for example, but not limited to cell enrichment, generation of chimeric antigen receipt (CAR) T cells, and various cell manufacturing processes such as collection, purification, gene modification, incubation, recovery, washing, infusion into a patient, and freezing.

The culture of processing of cells typically requires the use of a device to hold the cells, for example, in an appropriate culture medium, when culturing the cells. The known devices include shaker flasks, roller bottles, T-flasks and bags. One example of a known device 10, having a bag 14, is shown in FIGS. 1(*a*) and 1(*b*). In this known device 10, there is provided a platform 12 on which the bag 14, for example, a flexible bag, is placed, the bag 14 providing a disposable chamber for the culturing of cells therein. The flexible bag 14 typically includes a series of inlets and outlets, in the form of tubes, to allow for passage of media 16 into the bag 14. The platform 12 is provided upon a baseplate 20 having a pivot point 18 about which the platform 12, and thus the flexible bag 14, can rotate, or rock.

The platform 12 may be rocked about the pivot point 18 through an appropriate angle by virtue of actuators (not shown). The rocking of the platform 12 provides a wave agitation and bubble-free aeration system within the bag 14. Thus, the use of mechanical mixers, which impart high sheer forces onto the media 16, is avoided.

However, chief amongst the problems of such known devices are the requirement for the transfer of cells without contamination when passaging, or processing subsequently, and also the sterile addition of supplements, factors, media or the like. Moreover, such known devices require a substantive amount of manual intervention, especially when adding or removing media to or from the bag, and thus are labor-intensive, prone to human errors when handling, and also have increased operational costs. Furthermore, multiple pieces of equipment are typically required to provide all of the necessary functions for carrying out the cell and/or gene therapy manufacturing process.

Thus, there is a need for cell processing devices, for example, multistep cell processors, which permit such processing and avoid the prerequisite of constant transfer of cells between different devices. Moreover, it would be advantageous if scale-up of cells in culture could be achieved without transferring cells into a larger, or another, device. Furthermore, a single, simple, piece of apparatus having lower operational costs whilst maintaining the advantages associated with the devices would be beneficial.

Drawbacks have been overcome by providing a cell culture container and an apparatus as described in earlier applications (PCT/GB2016/051451, PCT/GB2017/053389 and PCT/GB2020/050007).

FIGS. 2(*a*) and 2(*b*) illustrate the earlier apparatus 50, as described in PCT/GB2020/050007. However, a number of areas of continued improvement of such devices have been identified, which are described herein.

Firstly, it has identified that, at larger volumes of culture media, and thus when using larger containers, an actuator 52 of the apparatus 50 has a tendency to bend, in use. Thus, the base unit 50 requires routine maintenance, which can be costly. In some examples, a support 56 may be provided, however this increases the weight and manufacturing cost of such an apparatus 50. Moreover, as the actuator 52 starts to bend, in use, the compression of a cell culture container can be compromised, thus reducing the efficiency of the cell and/or gene therapy manufacturing process.

Secondly, the actuator 52 of the apparatus 50 is not suitable for mixing media within a container in which the actuator 52 acts upon. In particular, the actuator 52 moves slowly to provide a compression of a container such that media may be removed, sampled or the like. That is, the actuator 52 cannot move at a rate needed to mix the media within the container held thereon. Nor does the actuator 52 provide any other type of mixing, for example, rocking and/or swirling mixing, which is particularly required where media and/or cells are not in contact with a whole fold of the container (see FIGS. 2(*c*) and 2(*d*) for such containers).

Thirdly, as illustrated in FIGS. 2(*c*) and 2(*d*), the previous apparatus may inadequately mix cell processing media in such an arrangement. FIG. 2(*c*) illustrates media 62 within a cell culture container 60 having a portion of the media 64 settled at the base of the cell culture container 60. Although the base unit 50 provides a rotational mechanism 54 for rotating the cell culture container 60 about a central axis in use, such a rotation has to be accurate, and thus slow, as auxiliary containers, positioned above the cell culture container 60, are positioned so that they can dispense media 62 into the cell culture container 60. Thus, as shown in FIG. 2(*d*), after rotation of the cell culture container 60, a portion of the media 64 may remain settled at the base of the cell culture container 60. This is owing to the fact that the cell culture container 60 is placed centrally below the auxiliary containers, coaxial with a central longitudinal axis of rotation. Thus, even at high rotational speeds, the cell culture container 60 only experiences a minimal agitative environment, which is insufficient to ensure homogeneity within the cell culture container 60, as shown in FIG. 2(*d*). Thus, the rotational mechanism 54 of the prior art is unsuitable for adequately agitating the reaction media 62 within the cell culture container 60.

Therefore, there is a need for an apparatus in which several processes in the cell and/or gene therapy manufacturing process can be operated, and in which a container can be adequately agitated to ensure homogeneity therein.

More particularly, there is a need for an apparatus like that discussed in FIGS. 2(*a*) and 2(*b*) that can also impart mixing, for example, compression, rocking and/or swirling mixing, to media within a container received on part of the apparatus.

Thus, the disclosure aims to obviate or mitigate at least one of the aforementioned problems.

BRIEF SUMMARY

An apparatus, a system and methods of usage thereof.

In one aspect of the disclosure there is provided an apparatus for use in performing one or more unit operations in cell processing comprising:

- a holding element arranged to receive a top section of a container within a first plane;
- a moveable plate, spaced apart from the holding element, arranged to operably engage a base section of a container, the moveable plate defining a second plane substantially parallel to the first plane; and
- an actuation mechanism operably coupled to the moveable plate to rotate the moveable plate about at least one axis within the second plane, thereby reducing a distance between at least a portion of the second plane and the first plane.

A holding element may be any appropriate element or mechanism that is configured and/or arranged to receive a portion, some of, or all of, a top section of a container in use. The holding element receives, and holds, a top section of a received container within a first plane. The first plane may extend substantially horizontally, or perpendicular to the vertical.

A moveable plate may be any appropriate element or mechanism that is configured and/or arranged to engage with a portion, some of, or all of, a base section of a container in use. The moveable plate may act upon a base section of a received container. The moveable plate generally defines a second plane. The second plane is generally parallel to the first plane, particularly prior to actuation of the actuation mechanism. The second plane may extend substantially horizontally, or perpendicular to the vertical.

An actuation mechanism may be operably coupled to the moveable plate such that the actuation mechanism causes the moveable plate to act upon a base section of a received container in use. The actuation mechanism may cause the moveable plate, defining the second plane, to rotate, tilt, pivot or move about one or more axes within the second plane, in use. Thus, a distance between a portion of, some of, most of, or all of, the second plane and a portion of, some of, most of, or all of, the first plane may be reduced. Put another way, a portion of, some of, most of, or all of, the second plane may be caused to move toward the first plane. The first plane may remain stationary in use. The actuation mechanism may act upon any portion, or some of, or most of, or all of, the moveable plate to move the portion of, some of, most of, or all of the moveable plate with respect to the first plane. For example, the actuation mechanism may act upon a discrete portion of the moveable plate. For example, the actuation mechanism may act so that the entirety of the moveable plate is moveable.

The moveable plate is moveable about, or rotatable about, or tiltable about, or the like, any axis within the second plane, that is the plane of the moveable plate. Thus, the moveable plate may be rotatable about a single axis, two axes, three axes, a plurality of axes, an infinite number of axes, within the second plane. The moveable plate may be arranged to rotate, in a first configuration, about a first axis and then, in a second configuration, about a second axis. The first axis and the second axis may be perpendicular or parallel to one another. The moveable plate may be arranged to rotate about a single axis to impart a wave motion, or a rocking motion, to a fluid within a received container in which the moveable plate operably engages. The moveable plate may be arranged to rotate about more than one axis, for example, two perpendicular axes, to impart a swirl motion to a fluid within a received container in which the moveable plate operably engages. The moveable plate may be entirely moveable so as to compress a received container between the moveable plate, i.e., the second plane, and the first plane, i.e., the holding element.

This provides the advantage that a number of unit operations in cell processing can be carried out in a single apparatus. That is, the apparatus may be a multi-step processing apparatus for cell processing. For example, the apparatus may advantageously allow for both static and dynamic cell culturing or processing without having to transfer material between apparatuses or systems. For example, the apparatus may advantageously allow for mixing and/or pumping of material in a received container, and thus negates the need for agitative and/or pumping or tubing equipment. This may reduce the footprint of the apparatus, allow for compact apparatuses and enable stackable multiplexing of devices.

Furthermore, this provides the advantage that a cell processing medium may be agitated in situ. In particular, the present apparatus allows for agitation of a cell processing medium without having a transfer the cell processing medium between devices. Thus, homogeneity can be ensured within a single vessel so that any subsequent operation, for example, sampling, may be performed in situ. Furthermore, the apparatus provided herein allows for agitation in any number of directions, including rotation about axes to provide a wave or a swirling agitation, and including compression along an axis. Thus, the apparatus may provide improved mixing of a cell processing medium in situ.

In certain embodiments, the actuation mechanism is arranged to rotate the moveable plate about an axis within the second plane.

That is, in certain embodiments, the actuation mechanism is arranged to rotate the moveable plate about a single, that is one, axis within the second plane. The single axis may centrally disposed within the second plane such that the moveable plate is rotatable about a central axis of the second plane. The single axis may be disposed off-center within the second plane such that the moveable plate is rotatable about an axis other than a central axis running perpendicularly to the second plane. The single axis may be disposed at a point in which a base section of a container is adjoined to a wall element of a container. The single axis may be disposed at an edge of the moveable plate. Thus, the entirety of the base section may be tilted in one direction.

This provides the advantage that a wave motion may be imparted to a fluid within a container received within the apparatus. A wave motion may thoroughly mix the fluid within the container and provide aeration of the fluid.

In certain embodiments, the actuation mechanism is arranged to rotate the moveable plate about a plurality of axes within the second plane.

This provides the advantage that a plurality of wave motions, along a plurality of different axes, are imparted to a fluid within a container received within the apparatus. The plurality of wave motions ensure thorough mixing of the fluid within the container and provide aeration of the fluid. Moreover, such an apparatus ensures that any volume of fluid within a received container can be adequately mixed.

In certain embodiments, the actuation mechanism is arranged to rotate the moveable plate between 0 degrees and 90 degrees about the or each axis of the second plate.

It may be preferable that the moveable plate is rotatable about an angle of approximately 1 to 5 degrees, most preferably 3.5 degrees.

The moveable plate may be rotatable at any rate, depending on the cell processing operation to be carried out. For example, the moveable plate may be rotatable from 1 to 1000 rocks per minute. For example, the moveable plate may be rotatable from 1 to 100 rocks per minute. It may be preferable that the moveable plate is rotatable at a rate of between 5 and 60 rocks per minute, for example, between 20 and 60 rocks per minute, preferably about 10 and 15 rocks per minute. A rock may be defined as a rotation about an axis in one direction, followed by a subsequent rotation about the axis in the opposing direction.

In certain embodiments, a longitudinal axis, extending perpendicularly to the first plane and the second plane, intersects the second plane at an origin, wherein the actuation mechanism is arranged to pivot the moveable plate about the origin.

This provides the advantage that a swirling motion is imparted to a fluid within a container received within the apparatus. A swirling motion may be beneficial for mixing small, i.e., less than 100 mL, volumes of fluids or liquids. A swirling motion may adequately mix the fluid and provide aeration thereto.

In certain embodiments, the origin is centrally located within the second plane.

That is, in certain embodiments, the origin is centrally disposed within the second plane. Put another way, the longitudinal axis is a central longitudinal axis intersecting the second plane at a central origin.

In certain embodiments, the actuation mechanism is arranged to move the moveable plate about a first axis within the second plane, and concurrently about a second axis within the second plane. In some examples, the first axis and the second axis are perpendicular.

In certain embodiments, the actuation mechanism is arranged to rotate the moveable plate about an axis within the second plane between a first configuration, in which the second plane is substantially parallel to the first plane, and a second configuration, in which the second plane forms a predetermined angle with respect to the first plane.

In certain embodiments, the actuation mechanism is further arranged to rotate the moveable plate, in the second configuration, about a longitudinal axis that is perpendicular to the first plane and intersects the second plane at an origin.

In certain embodiments, the origin is centrally located within the second plane. That is, in certain embodiments, the origin is centrally disposed within the second plane. Put another way, the longitudinal axis is a central longitudinal axis intersecting the second plane at a central origin.

In certain embodiments, the actuation mechanism is arranged to rotate the moveable plate about the longitudinal axis at a predetermined angle. In some examples, the predetermined angle is a constant angle. The predetermined angle may be between 0 degrees and 180 degrees, excluding 90 degrees. The predetermined angle generally excludes 0 degrees and 180 degrees.

In certain embodiments, the actuation mechanism is arranged to rotate the moveable plate about the longitudinal axis at a variable angle. That is, in certain embodiments, as the actuation mechanism rotates the moveable plate about the longitudinal axis, the moveable plate is also caused to rotate about an axis, or the axis, within the second plane.

In certain embodiments, the moveable plate is pivotable about the origin such that each point within the second plane, excluding the origin, forms an angle with respect to the longitudinal axis between 0 and 180 degrees, excluding 90 degrees.

It may be preferable that the moveable angle is rotatable about an angle of approximately 1 to 5 degrees and/or approximately 91 degrees to 95 degrees, most preferably 3.5 degrees and/or 93.5 degrees.

The moveable plate may be rotatable at any rate, depending on the cell processing operation to be carried out. The rotation rate of the moveable plate may depend on the cells and/or media to be used. For example, the moveable plate may be rotatable from 1 to 1000 rocks per minute (rpm). For example, the moveable plate may be rotatable from 1 to 100 rocks per minute. It may be preferable that the moveable plate is rotatable at a rate of between 5 and 60 rocks per minute, for example, between 20 and 60 rocks per minute, preferably about 10 and 15 rocks per minute. A rock may be defined as a rotation about an axis in one direction, followed by a subsequent rotation about the axis in the opposing direction.

In particular embodiments, the moveable plate may be rotatable from 1, 5, 10, 15, 20, 25, 30, 35, 40, 45 or 50 rocks per minute to 55, 60, 65, 70, 75, 80, 85, 90, 95 or 100 rocks per minute. Any combination of lower limit and upper limit is contemplated herein.

In particular embodiments, the actuation mechanism is arranged to rotate the moveable plate at any rate discussed above.

In particular embodiments, the angle may be between 1 degree and 179 degrees, 10 degrees and 170 degrees, 20 degrees and 160 degrees, 30 degrees and 150 degrees, 40 degrees and 140 degrees, 50 degrees and 130 degrees, 60 degrees and 120 degrees, 70 degrees and 110 degrees, 80 degrees and 100 degrees, excluding 90 degrees. The lower limit of the angle may be 0 degrees, 1 degree, 10 degrees, 20 degrees, 30 degrees, 40 degrees, 50 degrees, 60 degrees, 70 degrees, 80 degrees, 100 degrees, 110 degrees, 120 degrees, 130 degrees, 140 degrees, 150 degrees, 160 degrees, 170 degrees, 179 degrees, or any integer therebetween, excluding 90 degrees. The upper limit of the angle may be 1 degree, 10 degrees, 20 degrees, 30 degrees, 40 degrees, 50 degrees, 60 degrees, 70 degrees, 80 degrees, 100 degrees, 110 degrees, 120 degrees, 130 degrees, 140 degrees, 150 degrees, 160 degrees, 170 degrees, 179 degrees, 180 degrees, or any integer therebetween. Any combination of lower limit and upper limit is contemplated herein.

In certain embodiments, the actuation mechanism is further arranged to move the moveable plate along a longitudinal axis, substantially perpendicular to the first plane and the second plane, thereby reducing a distance between the second plane and the first plane.

That is, in some embodiments, the actuation mechanism is arranged to reduce the distance between the second plane, or the whole or entirety of the second plane, and the first plane. That is, a distance between each and every point of the second plane and each and every corresponding point of the first plane may be reduced. This may be regarded as a longitudinal axial translation or movement. This may be regarded as a compression motion along the longitudinal axis. This may also be regarded as a linear compression motion.

This provides the advantage that a compressive agitation may be imparted to a cell processing medium within a container. A compressive agitation may be beneficial for mixing large, i.e., 100 mL and greater, volumes of cell processing medium. A compressive agitation may also adequately mix the cell processing medium and provide aeration thereto.

Furthermore, in addition to the abovementioned advantages, a compression motion along the longitudinal axis allows for control of the headspace, that is the space above the cell processing media, in situ. For example, the compression motion allows for removal of material from the container in situ, allows for aeration of the cell processing media in situ, allows for removal of gases from the container in situ, allows for breathing between a container and a secondary container or a filter (i.e., allows fluid transfer from one container to another container or the filter, so as to mediate pressure in the or each container). Therefore, the compression motion may not only agitate the cell processing medium, but may also provide one or more of the other advantages discussed herein.

In certain embodiments, the actuation mechanism is arranged to provide any number of cycles per minute (cpm). One cycle is defined as compression of a received container followed by decompression. Alternatively, one cycle is defined as a longitudinal axial translation of the second plane with respect to the first plane in a first direction, followed by a longitudinal axial translation of the second plane with respect to the first plane in a second direction, opposite the first direction. The distance of the respective longitudinal axial translations in each direction may be substantially equal.

That is, during use, the received container is moved from a first, or original or initial, configuration to a second configuration following compression, and then back to the first, or original or initial, configuration following decompression. The actuation mechanism is arranged to provide any degree of compression. For example, the distance between the first plane to the second plane may be reduced partly, mostly, or fully. Alternatively, the distance between the first plane and the second plane may be increased.

The moveable plate may be longitudinally axially moveable at any rate (i.e., any number of cycles per minute), depending on the cell processing operation to be carried out. The rate may depend on the cells and/or the media to be used. For example, the moveable plate may be moved at a rate from 1 to 100 cycles per minute. In some examples, the movable plate may be moved at a rate from 5 to 80 cycles per minute, preferably 20 to 80 cycles per minute, most preferably 20 to 60 cycles per minute.

In particular embodiments, the moveable plate may be moveable at a rate from 1, 5, 10, 15, 20, 25, 30, 35, 40, 45 or 50 cycles per minute to 55, 60, 65, 70, 75, 80, 85, 90, 95 or 100 cycles per minute. Any combination of lower limit and upper limit is contemplated herein.

In particular embodiments, the moveable plate may be longitudinally axially moveable at a first rate so as to impart turbulence to contents of a received container during use, and may be longitudinally axially moveable at a second rate so as to allow breathing (i.e., to allow fluid, or gas or liquid, transfer from the received container to a secondary container of filter) during use. The first rate may be greater than the second rate. The first and second rates may be measured in cycles per minute as discussed above.

In particular embodiments, the actuation mechanism is arranged to move or translate the moveable plate at any rate discussed above. Thus, the actuation mechanism may be arranged to impart compression and decompression of a received container at any rate discussed above.

In particular embodiments, the actuation mechanism is arranged to provide any appropriate magnitude of movement to a received container. For example, the magnitude of longitudinal axial translation may be measured as a displacement between a first configuration, in which a base of a container is not compressed with respect to the top of a container or in which the second plane has not been longitudinally axially translated with respect to the first plane, and a second configuration, in which a base of a container is at least partially compressed with respect to the top of the container or in which the second plane has at least partially moved, such as a longitudinal axial translation movement, with respect to the first plane. In other words, the magnitude of longitudinal axial translation may be measured as a displacement or displacement amplitude, following compression or longitudinal axial movement, of the second plane with respect to the first plane of the apparatus. The displacement may be dependent on the cell processing operation to be carried out. The displacement may be dependent upon the cells and/or the media to be used. For example, the displacement may be from 1 mm to 100 mm. In some examples, the displacement may be from 5 mm to 50 mm, preferably from 10 to 30 mm, most preferably approximately 20 mm. The displacement may be between a part or portion of the second plane and the first plane (i.e., for rotation of the moveable plate about an axis within the second plane). The displacement may be between the entirety of the second plane and the first plane (i.e., for longitudinal axial movement along the longitudinal axis, such as compression of a received container).

In particular embodiments, the displacement may be from 1 mm, 5 mm, 10 mm, 15 mm, 20 mm, 25 mm, 30 mm, 35 mm, 40 mm, 45 mm or 50 mm to 55 mm, 60 mm, 65 mm, 70 mm, 75 mm, 80 mm, 85 mm, 90 mm, 95 mm or 100 mm. Any combination of lower limit and upper limit is contemplated herein.

In certain embodiments, the holding element comprises a platform operably engageable with a top section of a container, a clamping mechanism operably engageable with a top section of a container, or a sealing plate operably engageable with a top section of a container. The holding element may also include a combination thereof.

In certain embodiments, the holding element comprises a platform, for example, a cell processing platform. In some examples, the cell processing platform comprises at least one inlet fluidly connected to at least one outlet, the, some or each outlet configured for fluid communication with an internal lumen of a container. In some examples, the cell processing platform is arranged to receive one or more auxiliary containers in fluid communication with the or each inlet.

This provides the advantage that a number of unit operations in cell and/or gene therapy manufacture may be carried out in a single apparatus.

In certain embodiments, the holding element comprises a clamping mechanism. The clamping mechanism may be arranged to clamp a top section of a container within the first plane. The clamping mechanism may be arranged to be operably coupled into a housing, a unit or the like. For example, the clamping mechanism may include a flange that is arranged to be received within a recess of a housing. For example, the clamping mechanism may include a clip for coupling a top section of a container to another member, such as a platform or a housing.

In certain embodiments, the holding element comprises a sealing plate. The sealing plate may include, or may form, a lid of a container.

This provides the advantage that medium within a container may be mixed readily, irrespective of its use. That is, this provides the advantage that the apparatus can be used in a broader sense, not only in the field of cell and/or gene therapy manufacture.

In certain embodiments, the actuation mechanism comprises a base plate spaced apart from, and substantially parallel to, the moveable plate, the base plate being operably coupled to the moveable plate.

That is, in some embodiments, the actuation mechanism comprises a base plate. The base plate may be a mounting plate. The base plate may be spaced apart from the moveable plate along an axis. The base plate may be substantially parallel to the moveable plate. The base plate may be substantially parallel to the first plane. The base plate may be operably coupled to the moveable plate by any appropriate mechanism, for example, a linkage.

This provides the advantage that the base plate, and thus the actuation mechanism, may be secured to a surface, for example, a table, an incubator, or a housing unit.

In certain embodiments, the base plate comprises at least one actuator, the or each actuator being operably coupled to, or operably engageable with, the moveable plate.

That is, in some embodiments, the actuation mechanism comprises at least one actuator, formed on, or as part of, the base plate. The or each actuator may be operably coupled to the moveable plate. That is, the or each actuator may be coupled to the base plate at one end and operably coupled to the moveable plate at the other end. In some examples, the or each actuator may be operably engageable with the moveable plate. That is, the or each actuator may be coupled to the base plate at one end, and include a free end that is operable to engage the moveable plate.

This provides the advantage that the actuation mechanism is easier to manufacture.

In certain embodiments, the base plate comprises at least one rail, the or each rail upstanding from the base plate substantially perpendicularly to the base plate, the moveable plate being slidably coupled to the or each rail, and wherein at least one actuator is arranged to slide at least a portion of the moveable plate along the or each rail.

That is, in some embodiments, the base plate comprises one or more rails extending upwardly, from a surface of the base plate and perpendicularly thereto, toward and to the moveable plate. The moveable plate may be connected to the or each rail in a sliding manner. That is, the moveable plate may be slidable along the rail, with respect to the base plate. One or more actuators may be arranged to slide the moveable plate along the or each rail. In some examples, there may be a plurality of rails. In some examples, one or more actuators may be arranged to slide a portion of the moveable plate along each rail. In some examples, one or more actuators may be arranged to slide each portion of the moveable plate along each rail concurrently. In some examples, one or more actuators may be arranged to slide each portion of the moveable plate along each rail non-concurrently.

This provides the advantage that the moveable plate, operably engageable with a base section of a container, can engage the entirety of the base section of the container, in use. In this way, the force applied to the container is spread out across the base section of the container, thus avoiding damage to the container or apparatus, in use.

In certain embodiments, the base plate is operably coupled to the moveable plate by at least one biasing element, the or each biasing element arranged to bias the moveable plate toward the base plate such that the second plane is substantially parallel to the first plane.

That is, in some embodiments, the base plate may include at least one biasing element. The or each biasing element is coupled to the base plate at one end, and operably coupled to the moveable plate at the other end. The or each biasing element may be arranged to bias the moveable plate into a configuration in which the second plane is substantially parallel to the first plane.

In certain embodiments, the or each biasing element comprises a spring, preferably a tension spring.

That is, the or each biasing element may be a spring. The spring may be a tension spring. The spring may be a compression spring. The spring may bias the moveable plate into a configuration in which the second plane is substantially parallel to the first plane.

In some embodiments, the or each biasing element comprises a resiliently deformable portion of the moveable plate, the base plate, or both the moveable plate and the base plate.

In certain embodiments, the base plate further comprises a rotatable support plate arranged to rotate about a longitudinal axis that is substantially perpendicular to the support plate. Further, in such embodiments, the support plate may comprise the or each actuator.

That is, in some embodiments, the actuation mechanism further comprises a support plate. The support plate may be rotatable about an axis. The axis may be a longitudinal axis that is substantially perpendicular to the support plate. The axis may be perpendicular to the first plane, the second plane or both the first plane and the second plane. The support plate may be formed as a portion of the base plate, or as a separate element. The support plate may include one or more actuators.

In some embodiments, the support plate comprises an actuator fixed to the support plate at one end. As the support plate rotates, the actuator can be actuated such that the moveable plate is rotated about an axis within the second plane. The actuator may be always actuated whilst the support plate rotates, such that a swirling motion can be achieved. The actuator may be actuated at set intervals, or manually, so that a portion of the moveable plate is moved, in use.

This provides the advantage that the angle and rate of rotation in which the moveable plate is moved may be readily adjusted.

In certain embodiments, the or each actuator comprises a linear actuator.

That is, in some embodiments, the or each actuator is actuatable in a linear direction. The linear direction may be perpendicular to the first plane, the second plane or both the first plane and the second plane. The linear direction may be coaxial with, or parallel to, a longitudinal axis that is substantially perpendicular to the first plane and the second plane. The linear direction may be toward the first plane, the second plane, or the moveable plate.

In certain embodiments, the moveable plate comprises at least one permanent magnet, and the base plate comprises at least one corresponding electromagnet.

That is, in some embodiments, the moveable plate comprises at least one permanent magnet. The moveable plate may comprise a plurality of permanent magnets. The base plate may comprise at least one corresponding electromagnet. The base plate may comprise a plurality of corresponding electromagnets. In this context, corresponding is used to define that the respective magnets are position such that their magnetic fields are able to interact.

In other examples, the moveable plate comprises at least one electromagnet, and the base plate comprises at least one corresponding electromagnet.

That is, in some embodiments, the moveable plate comprises at least one electromagnet. The moveable plate may comprise a plurality of electromagnets. The base plate may comprise at least one corresponding permanent magnet. The base plate may comprise a plurality of corresponding permanent magnets. In this context, corresponding is used to define that the respective magnets are position such that their magnetic fields are able to interact.

This provides the advantage that the actuation mechanism includes no moving parts.

The or each electromagnet may be controlled by a controller.

In certain embodiments, the or each permanent magnet is distal to a center of the moveable plate, and wherein the or each electromagnet is distal to a center of the base plate.

That is, in some embodiments, the or each permanent magnet is distal, that is away from, the center of the moveable plate. The or each permanent magnet may be disposed on the moveable plate off-center. The or each electromagnet is distal, that is away from, the center of the base plate. The or each electromagnet may be disposed on the base plate off-center.

In other examples, the or each permanent magnet is distal to a center of the moveable plate, and wherein the or each electromagnet is distal to a center of the base plate.

That is, in some embodiments, the or each electromagnet is distal, that is away from, the center of the moveable plate. The or each electromagnet may be disposed on the moveable plate off-center. The or each permanent magnet is distal, that is away from, the center of the base plate. The or each permanent magnet may be disposed on the base plate off-center.

In certain embodiments, the base plate comprises at least one cam member, the or each cam member operably engageable with the moveable plate, wherein the or each cam member is driven by a motor.

That is, in some embodiment, the actuation mechanism comprises at least one cam member formed on, or as part of, the base plate. The or each cam member may be operably engageable with the moveable plate. That is, a cam surface may be engageable with a portion of the moveable plate. In some examples, the or each cam member is driven by a motor. Each cam member may be driven by an independent motor.

This provides the advantage of an improved ease of manufacturing the actuation mechanism.

In certain embodiments, the base plate comprises a central hub, coaxial with, and rotatable about, a longitudinal axis that is perpendicular to the base plate, the central hub including a connecting rod extending radially outwardly from the central hub and terminating in a wheel, the wheel being operably engageable with the moveable plate.

That is, in some embodiments, there may be a hub disposed centrally on, or formed centrally as part of, the base plate. The hub may be coaxial with, and arranged to rotate about, a longitudinal axis extending perpendicularly to the base plate, or the first plane, the second plane or the moveable plate. There may further be a connecting rod, extending along a radius from the hub toward and to a wheel. The wheel may be arranged to engage a portion of the moveable plate. In this way, as the central hub rotates, the wheel rotates about the circumference defined by the connecting rod, such that a swirling motion is effected upon the moveable plate.

This provides the advantage that a symmetrical swirl motion can be achieved. A swirl motion may be used to impart a centrifugal force onto a medium within a container upon the moveable plate, thus allowing material within the medium to be separated based on density. That is, a fractioning process may be achievable through the swirling motion. For example, blood could be processed to separate the materials therein. Furthermore, this provides the advantage that the revolutions per minute of the swirl motion can be readily adjusted.

In certain embodiments, the central hub is caused to rotate about the longitudinal axis by a motor.

That is, in some examples, the central hub may be driven by a motor.

This provides the advantage that, owing to the construction of the base plate, only a single motor is required, thereby improving energy efficiency.

In certain embodiments, the base plate comprises a first linkage operably coupled to the moveable plate, the first linkage being driven by a first motor.

That is, in some examples, the actuation mechanism further comprises a linkage, or a first linkage or a first portion of a linkage. The first linkage extends from a surface of the base plate toward the moveable plate. The first linkage serves to allow the moveable plate to move about at least one axis of the second plane. The first linkage may be driven by a motor, for example, a first motor.

In certain embodiments, the base plate further comprises a second linkage operably coupled to the moveable plate, the second linkage driven by a second motor.

That is, in some examples, the actuation mechanism further comprises a further linkage, or a second linkage or a second portion of a linkage. The second linkage extends from a surface of the base plate toward the moveable plate. The second linkage serves to allow the moveable plate to move about at least one axis of the second plane. The second linkage may allow the moveable plate to rotate about a plurality of axes of the second plane. The second linkage may be driven by a motor, for example, the first motor, or a second motor.

In certain embodiments, the first linkage and the second linkage are operably coupled at opposing edges of the moveable plate.

That is, in some embodiments, the moveable plate includes opposing edges, wherein the first linkage is operably coupled to the moveable plate at one edge, or a first edge, and the second linkage is operably coupled to the moveable plate at the other edge, or a second opposing edge.

In some examples, the first motor and the second motor may be disposed toward opposing edges of the base plate. In some examples, the first motor is adjacent the first linkage. In some examples, the second motor is adjacent the second linkage.

This provides the advantage that a wave agitation can be readily achieved, in addition to a compression motion.

In certain embodiments, the base plate further comprises a third linkage operably coupled to the moveable plate, the third linkage driven by a third motor.

That is, in some embodiments, the base plate may further comprise a further linkage, or a third linkage, or a third portion of a linkage. The third linkage extends from a surface of the base plate toward the moveable plate. The third linkage serves to allow the moveable plate to move about at least one axis of the second plane. The third linkage may allow the moveable plate to move about a plurality of axes of the second plane. The third linkage may be drive by a motor, for example, the first motor, the second motor or a third motor.

This provides the advantage that any agitation motion can be achieved, in combination with a compression motion. Moreover, this provides the advantage that the user can customize agitation motions.

In certain embodiments, there may be provided a linkage having a number of portions thereof. For example, there may be a linkage having a first portion and a second portion, and optionally a third portion. The various portions may be arranged to provide rotation about one, two, three, a plurality of an infinite number of axes within the second plane.

In certain embodiments, the first linkage, the second linkage and the third linkage are operably coupled to the moveable plate in a triangular arrangement.

That is, in some embodiments, the point of attachment of the respective linkages form a triangular arrangement. That is, there may be three points of attachment spaced apart in a triangular arrangement.

This provides the advantage that the moveable plate is provided with additional support.

In certain embodiments, the actuation mechanism comprises a first motor, operably coupled to the moveable plate, configured to rotate the moveable plate about at least one axis within the second plane.

In some examples, the first motor is a reciprocating motor, a brushless motor, a brushed motor, or the like. In some examples, the first motor is arranged to impart a rocking or wave motion to the moveable plate, and thus the received container.

This provides the advantage that a motor may be designated solely for rocking, swirling or wave motions. Thus, the rocking, swirling or wave motions may be more carefully controlled. Furthermore, by having a designated rocking or wave motor, the motors of the apparatus need not be synchronized.

In certain embodiments, the actuation mechanism comprises a second motor, operably coupled to the moveable plate, configured to move the moveable plate along a longitudinal axis, substantially perpendicular to the first plane and/or the second plane, thereby reducing a distance between a portion of the second plane and the first plane. The first and second planes may be substantially parallel throughout the movement. The longitudinal axis may be substantially perpendicular to the first plane and the second plane prior to actuation of the actuation mechanism.

This provides the advantage a motor may be designated solely for longitudinal translation of the moveable plate, and thus compression/decompression of a received container. In particular, the second motor may be designated solely for linear compression mixing of the contents of the container received within the apparatus. Furthermore, by having a designated compression motor, the motors of the apparatus need not be synchronized.

In certain embodiments, the actuation mechanism comprises a third motor, operably coupled to the moveable plate, configured to move the moveable plate along the longitudinal axis, thereby reducing a distance between a portion of the second plane and the first plane.

This provides the advantage another motor may be designated solely for longitudinal translation of the moveable plate, and thus compression/decompression of a received container. Thus, the third motor may work independently of, or in unison with, the second motor to achieve a desired compression/decompression. In particular, the third motor may be designated solely for a breathing or perfusion motion, i.e., a prolonged, slow compression or decompression of the container received therein.

In particular embodiments, the linkage comprises a first linkage portion arranged to operably couple the second motor to the moveable plate.

In particular embodiments, the linkage, such as the first linkage portion, comprises a crank housing, comprising a rotatable crank, slidable along a first longitudinal rail, extending substantially parallel to the longitudinal axis. The first longitudinal rail may be a single rail or a pair of parallel rails. The crank housing may be operably coupled to the first longitudinal rail so as to be slidable along, or slidably connected to, the first longitudinal rail.

Thus, in some embodiments, the crank may be driven by the second motor so as to translate the rotational motion of the motor into an axial translation of the moveable plate. Upon each full rotation of the crank, that is through a rotation of 360 degrees, the crank may cause the moveable plate to axially move along the longitudinal axis in a first direction, toward the holding element, and then axially along the longitudinal axis in a second direction, opposite the first direction, away from the holding element. Thus, each full rotation of the crank may cause a full compression and decompression cycle.

In particular embodiments, the linkage comprises a second linkage portion arranged to operably couple the third motor to the moveable plate.

In particular embodiments, the linkage, such as the second linkage portion, comprises a slider portion, operably coupled to the moveable plate, slidable along a second longitudinal rail. The second longitudinal rail may extend substantially parallel to the first longitudinal rail. The second longitudinal rail may be a single rail or a pair of parallel rails. The slider portion may be operably coupled to the rotatable crank by a connecting rod. The slider portion may be operably coupled to the second longitudinal rail so as to be slidable along, or slidably connected to, the second longitudinal rail.

In particular embodiments, the second motor is operably coupled to the rotatable crank so as to rotate the same and move the slider portion along the second longitudinal rail. Further, in particular embodiments, the third motor is operably connected to the crank housing so as to move the crank housing along the first longitudinal rail.

This arrangement provides the advantage that the second motor may be of unidirectional motion, thereby improving the output force whilst also reducing noise or heat output. Further, a rapid compression mixing motion may be imparted to a received container through a single motor.

In certain embodiments, the third motor comprises a ball screw motor or a lead screw motor. The ball screw motor or the lead screw motor may be operably coupled to a corresponding screw threaded portion of the crank housing. The screw threaded portion of the crank housing, or the crank housing, may be moveable along the first longitudinal rail. The screw threaded portion of the crank housing, or the crank housing, may be slidably connected to the first longitudinal rail.

Thus, in some embodiments, the ball screw motor or the lead screw motor may cause the moveable plate to axially move along the longitudinal axis in a first direction, toward the holding element. Further, the ball screw motor or the lead screw motor may cause the moveable plate to axially move along the longitudinal axis in a second direction, opposite the first direction, away from the holding element. Thus, the ball screw motor or the lead screw motor may cause compression and/or decompression of a received container. The ball screw motor or the lead screw motor may cause a full compression and decompression cycle. The ball screw motor or the lead screw motor may cause a slower compression and decompression compared to the second motor. That is, the second motor may have a first compression and decompression cycle rate, and the third motor may have a second compression and decompression cycle rate, the first rate being greater than the second rate.

This provides the advantage that a slow longitudinal translation of the movable plate is provided, which is desirable for many unit operations in cell processing, such as breathing, gaseous exchange, harvesting or removal of contents of a container, or the like. This is particular advantageous in a self-container cell processing system.

Overall, in embodiments in which the abovementioned first, second and/or third motors, optionally in combination with the linkages described, are utilized, the following advantages are realized:

- the prerequisite motions can be achieved in a single apparatus—thus, a single apparatus may provide compression, wave, rocking and/or swirl motions to a received container;
- an increased power output;
- a reduced noise output;
- a reduced heat output, thus requiring less cooling equipment;
- reduced wear on components, particularly linkages connected to corresponding motors;
- there is no need to synchronize motors within the apparatus prior to use;
- composite mixing motions, such as a combination of compression and/or wave and/or rocking and/or swirl motions, may be achieved in a single apparatus;
- the respective motions may be tailored to a user's needs through control of the respective motors; and
- the motors may be positioned behind a received container, rather than directly thereunder, thereby reducing the height of the apparatus. This is an important consideration as space is limited in such laboratory and/or high-throughput settings.

Thus, an improved apparatus for imparting agitation and/or mixing to a received container is provided, especially for an apparatus for use in one or more unit operations of cell processing.

In certain embodiments, the or each motor comprises a stepper motor.

In certain embodiments, the or each motor is operably connected to one or more gearboxes.

That is, in some embodiments, one, more than one, some, most of all of the motors may be connected to one or more gearboxes. Each motor may have their own independent gearbox.

In certain embodiments, the apparatus further comprises a controller communicatively coupled to the actuation mechanism.

That is, in some embodiments, the apparatus may further include a controller. The controller may serve to control the actuation mechanism, or apportion thereof. The controller may be communicatively coupled, for example, electrically or mechanically coupled, to the actuation mechanism or a portion thereof. For example, the controller may be communicatively coupled to one or more motors, one or more linkages, one or more actuators or the like. The controller may take the form of a personal computer, a tablet, a smartphone or the like. The controller may include a series of pre-set programs for executing a pre-set motion of the moveable plate.

This provides the advantage that the user can customize the agitation motions. Furthermore, the user may easily select a pre-set agitation motion, thereby providing an apparatus that is more user friendly.

Yet further, the controller may allow for monitoring of a medium and/or cells or the like within a container arranged on the moveable plate, in use, such that an agitation motion can be adjusted in situ.

In certain embodiments, the apparatus further comprises one or more sensors, the or each sensor being configured to monitor, analyses, detect or the like a material within a container on the moveable plate. The or each sensor may be communicatively coupled to the controller. The or each sensor may be any appropriate sensor for monitoring, analyzing, detecting or the like a material within a container on the moveable plate.

In certain embodiments, the controller may upload data collated from the or each sensor to a personal computer, a smartphone, a tablet, a storage medium, an internet-based storage system, for example, the cloud, or the like.

This provides the advantage that collated data can be used to improve the application of the apparatus to different media and/or cells.

In certain embodiments, the controller includes a user interface such that a user can control, monitor or the like the apparatus, in use.

In certain embodiments, the apparatus further comprises one or more positioning sensors, the or each positioning senor communicatively coupled to the controller, wherein the controller generates a signal to the actuation mechanism based upon a signal received from the or each position sensor.

That is, in some embodiments, the apparatus comprises one or more sensors. The or each sensor may be arranged and/or configured to sense a position of the moveable plate relative to the first plane. The or each sensor may be communicatively coupled, for example, electrically or mechanically coupled, to the controller. The or each sensor may optionally be communicatively coupled, for example, electrically or mechanically coupled, to the actuation mechanism or a portion thereof, for example, one or more motors, one or more linkages, one or more actuators or the like. The sensor may be arranged to generate a signal, the signal may indicate a relative positioning of the moveable plate, a status of the actuation mechanism or a portion thereof, or the like, and to send such a signal to the controller. The controller may generate a signal to the actuation mechanism, or a portion thereof such as one or more motors, one or more linkages or one or more actuators, based upon the signal received from the or each sensor.

This provides the advantage that the actuation mechanism accurate executes the desired agitation motion.

Any holding element, actuation mechanism or any other feature can be used in combination with any other actuation mechanism, holding element or any other feature as disclosed herein. In particular, there may be a number of actuation mechanisms that can be used in combination. For example, the actuation mechanism may have a magnet-electromagnet arrangement in combination with a cam arrangement. In another example, any appropriate linear actuation mechanism, for example, a series of linear actuators, may be used in combination with any rotational actuation mechanism, for example, one or more linkages driven by motors. Any other combination is contemplated herein.

Alternatively, or in addition to any one of the embodiments discussed above, there is provided an apparatus for use in performing one or more unit operations in cell processing comprising a holding element arranged to receive a top section of a container within a first plane; a moveable plate, spaced apart from the holding element, arranged to operably engage a base section of a container, the moveable plate defining a second plane substantially parallel to the first plane; and an actuation mechanism operably coupled to the moveable plate and arranged to move the moveable plate along a longitudinal axis, substantially perpendicular to the first plane and the second plane, thereby reducing a distance between the second plane and the first plane. The distance between the entirety of the second plane and the entirety of the first plane may be reduced. Any one of the above embodiments of holding elements, actuation mechanisms, moveable plates, containers or the like may be used in combination with this particular embodiment of the apparatus. Equally, methods of use of the above particular embodiment are contemplated, i.e., axially translating the moveable plane in combination with, or as an alternative to, rotation about an axis within the second plane.

In another aspect of the disclosure there is provided a system for use in performing one or more unit operations in cell processing comprising:

an apparatus as described herein; and a container having a base section, a top section in parallel to the base section, and a compressible wall element extending substantially perpendicularly therebetween;

wherein the container is disposed between the holding element and the moveable plate, the actuation mechanism arranged to move the moveable plate such that at least a portion of the compressible wall element is at least partially compressed along a longitudinal axis perpendicular to the first plane and the second plane.

In certain embodiments, the base section of the container is fixedly attached to the moveable plate.

Thus, in certain embodiments, the base section is coupled, connected or otherwise attached to the moveable plate in a fixed manner. That is, there is a physical connection. As such, the base section of the container is directly moved by the apparatus. This may provide more controlled mixing of contents of the container.

In certain embodiments, the base section of the container is fixedly attached to the moveable plate by one or more adhesives, fasteners, or the like.

In certain embodiments, the base section of the container is engageable with the moveable plate.

Thus, in certain embodiments, the base section is not directly coupled, connected or otherwise attached to the moveable plate. That is, there is no physical connection. Instead, the base section is intermittently contactable with the moveable plate. As such, a so-called slapping effect may be achieved, whereby the moveable plate intermittently contacts, or "slaps," the base section of the container. This may provide improved mixing and, more particularly, improved suspension of cells within media.

In another aspect of the disclosure there is provided a system for use in performing one or more unit operations in cell processing comprising:

a container comprising a base section, a top section in parallel with the base section, and a compressible wall element extending substantially perpendicularly therebetween;

a holding element operably engaged with the top section of the container to hold the top section of the container within a first plane;

a moveable plate, spaced apart from the holding element, operably engaged with the base section of the container, the moveable plate defining a second plane substantially parallel to the first plane; and an actuation mechanism operably coupled to the movable plate to move the moveable plate about at least one axis within the second plane, thereby at least partially compressing at least a portion of the compressible wall element along a longitudinal axis perpendicular to the first plane and the second plane.

That is, there is also provided a system including the apparatus described herein and a container.

In certain embodiments, the base section of the container is fixedly attached to the moveable plate.

Thus, in certain embodiments, the base section is coupled, connected or otherwise attached to the moveable plate in a fixed manner. That is, there is a physical connection. As such, the base section of the container is directly moved by the apparatus. This may provide more controlled mixing of contents of the container.

In certain embodiments, the base section of the container is fixedly attached to the moveable plate by one or more adhesives, fasteners, or the like.

In certain embodiments, the base section of the container is engageable with the moveable plate.

Thus, in certain embodiments, the base section is not directly coupled, connected or otherwise attached to the moveable plate. That is, there is no physical connection. Instead, the base section is intermittently contactable with the moveable plate. As such, a so-called slapping effect may be achieved, whereby the moveable plate intermittently contacts, or "slaps," the base section of the container. This may provide improved mixing and, more particularly, improved suspension of cells within media.

In some embodiments, the container may include a base section, a top section extending in parallel to the base section, and a compressible wall element extending between the top section and the base section. The compressible wall element may extend substantially perpendicular to the top section and the base section.

In some embodiments, the container may include a base section, a top section extending in parallel to the base section, and a wall element extending between the top section and the base section. The wall element may be a compressible wall element, a flexible wall element, a deformable wall element, a resiliently deformable element or the like. The wall element may allow for compressibility along at least one axis. In some examples, a portion of the wall element of the container may be compressible, flexible, deformable, resiliently deformable or the like. The container may be a cell processing container. The container may be a cell culturing container. The container may be a bioreactor. The container may be a bellows, may comprise or form a bellows, may be a concertina, or may comprise or form a concertina. The container may be a bellow-based bioreactor. The container may include a lumen for receiving a cell processing medium or media or materials therein.

The apparatus, namely the holding element, may be arranged to receive the top section of the container. The holding element may be arranged to hold the top section of the container within a first plane.

The apparatus, namely the moveable plate, may be arranged to operably engage the base section of the container. The moveable plate may be coupled to the base section of the container. That is, there may be some physical connection between the moveable plate and the base section of the container. The moveable plate may be engageable with the base section of the container. That is, the moveable plate may not be in physical connection with the base section of the container, instead, the moveable plate may be configured and arranged to act upon the base section of the container. In some examples, the moveable plate is configured for face-to-face engagement with the base section of the container, in use.

The moveable plate is moveable about an axis of the second plane, which is defined by the plane of the moveable plate. As the moveable plate is caused to move, by the actuation mechanism, the base section of the container is caused to move. As the top section is held within the first plane, and as the second plane changes such that the base section of the container changes, this causes compression of at least a portion of the compressible wall element. The compressible wall element may be compressible along a longitudinal axis extending substantially perpendicular to the first plane and the second plane, and substantially parallel to the compressible wall element. That is, a distance between at least a portion of the second plane and the first plane is reducible, in use. As a result, the container, specifically the compressible wall element, may be compressed.

In some examples, the moveable plate may be moveable along the longitudinal axis to compress the container, specifically the wall element thereof, as the entirety of the second plane is caused to move toward the first plane.

Any of the features discussed in relation to the apparatus may form part of the system.

In particular embodiments, the system may further comprise a platform, for example, a cell processing platform, sealingly engaged with the top section of the container. The top section of the container may include a passageway for a fluid. The platform may form a liquid, preferably a fluid, tight seal at, near or around the passageway for a fluid of the container. The platform may include at least one inlet fluidly connected to at least one outlet. In preferred examples, the platform may include at least one inlet, for example, a plurality of inlets, fluidly connected, or directly fluidly connected, to an, for example, a single, outlet. The or each outlet of the platform may be in fluid communication with the passageway of the container.

In particular embodiments, the platform may comprise at least one auxiliary container sealingly engaged with the platform. The or each auxiliary container may include a passageway for fluid. The passageway of the or each auxiliary container may be fluidly connected, or directly fluidly connected, to one or more inlets of the platform. Thus, a fluid passageway may be formed from one or more auxiliary containers, for example, from a lumen of the or each auxiliary container, through the platform, and into a lumen of the container.

In some embodiments, the auxiliary container may include a base section, a top section extending in parallel to the base section, and a wall element extending between the top section and the base section. The wall element may be a compressible wall element, a flexible wall element, a deformable wall element, a resiliently deformable element or the like. The wall element may allow for compressibility along at least one axis, for example, along a longitudinal axis extending perpendicularly to the top and base sections. In some examples, a portion of the wall element of the container may be compressible, flexible, deformable, resiliently deformable or the like. The auxiliary container may be a cell processing container. The auxiliary container may be a cell culturing container. The auxiliary container may be a bioreactor, for example, an additional or a secondary bioreactor. The auxiliary container may be a breather container, for example, a breather bellows. That is, the auxiliary container may compensate for changes in pressure within a primary container as discussed herein. The auxiliary container may be a bellows, may comprise or form a bellows, may be a concertina, or may comprise or form a concertina. The auxiliary container may be a bellow-based breathing container. The auxiliary container may include a lumen for receiving cell processing medium or media or materials therein.

In some embodiments, the platform, for example, a cell processing platform, may comprise a primary container, for example, a bioreactor, sealingly engaged at a first side thereof, and one or more secondary or auxiliary containers sealingly engaged at a second side thereof. As described above, the primary container may be in fluid communication with an outlet of the platform, and/or the or each secondary container may be in fluid communication with one or more inlets of the platform. The or each secondary container may include a top section, a base section extending in parallel to the top section, and a compressible wall element therebetween. The or each primary container, for example, a bioreactor or cell processing container or cell culture container, may include a top section, a base section extending in parallel to the top section, and a compressible wall element therebetween. In use, the or each primary container may be in fluid communication, through the, or via the, platform with the or each secondary container. Thus, in use, when the primary container is compressed, rotated, swirled or the like by the moveable plate, the or each secondary container may compensate for pressure increases or decreases within the or each primary container. That is, the secondary container may act as a breathing container, that allows for fluid to be expelled into, and drawn in from, the secondary container as the pressure within the primary container moves.

This provides the advantage that there is no accumulation of vacuum or pressure in the primary container. This may be beneficial in, for example, a cell culturing container.

In another aspect of the disclosure there is provided a method of processing cells, the method comprising:

providing a cell processing medium in a container, the container having a base section, a top section in parallel to the base section, and a compressible wall element extending substantially perpendicularly therebetween;

holding the top section of the container within a first plane;

engaging the base section of the container with a moveable plate defining a second plane substantially parallel to, and spaced apart from, the first plane;

rotating the base section of the container about at least one axis within the second plane, thereby causing turbulence of the cell processing medium within the container.

The moveable plate may be any moveable plate as discussed herein in relation to the apparatus or the system.

That is, the step of rotating the base section of the container about at least one axis within the second plane may thereby cause agitation, mixing, turbulence, or the like, of the cell processing medium within the container.

In certain embodiments, the step of rotating the base section of the container comprises rotating the base section of the container about an axis within the second plane.

In some examples, this may thereby cause wave turbulence of the cell processing medium within the container.

That is, in some embodiments, rotating the base section of the container about the axis within the second plane causes turbulence of the cell processing medium, for example, a wave motion, a wave agitation or a wave turbulence. That is, the cell processing medium may be forced toward one side of the container adjacent a wall element, and then toward an opposing side of the container adjacent an opposing wall element, thereby causes a wave, or a wave effect.

In certain embodiments, a longitudinal axis, extending perpendicularly to the first plane and the second plane, intersects the second plane at an origin, wherein the step of rotating the base section of the container comprises pivoting the base section of the container about the origin.

In some examples, this may thereby cause swirling turbulence of the cell processing medium within the container.

That is, in some embodiments, pivoting the base section of the container about the origin causes turbulence of the cell processing medium, for example, a swirl motion, a swirl agitation or a swirl turbulence. That is, the cell processing medium may be forced to rotate about a longitudinal axis, for example, a central longitudinal axis, of the container, that is, in a swirling manner.

In certain embodiments, the origin is centrally located within the second plane.

In certain embodiments, the method further comprises the step of compressing the compressible container along a longitudinal axis that is perpendicular to the first plane and the second plane.

In some embodiments, the step of holding the top section of the container comprising holding the top section of the container within a first plane by a holding element.

The holding element may be any holding element as discussed herein in relation to the apparatus or the system.

In some embodiments, the step of rotating the base section of the container about at least one axis within the second plane comprises actuating an actuation mechanism operably coupled to the moveable plate.

In some embodiments, the step of engaging the base section of the container with a moveable plate comprises forming a physical connection between the base section of the container and the moveable plate. In other embodiments, the step of engaging the base section of the container with a moveable plate comprises forming an intermittent (i.e., a non-continuous) connection between the base section of the container and the moveable plate.

The actuation mechanism may be any actuation mechanism as discussed herein in relation to the apparatus or the system.

The apparatus or system may be used in the context of cell and/or gene therapy manufacturing.

The apparatus or system may be housed within a cell processing unit. Preferably, the cell processing unit comprises an incubator. The incubator may include a supply of gas, such as oxygen and/or carbon dioxide. The incubator may comprise a controller configured to control the apparatus described herein, the system described herein, or the incubator per se, such as the control of gaseous supply thereto.

Cell Processing Method

According to a further aspect of the disclosure, there is provided a method of processing cells, the method comprising:

(a) providing a compressible container comprising a population of cells in a liquid medium; and (b) maintaining the population of cells in the liquid medium, while pressure is applied to at least a portion of the compressible container so as to compress the container.

In one embodiment, the liquid medium is retained in the compressible container after compression is applied.

In one embodiment, the compressible container is comprised within the apparatus of the first aspect of the disclosure, or the system of the second or third aspects of the disclosure.

According to a further aspect of the disclosure, there is provided a method of processing cells using the apparatus of the first aspect of the disclosure, wherein the apparatus further comprises a container.

In one embodiment, the container is as described elsewhere herein. In one embodiment the container is suitable for containing a population of cells in a liquid medium. In one embodiment the container is compressible.

In one embodiment, the method comprises the steps of:

(a) providing a population of cells in a liquid medium within the container;

(b) operating the apparatus to process the population of cells in the liquid medium.

According to a further aspect of the disclosure, there is provided a method of processing cells, the method comprising:

(a) providing an apparatus according to the first aspect of the disclosure, wherein the apparatus further comprises a container comprising a population of cells in a liquid medium;

(b) operating the apparatus to process the population of cells in the liquid medium.

In one embodiment, processing the population of cells comprises maintaining the population of cells in the liquid medium, while pressure is applied to at least a portion of the container so as to compress the container.

According to a further aspect of the disclosure, there is provided a method of processing cells using the system according to the second or third aspects of the disclosure.

In one embodiment the container of the system is compressible.

In one embodiment, the method comprises the steps of:

(a) providing a population of cells in a liquid medium within the container;

(b) operating the system to process the population of cells in the liquid medium.

According to a further aspect of the disclosure, there is provided a method of processing cells, the method comprising:

(a) providing a system according to the second or third aspects of the disclosure, wherein the container comprises a population of cells in a liquid medium;

(b) operating the system to process the population of cells in the liquid medium.

In one embodiment, processing the population of cells comprises maintaining the population of cells in the liquid medium, while pressure is applied to at least a portion of the container so as to compress the container.

Suitably the container is compressible. Suitably the compressible container is adapted for cell storage and/or culture. Suitably the compressible container is sterile.

Suitably the compressible container comprises a volume suitable for cell culture, suitably on an industrial scale. Suitably the compressible container comprises a volume of between 1 μl up to 1000 L. Suitably the compressible container comprises a volume of at least 50 ml, suitably up to 1 liter. Suitably this is the decompressed volume of the container.

Suitably the compressible container is a bioreactor. Suitably the compressible container is operable to expand and contract. Suitably the compressible container comprises bellows. Suitably the compressible container comprises a bellows bioreactor. In one embodiment, the compressible container is the bellows bioreactor described in WO2016/185221.

Suitably the compressible container is mounted within a device. Suitably the device is operable to apply pressure to at least a portion of the compressible container. Suitably the device is operable to release pressure from the compressible container. Suitably the device is operable to thereby compress and decompress the compressible container as explained elsewhere herein. In one embodiment, the device is the apparatus according to the first aspect of the disclosure, or the system according to the second or third aspects of the disclosure, and as described elsewhere herein.

Suitably the population of cells comprises one or more cells present in a liquid medium.

Suitably the population of cells may comprise any cell type. Suitably the population of cells may comprise a homogenous population of cells. Alternatively the population of cells may comprise a mixed population of cells.

Suitably the population of cells may comprise any human or animal cell type, for example: any type of adult stem cell or primary cell, T cells, CAR-T cells, monocytes, leukocytes, erythrocytes, NK cells, gamma delta t cells, tumor infiltrating t cells, mesenchymal stem cells, embryonic stem cells, induced pluripotent stem cells, adipose derived stem cells, Chinese hamster ovary cells, NS0 mouse myeloma cells, HELA cells, fibroblasts, HEK cells, insect cells, organoids etc. Suitably the population of cells may comprise T-cells.

Alternatively, the population of cells may comprise any microorganism cell type, for example: bacterial, fungal, Archaean, protozoan, algal cells.

Suitably the liquid medium may be any sterile liquid capable of maintaining cells. Suitably the liquid medium may be selected from: saline or may be a cell culture medium. Suitably the liquid medium is a cell culture medium selected from any suitable medium, for example: DMEM, XVIVO 15, TexMACS. Suitably the liquid medium is appropriate for the type of cells present in the population. The skilled person is aware of suitable media to use when culturing cells.

For example, the population of cells comprises T cells and the liquid medium comprises XVIVO 10.

Suitably the liquid medium may further comprise additives, for example: growth factors, nutrients, buffers, minerals, stimulants, stabilizers or the like.

Suitably the liquid medium comprises growth factors such as cytokines and/or chemokines. Suitably the growth factors are appropriate for the type of cells present in the population and the desired process to be carried out. Suitably the liquid medium comprises stimulants such as antigens or antibodies, which may be mounted on a support. Suitable stimulants are appropriate for the type of cells present in the population and the desired process to be carried out. Suitably, when culturing T-cells, for example, antibodies are provided as a stimulant in the liquid medium. Suitably the antibodies are mounted on an inert support such as beads, for example: dynabeads.

Suitably the additives are present in the liquid medium at an effective concentration. An effective concentration can be determined by the skilled person on the basis of the population of cells and the desired process to be carried out using known teachings and techniques in the art.

Suitably the population of cells are seeded in the liquid medium at a concentration of between $1\times10^4$ cfu/ml up to $1\times10^8$ cfu/ml.

Suitably the methods of the disclosure may be batch, fed-batch or continuous methods of processing cells, or combinations thereof.

Suitably the liquid medium may be fed in batches during the process to reach a desired volume, suitably this is known as a batch-fed process. Suitably the liquid medium is fed in batches into the compressible container. Suitably the liquid medium may be replaced, suitably by fresh medium. Suitably the liquid medium may be replaced by batch-fed medium replacement. Suitably this may be known as perfusion culture.

Suitably the methods of the disclosure may be fed-batch for a period of time and then fed-batch with media replacement. Suitably the methods of the disclosure may be fed-batch for a period of time and then perfusion for a period of time.

Suitably batch-fed medium replacement or perfusion may be achieved by compression of the compressible container to expel medium from the container, and addition of fresh medium into the container.

Suitably the liquid medium may be present at the desired volume at the start of the method, and no further medium may be added. Suitably this is known as a batch process.

Suitably the liquid medium may be added continuously to the container throughout the method to maintain a desired volume. Suitably this is known as a continuous process.

Suitably the desired total volume of the medium is calculated based on the type of processing and cells used in the method.

Suitably, in a fed-batch process, the medium may be fed in batches of 50 mL to 500 mL.

Suitably the liquid medium is fed into the compressible container at different times during the process.

Suitably the amount of liquid medium fed into the compressible container at any given time during the process may vary depending on the step of the process and the cell processing being carried out.

Suitably during a step under static conditions, between 0 mL and 200 mL per day is fed into the compressible container.

Suitably during a step under dynamic conditions, between 0 mL and 500 mL per day is fed into the compressible container.

Suitably during a step under compression, between 0 mL and 800 mL per day is fed into the compressible container.

Suitably maintaining the population of cells in the liquid medium may comprise carrying out any type of cell processing.

Suitably cell processing may comprise culturing, mixing, washing, expanding, genetically modifying, stimulating, transforming, transfecting, producing a population of cells, arrest of cell growth, selection of cells, freezing, or thawing of cells.

Suitably cell processing may comprise derivation/isolation of primary cells from solid biopsies, embryonic and fetal matter, blood and other liquid samples.

Suitably cell processing may comprise decellularization of solid tissue, suitably for tissue engineering.

Suitably cell processing may comprise: the growth of organoids, the growth of cells on microcarriers, or the growth of cellular aggregates.

Suitably the methods of processing cells may comprise more than one type of cell processing. Suitably the methods of processing cells may comprise a plurality of different steps of cell processing. Suitably the different steps of cell processing may be selected from any of the types of cell processing above.

For example, the methods of processing cells may include a step of growing cellular aggregates (for example, embryoid bodies) before a step of expanding the cellular aggregates.

Typically, the step of maintaining the population of cells in the liquid medium comprises culturing the population of cells in the liquid medium. Suitably culturing the population of cells comprises expanding the population of cells in the liquid medium.

Suitably the population of cells are maintained in the liquid medium for a sufficient period of time for the desired cell processing to be completed.

The process of the disclosure comprises at least a step of maintaining the population of cells in the liquid medium, while pressure is applied to at least a portion of the compressible container so as to compress the container. Suitably the process of the disclosure may further comprise other cell processing steps as described above.

Suitably, the or each further processing step of the methods may be performed under any conditions. Suitably the or each further processing step of the methods may be carried out under static or dynamic conditions.

Suitably the process may further comprise one or more steps of maintaining the population of cells under static or dynamic conditions. Suitably the process may further comprise one or more steps of culturing the population of cells under static or dynamic conditions. Suitably such additional steps are carried out prior to compression step (b).

Suitably the process comprises at least one step of maintaining the population of cells under static or dynamic conditions, suitably prior to step (b).

Suitably the process comprises at least one step of maintaining the population of cells under static conditions and at least one step of maintaining the population of cells under dynamic conditions, suitably prior to step (b).

Suitably the process may comprise multiple static and/or dynamic steps, suitably prior to step (b). Suitably the process may comprise a first static step and a first dynamic step. Suitably the process may further comprise a second static step and a second dynamic step. Suitably the static and dynamic steps may alternate.

For example, the process may comprise:

(a) providing a compressible container comprising a population of cells in a liquid medium;
(b) maintaining the population of cells in the liquid medium under static conditions; and/or
(c) maintaining the population of cells in the liquid medium under dynamic conditions; and
(d) maintaining the population of cells in the liquid medium, while pressure is applied to at least a portion of the compressible container so as to compress the container.

For example, the process may comprise:

(a) providing a compressible container comprising a population of cells in a liquid medium;
(b) maintaining the population of cells in the liquid medium under a first period of static conditions;
(c) maintaining the population of cells in the liquid medium under a first period of dynamic conditions;
(d) maintaining the population of cells in the liquid medium under a second period of static conditions;
(e) maintaining the population of cells in the liquid medium under a second period of dynamic conditions; and
(f) maintaining the population of cells in the liquid medium, while pressure is applied to at least a portion of the compressible container so as to compress the container.

Suitably maintenance under static conditions means that the population of cells in the liquid medium is not subject to any substantial movement or force.

Suitably maintenance under dynamic conditions means that the population of cells in the liquid medium is subject to movement or force.

There are many different types of dynamic cell culturing techniques known in the art, suitably any dynamic culturing technique may be used in the processes of the disclosure. For example; the dynamic conditions may comprise any form of agitation of the liquid medium, for example: a rocking, rotational, stirring, waving, agitating, swirling motion. Suitably therefore, maintenance of the population of cells in the liquid medium under dynamic conditions may comprise applying a rocking, stirring, waving, agitating, or swirling motion to the liquid medium. Suitably each dynamic step of the process may comprise a different form of dynamic condition.

For example, a first dynamic step of the process may comprise maintenance of the population of cells in the liquid medium under dynamic conditions comprises applying a rocking motion to the liquid medium, and a second dynamic step of the process may comprise maintenance of the population of cells in the liquid medium under dynamic conditions comprises applying a wave motion to the liquid medium.

Suitably the dynamic conditions applied to the population of cells may be applied at a particular speed or frequency. Suitably such speed or frequency may be varied. Suitably a rocking motion may comprise any speed. Suitably the rocking motion comprises a speed defined in rocks per minute (rpm). For example, the rocking motion comprises an rpm of from 20 rpm to 60 rpm. For example, the rocking motion comprises an rpm of between 20 rpm and 60 rpm.

It is possible that each dynamic step of the process may comprise the same form of dynamic condition but applied at a different speed or frequency. For example, a first dynamic step of the process may comprise maintenance of the population of cells in the liquid medium under dynamic conditions comprises applying a rocking motion to the liquid medium at a speed of 60 rpm and a second dynamic step of the process may comprise maintenance of the population of cells in the liquid medium under dynamic conditions comprises applying a rocking motion to the liquid medium at a speed of 20 rpm.

Suitably different speeds may be used in the process, suitably during different dynamic steps. For example, the first dynamic step may comprise applying a rocking motion to the liquid medium at a speed of 60 rpm, and the second dynamic step may comprise applying a rocking motion to the liquid medium at a speed of 20 rpm.

It should be understood that compression step (b) may also comprise maintaining the population of cells under dynamic conditions. Suitably during compression of the compressible container, the liquid medium is agitated, and thereby compression of the compressible container also provides dynamic conditions. In particular, when using a compressible container comprising bellows, upon compression the liquid medium is in contact with the creases of the bellows, and upon expansion, the liquid medium is lifted and falls from the creases of the bellows. Therefore, suitably the population of cells may be maintained under dynamic conditions by the compression of the compressible container in step (b) of the process.

Suitably the process itself lasts for a period of time, which is sufficient to complete the desired processing of the cells. Such periods of time will be known to the skilled person, however suitably the process may take a plurality of minutes, hours, days, weeks or months, suitably between 1 minute to several months, suitably between 1 minute to 2 weeks, suitably between 1 hour to 2 weeks, suitably between 1 day to 14 days, suitably between 5 to 14 days.

Suitably each processing step lasts for a defined period of time.

Suitably each processing step may last for a period of time within the ranges defined above which is suitable to achieve the intended processing of the cells.

Suitably the process of the disclosure comprises a step of applying pressure to at least a portion of the compressible container so as to compress the container.

Suitably the pressure is applied linearly by compression of the compressible container.

Suitably the pressure is applied by linear compression of the compressible container.

Suitably by linear compression or linearly it is meant that the pressure is applied in the direction of the longitudinal axis of the compressible container i.e., between the base and the top of the container.

Suitably compression of the compressible container comprises applying a force to the top and/or base of the container to compress the container. Suitably, if the compressible container comprises bellows, compression of the compressible container comprises applying a force to the top and/or base of the container to collapse the bellows of the container.

Suitably the compressible container is compressed by a device in which the compressible container may be mounted. Suitably the device is operable to apply pressure to at least a portion of the compressible container. Suitably the device is operable to release pressure from the compressible container. Suitably the device is operable to thereby compress and decompress the compressible container as explained elsewhere herein. In one embodiment, the device is the apparatus according to the first aspect of the disclosure, or the system according the second or third aspects of the disclosure, as described elsewhere herein.

Suitably the pressure that is applied is not constant. Suitably the pressure is applied to at least a portion of the compressible container in a cycle. Suitably cyclic pressure is applied to the compressible container, suitably by cyclic compression of the compressible container.

Suitably by cyclic pressure it is meant that the pressure is applied and released in a cycle.

Suitably by cyclic compression it is meant that the compressible container is compressed and decompressed in a cycle.

Suitably, upon compression of the compressible container pressure is applied to at least a part of the compressible container, and upon decompression of the compressible container pressure is released from at least a part of the compressible container.

Suitably, therefore step (b) comprises applying cyclic pressure to at least a portion of the compressible container.

Suitably step (b) may comprise applying cyclic pressure to at least a portion of the compressible container so as to compress and decompress the container.

Suitably the cyclic pressure is applied at a suitable speed. Suitably the speed is defined as number of cycles per minute (cpm). Suitably the cyclic pressure may be applied at a speed of around 60 cpm, for example.

Suitably the cyclic pressure is applied at a suitable amplitude. Suitably the amplitude may be defined as a portion of the total height of the compressible container. For example, the cyclic pressure may be applied at an amplitude of 50% to 80% of the total height of the container. This would mean that in each compression of the compressible container, the height is reduced by 50-80% of the total height of the container. Alternatively, the amplitude may be defined as the distance that the moveable plate of the apparatus or system moves in order to apply pressure or release pressure from the compressible container. For example, the cyclic pressure may be applied at an amplitude of from 5 mm to 25 mm. For example, the cyclic pressure may be applied at an amplitude of between 5 mm and 25 mm.

The disclosure may be defined by one or more of the following, non-limiting, examples, which can be used in any combination:

Example 1: An apparatus for use in performing one or more unit operations in cell processing comprising: a holding element arranged to receive a top section of a container within a first plane; a moveable plate, spaced apart from the holding element, arranged to operably engage a base section of a container, the moveable plate defining a second plane substantially parallel to the first plane; and an actuation mechanism operably coupled to the moveable plate to rotate the moveable plate about at least one axis within the second plane, thereby reducing a distance between at least a portion of the second plane and the first plane.

Example 2: An apparatus according to example 1, wherein the actuation mechanism is arranged to rotate the moveable plate about an axis within the second plate.

Example 3: An apparatus according to example 1, wherein the actuation mechanism is arranged to rotate the moveable plate about a plurality of axes within the second plane.

Example 4: An apparatus according to any preceding example, wherein the actuation mechanism is arranged to rotate the moveable plate between 0 degrees and 90 degrees about the or each axis.

Example 5: An apparatus according to any preceding example, a longitudinal axis, extending perpendicularly to the first plane and the second plane, intersects the second plane at an origin, wherein the actuation mechanism is arranged to pivot the moveable plate about the origin.

Example 6: An apparatus according to example 5, wherein the origin is centrally located within the second plane.

Example 7: An apparatus according to example 5 or example 6, wherein the moveable plate is pivotable about the origin such that each point within the second plane, excluding the origin, forms an angle with respect to the longitudinal axis between 0 and 180 degrees, excluding 90 degrees.

Example 8: An apparatus according to any preceding example, wherein the actuation mechanism is further arranged to move the moveable plate along a longitudinal axis, substantially perpendicular to the first plane and the second plane, thereby reducing a distance between the second plane and the first plane.

Example 9: An apparatus according to any preceding example, wherein the holding element comprises a platform operably engageable with a top section of a container, a clamping mechanism operably engageable with a top section of a container, or a sealing plate operably engageable with a top section of a container.

Example 10: An apparatus according to any preceding example, wherein the actuation mechanism comprises a base plate spaced apart from, and substantially parallel to, the moveable plate, the base plate being operably coupled to the moveable plate.

Example 11: An apparatus according to example 10, wherein the base plate comprises at least one actuator, the or each actuator being operably coupled to, or operably engageable with, the moveable plate.

Example 12: An apparatus according to example 10 or example 11, wherein the base plate comprises at least one rail, the or each rail upstanding from the base plate substantially perpendicularly to the base plate, the moveable plate being slidably coupled to the or each rail, and wherein at least one actuator is arranged to slide at least a portion of the moveable plate along the or each rail.

Example 13: An apparatus according to any one of examples 10 to 12, wherein the base plate is operably coupled to the moveable plate by at least one biasing element, the or each biasing element arranged to bias the moveable plate toward the base plate such that the second plane is substantially parallel to the first plane.

Example 14: An apparatus according to example 13, wherein the or each biasing element comprises a spring, preferably a tension spring.

Example 15: An apparatus according to any one of examples 10 to 14, wherein the base plate further comprises a rotatable support plate arranged to rotate about a longitudinal axis that is substantially perpendicular to the support plate, the support plate comprising the or each actuator.

Example 16: The apparatus according to any one of examples 10 to 15, wherein the or each actuator comprises a linear actuator.

Example 17: An apparatus according to any one of examples 10 to 16, wherein the moveable plate comprises at least one permanent magnet, and the base plate comprises at least one corresponding electromagnet.

Example 18: An apparatus according to example 17, wherein the or each permanent magnet is distal to a center of the moveable plate, and wherein the or each electromagnet is distal to a center of the base plate.

Example 19: An apparatus according to any one of examples 10 to 18, wherein the base plate comprises at least one cam member, the or each cam member operably engageable with the moveable plate, wherein the or each cam member is driven by a motor.

Example 20: An apparatus according to any one of examples 10 to 19, wherein the base plate comprises a central hub, coaxial with, and rotatable about, a longitudinal axis that is perpendicular to the base plate, the central hub including a connecting rod extending radially outwardly from the central hub and terminating in a wheel, the wheel being operably engageable with the moveable plate.

Example 21: An apparatus according to example 20, wherein the central hub is caused to rotate about the longitudinal axis by a motor.

Example 22: An apparatus according to any one of examples 10 to 21, wherein the base plate comprises a first linkage operably coupled to the moveable plate, the first linkage being driven by a first motor.

Example 23: An apparatus according to example 22, wherein the base plate further comprises a second linkage operably coupled to the moveable plate, the second linkage driven by a second motor.

Example 24: An apparatus according to example 23, wherein the first linkage and the second linkage are operably coupled at opposing edges of the moveable plate.

Example 25: An apparatus according to example 23, wherein the base plate further comprises a third linkage operably coupled to the moveable plate, the third linkage driven by a third motor.

Example 26: An apparatus according to example 25, wherein the first linkage, the second linkage and the third linkage are operably coupled to the moveable plate in a triangular arrangement.

Example 29: An apparatus according to any one of examples 1 to 9, wherein the actuation mechanism comprises a first motor, operably coupled to the moveable plate, configured to rotate the moveable plate about the at least one axis within the second plane.

Example 30: An apparatus according to example 29, wherein the actuation mechanism further comprises a second motor, operably coupled to the moveable plate, configured to move the moveable plate along a longitudinal axis, substantially perpendicular to the first plane and the second plane, thereby reducing a distance between the second plane and the first plane.

Example 31: An apparatus according to example 30, wherein the actuation mechanism further comprises a third motor, operably coupled to the moveable plate, configured to move the moveable plate along the longitudinal axis, thereby reducing a distance between the second plane and the first plane.

Example 32: An apparatus according to example 31, wherein the actuation mechanism further comprises a linkage, the linkage comprising: a crank housing, comprising a rotatable crank, slidable along a first longitudinal rail, extending substantially parallel to the longitudinal axis; and a slider portion, operably coupled to the moveable plate, slidable along a second longitudinal rail, extending substantially parallel to the first longitudinal rail, the slider portion being operably coupled to the rotatable crank by a connecting rod; wherein the second motor is operably coupled to the rotatable crank so as to rotate the same and move the slider portion along the second longitudinal rail, and wherein the third motor is operably connected to the crank housing so as to move the crank housing along the first longitudinal rail.

Example 33: An apparatus according to example 32, wherein the third motor comprises a ball screw motor or a lead screw motor, operably coupled to a corresponding screw threaded portion of the crank housing, the screw threaded portion of the crank housing being moveable along the first longitudinal rail.

Example 34: An apparatus according to any one of examples 19 to 33, wherein the or each motor comprises a stepper motor.

Example 35: An apparatus according to any one of examples 19 to 34, wherein the or each motor is operably connected to one or more gearboxes.

Example 36: An apparatus according to any preceding example, further comprising a controller communicatively coupled to the actuation mechanism.

Example 37: An apparatus according to example 36, further comprising one or more positioning sensors, the or each positioning senor communicatively coupled to the controller, wherein the controller generates a signal to the actuation mechanism based upon a signal received from the or each position sensor.

Example 38: A system for use in performing one or more unit operations in cell processing comprising: an apparatus according to any preceding example; and a container having a base section, a top section in parallel to the base section, and a compressible wall element extending substantially perpendicularly therebetween; wherein the container is at least partially disposed between the holding element and the moveable plate, the actuation mechanism arranged to move the moveable plate such that at least a portion of the compressible wall element is at least partially compressed along a longitudinal axis perpendicular to the first plane and the second plane.

Example 39: A system for use in performing one or more unit operations in cell processing comprising: a container comprising a base section, a top section in parallel with the base section, and a compressible wall element extending substantially perpendicularly therebetween; a holding element operably engaged with the top section of the container to hold the top section of the container within a first plane; a moveable plate, spaced apart from the holding element, operably engaged with the base section of the container, the moveable plate defining a second plane substantially parallel to the first plane; and an actuation mechanism operably coupled to the movable plate to move the moveable plate about at least one axis within the second plane, thereby at least partially compressing at least a portion of the compressible wall element along a longitudinal axis perpendicular to the first plane and the second plane.

Example 40: A system according to example 39 or example 40, wherein the base section of the container is fixedly attached to the moveable plate.

Example 41: A system according to example 39 or example 40, wherein the base section of the container is removably engageable or engaged with the base section of the container.

Example 42: A method of processing cells, the method comprising: providing a cell processing medium in a container, the container having a base section, a top section in parallel to the base section, and a compressible wall element extending substantially perpendicularly therebetween; holding the top section of the container within a first plane; engaging the base section of the container with a moveable plate defining a second plane substantially parallel to, and spaced apart from, the first plane; rotating the base section of the container about at least one axis within the second plane, thereby causing turbulence of the cell processing medium within the container.

Example 43: A method according to example 42, wherein the step of rotating the base section of the container comprises rotating the base section of the container about an axis within the second plane.

Example 44: A method according to example 42, wherein a longitudinal axis, extending perpendicularly to the first plane and the second plane, intersects the second plane at an origin, wherein the step of rotating the base section of the container comprises pivoting the base section of the container about the origin.

Example 45: A method according to example 44, wherein the origin is centrally located within the second plane.

Example 46: A method of manufacturing an apparatus according to any one of examples 1 to 37, or a system according to any one of examples 38 to 41.

Example 47: A method of processing cells, the method comprising: (a) providing a compressible container comprising a population of cells in a liquid medium; and (b) maintaining the population of cells in the liquid medium, while pressure is applied to at least a portion of the compressible container so as to compress the container.

Example 48: A method according to example 47, wherein the liquid medium is retained in the compressible container after compression is applied.

Example 49: A method of processing cells using the apparatus of any one of examples 1 to 37, wherein the apparatus further comprises a container.

Example 50: A method according to example 49, wherein the container is suitable for containing a population of cells in a liquid medium.

Example 51: A method according to example 49 or 50, wherein the container is compressible.

Example 52: A method according to any one of examples 49 to 51, wherein the method comprises the steps of: (a) providing a population of cells in a liquid medium within the container; (b) operating the apparatus to process the population of cells in the liquid medium.

Example 53: A method of processing cells, the method comprising: (a) providing an apparatus according to any one of examples 1 to 37, wherein the apparatus further comprises a container comprising a population of cells in a liquid medium; (b) operating the apparatus to process the population of cells in the liquid medium.

Example 54: The method of example 52 or 53, wherein processing the population of cells comprises maintaining the population of cells in the liquid medium, while pressure is applied to at least a portion of the container so as to compress the container.

Example 55: A method of processing cells using the system of any one of examples 38 to 41.

Example 56: A method according to example 55, wherein the container of the system is compressible.

Example 57: A method according to examples 55 or 56, wherein the method comprises the steps of: (a) providing a population of cells in a liquid medium within the container; (b) operating the system to process the population of cells in the liquid medium.

Example 58: A method of processing cells, the method comprising: (a) providing a system according to any one of examples 38 to 41, wherein the container comprises a population of cells in a liquid medium; (b) operating the system to process the population of cells in the liquid medium.

Example 59: A method according to examples 57 or 58 wherein processing the population of cells comprises maintaining the population of cells in the liquid medium, while pressure is applied to at least a portion of the container so as to compress the container.

Example 60: An apparatus for use in performing one or more unit operations in cell processing comprising: a holding element arranged to receive a top section of a container within a first plane; a moveable plate, spaced apart from the holding element, arranged to operably engage a base section of a container, the moveable plate defining a second plane substantially parallel to the first plane; and an actuation mechanism operably coupled to the moveable plate to translate moveable plate along a longitudinal axis, substantially perpendicular to the first plane and the second plane, thereby reducing a distance between the second plane and the first plane.

Example 61: A method of processing cells, the method comprising: providing a cell processing medium in a container, the container having a base section, a top section in parallel to the base section, and a compressible wall element extending substantially perpendicularly therebetween; holding the top section of the container within a first plane; engaging the base section of the container with a moveable plate defining a second plane substantially parallel to, and spaced apart from, the first plane; translating the base section of the container along a longitudinal axis, substantially perpendicular to the first plane and the second plane, thereby causing compression and/or decompression of the container.

BRIEF DESCRIPTION OF THE DRAWINGS

Example embodiments of the disclosure are now described, by way of example only, hereinafter with reference to the accompanying drawings, in which.

DETAILED DESCRIPTION

Figure 1A:
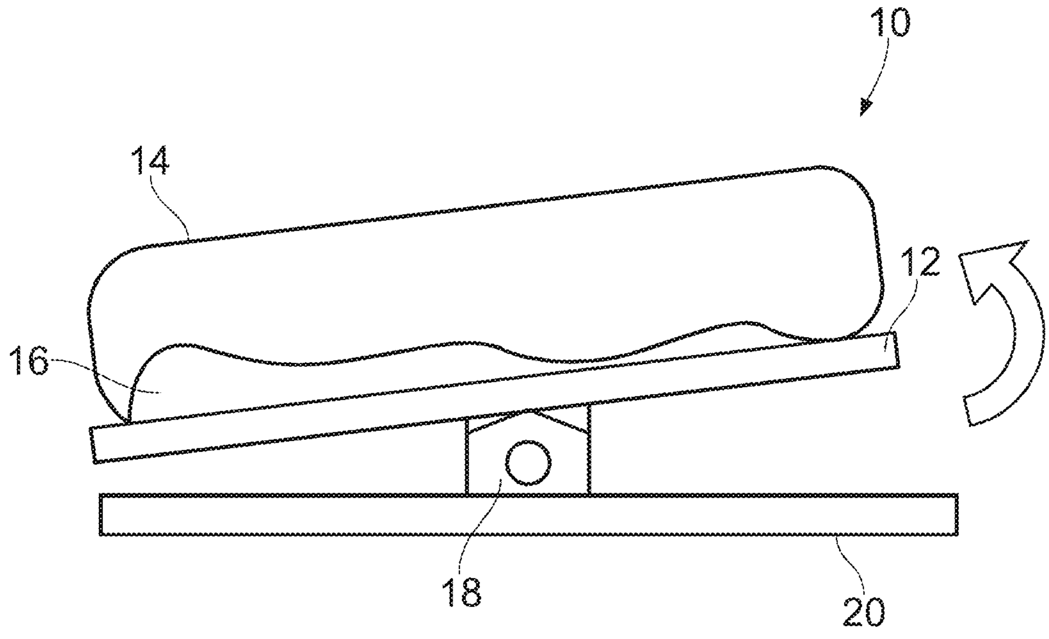
FIG. 1(a) (Prior Art)
FIGS. 1(*a*) and 1(*b*) illustrates an example of the prior art.
Figure 1B:
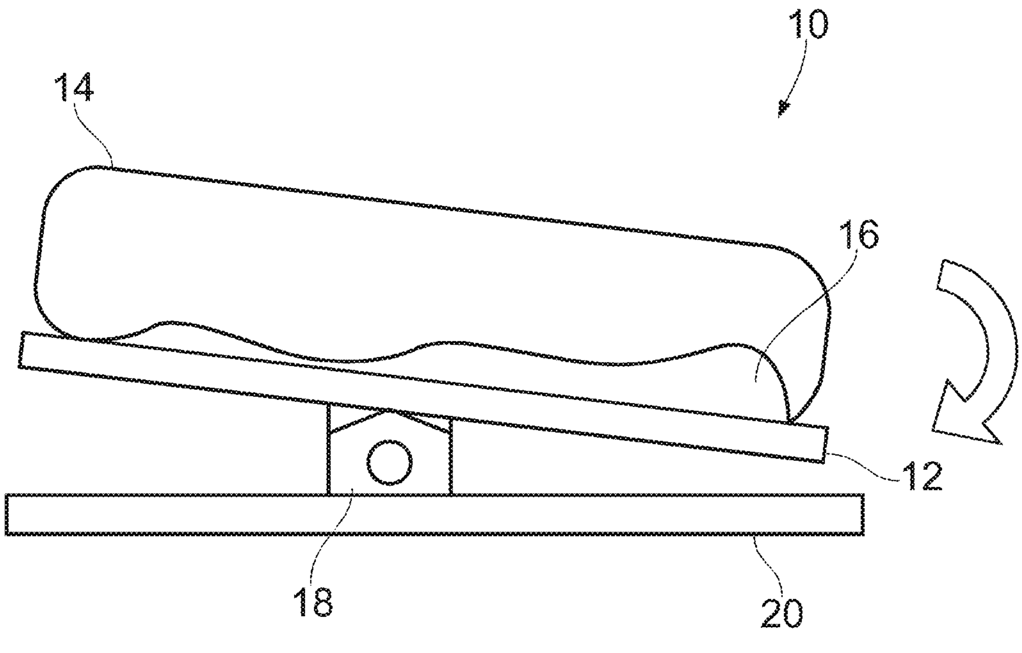
FIG. 1(b) (Prior Art)
Figure 2A:
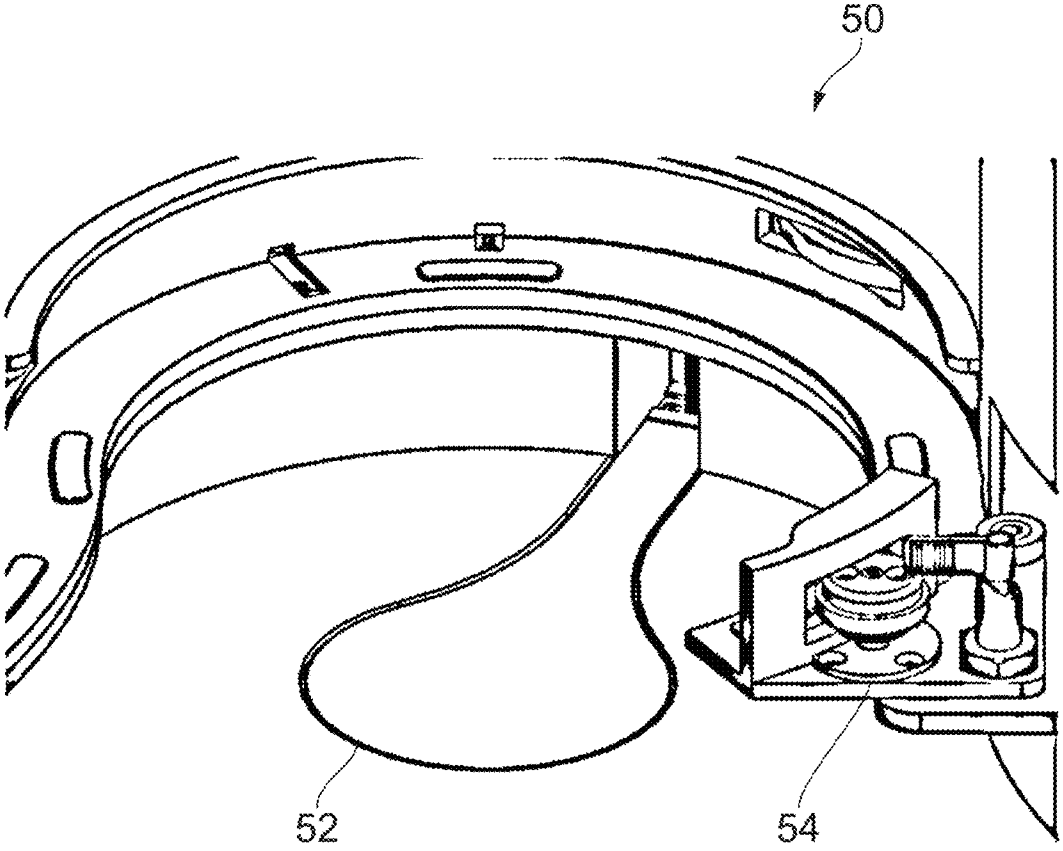
FIG. 2(a) (Prior Art)
FIGS. 2(*a*) to 2(*d*) illustrate an example of the prior art.
Figure 2B:
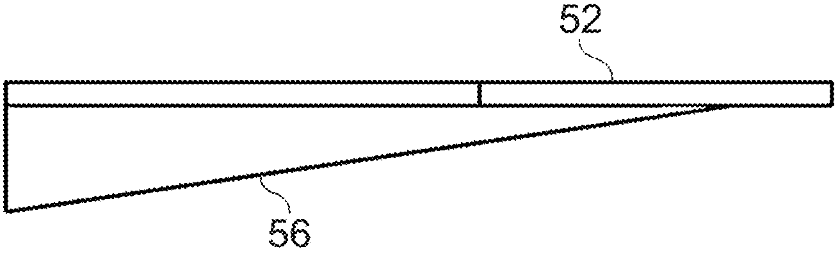
FIG. 2(b) (Prior Art)
Figure 2C:
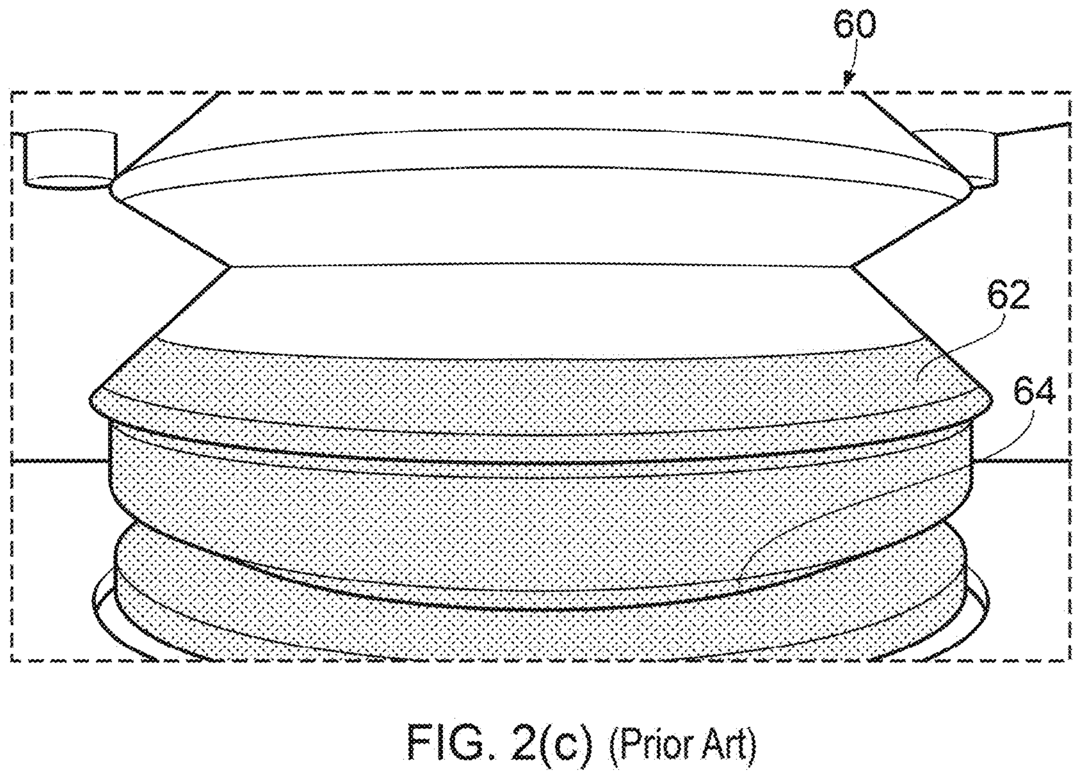
FIG. 2(c) (Prior Art)
Figure 2D:
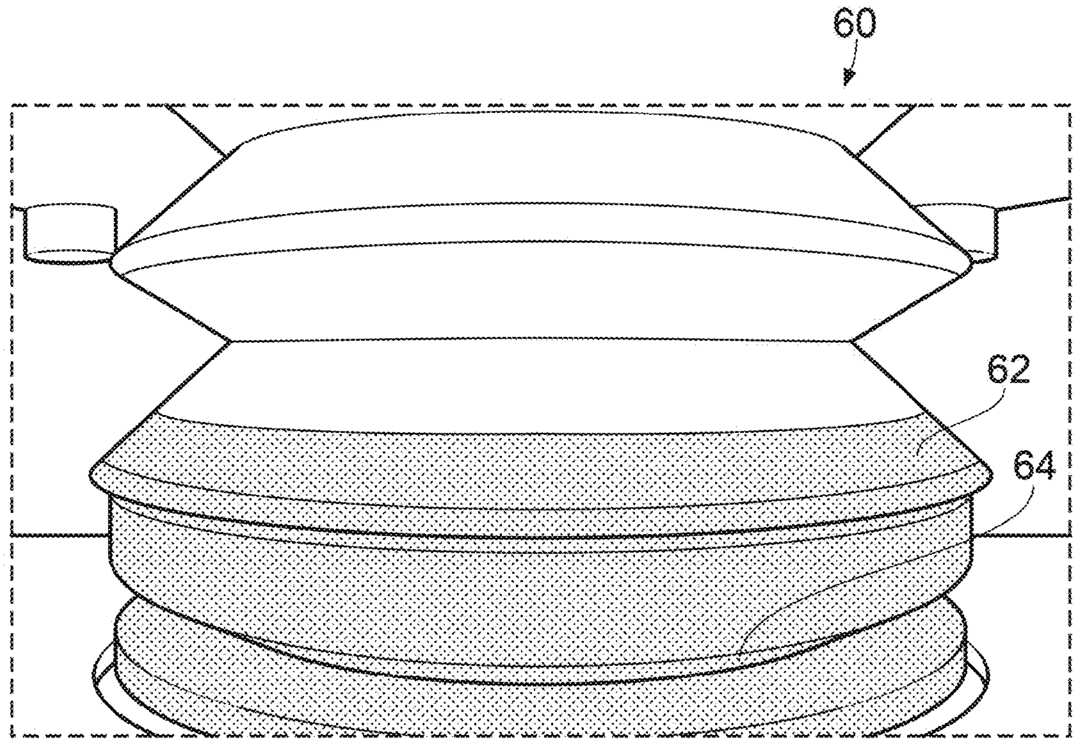
FIG. 2(d) (Prior Art)

The described example embodiment relates to an apparatus, a system and a method. They primarily relate to processes in cell and/or gene therapy but are not limited thereto.

Certain terminology is used in the following description for convenience only and is not limiting. The words "upper," "lower," "upwardly" and "downwardly" designate directions in the drawings to which reference is made and are with respect to the described component when assembled and mounted. The words "inner," "inwardly" and "outer," "outwardly" refer to directions toward and away from, respectively, a designated centerline or a geometric center of an element being described (e.g., a central axis), the particular meaning being readily apparent from the context of the description. Further, the terms "proximal" (i.e., nearer to) and "distal" (i.e., away from) designate positions relative to a body or a point of attachment.

Further, as used herein, the terms "connected," "affixed" and the like are intended to include direct connections between two members without any other members interposed therebetween, as well as, indirect connections between members in which one or more other members are interposed therebetween. The terminology includes the words specifically mentioned above, derivatives thereof, and words of similar import.

Further, unless otherwise specified, the use of ordinal adjectives, such as, "first," "second," "third" etc., merely indicate that different instances of like objects are being referred to and are not intended to imply that the objects so described must be in a given sequence, either temporally, spatially, in ranking or in any other manner. Like reference numerals are used to depict like features throughout.

Figure 3A:
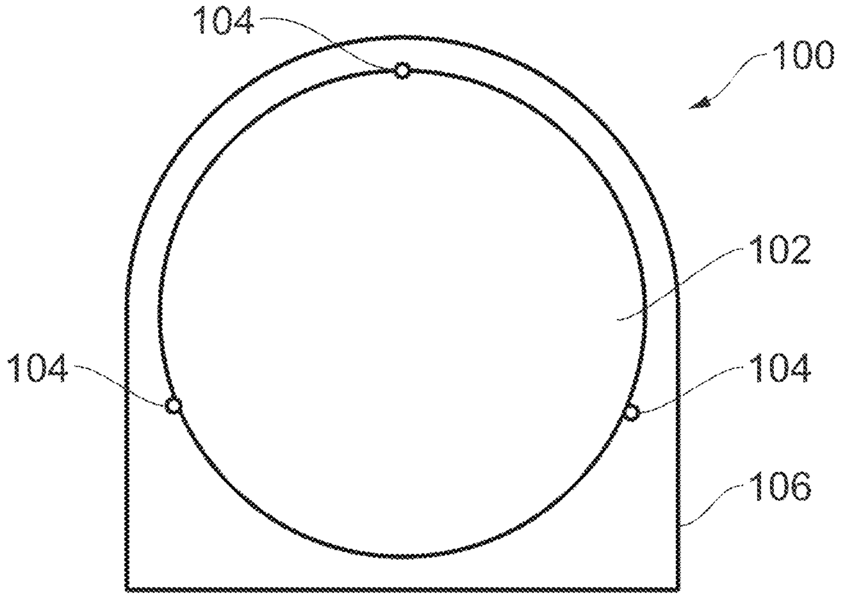
FIG. 3 illustrates (a) a top view, (b) a side view in a first configuration and (c) a side view in a second configuration of the apparatus according to one embodiment of the disclosure.
Figure 3B:
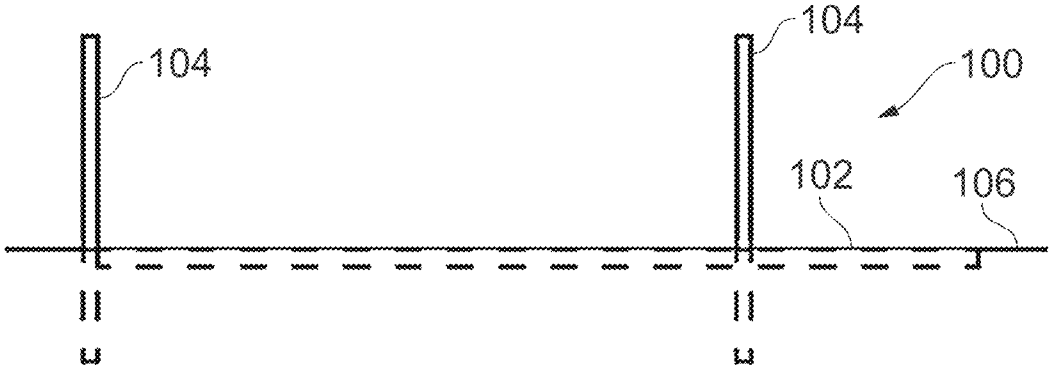
Figure 3C:
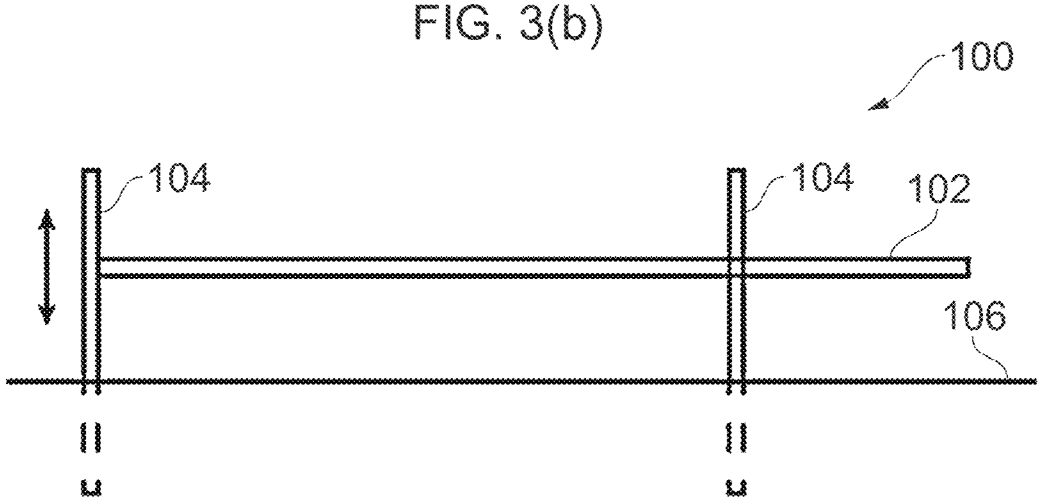

FIGS. 3(*a*) to 3(*c*) illustrate a first embodiment of an actuation mechanism 100 according to the disclosure. The actuation mechanism 100 includes a moveable plate 102 and a base plate 106. The moveable plate 102 is axially translatable by virtue of a plurality of linear actuators 104. The base plate 106 may also be rotatable about an axis by one or more actuators (not shown).

Figure 4:
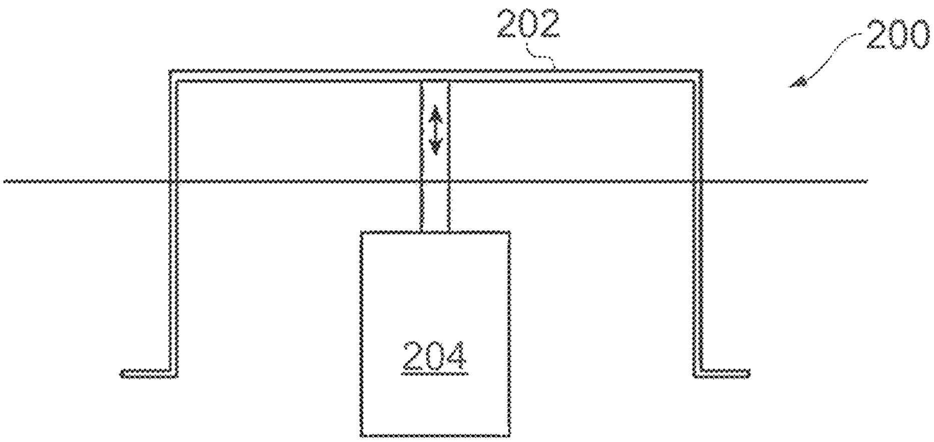
FIG. 4 illustrates a side view of the apparatus according to another embodiment of the disclosure.

FIG. 4 illustrates a second embodiment of an actuation mechanism 200. The actuation mechanism 200 includes a moveable plate 202 and a linear actuator 204. The linear actuator 204 acts upon a lower side, or surface, of the moveable plate 202 so as to raise and lower the moveable plate 202, in use.

Figure 5A:
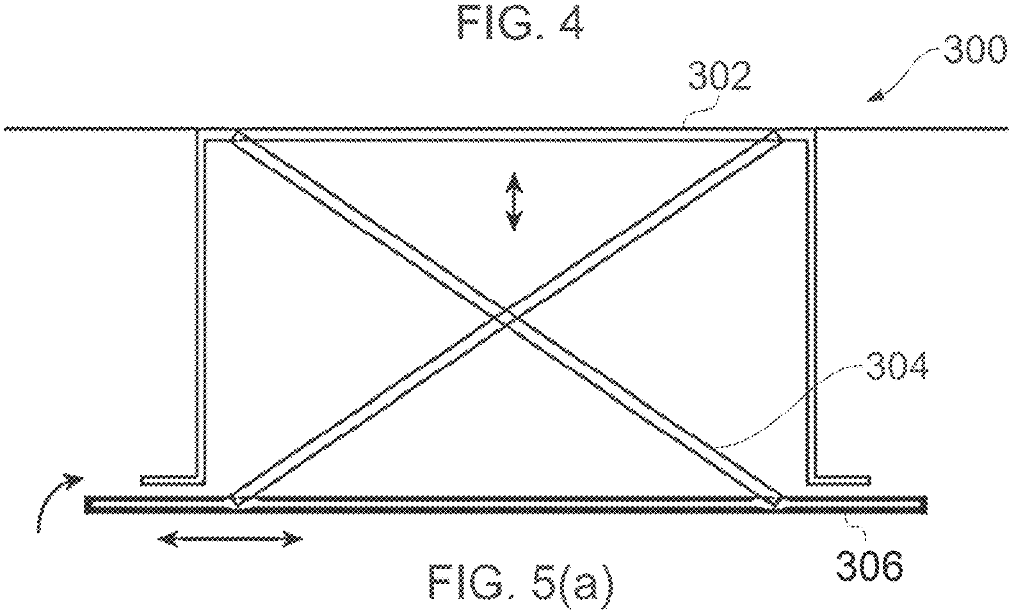
FIG. 5 illustrates (a) a side view in a first configuration and (b) a side view in a second configuration of the apparatus according to another embodiment of the disclosure.
Figure 5B:
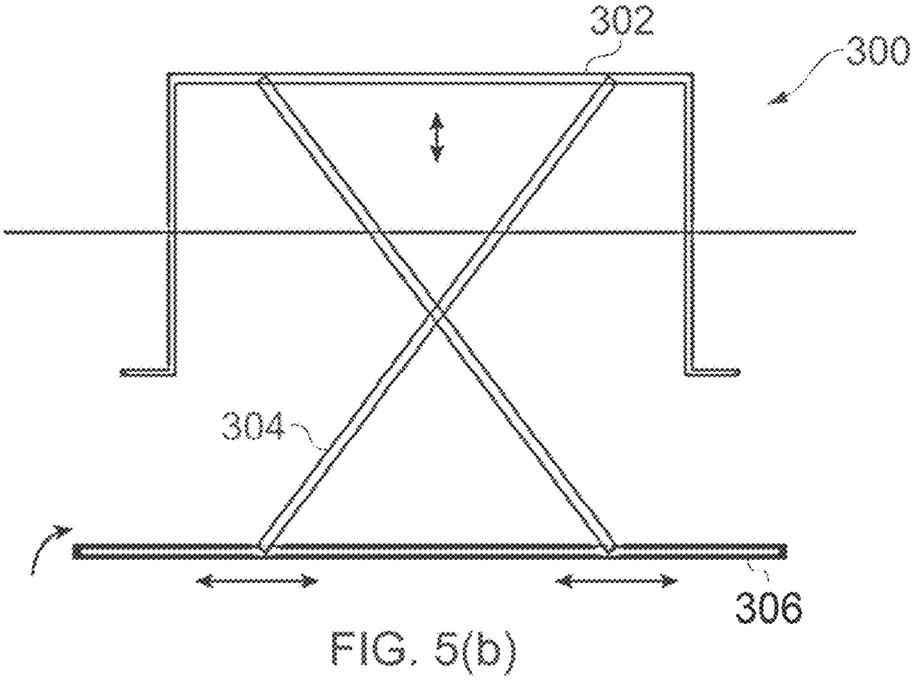

FIGS. 5(*a*) and 5(*b*) illustrate another embodiment of an actuation mechanism 300. The actuation mechanism 300 includes a moveable plate 302 and a base plate 306. The base plate 306 is connected to the moveable plate 302 by a linkage 304. The linkage 304 may be a series of pivotally connected rods, as shown in FIGS. 5(*a*) and 5(*b*). The actuation mechanism 300 may include one or more actuators (not shown) for raising or lowering the moveable plate 302, with respect to the base plate 306, in use. Furthermore, the actuation mechanism 300 may include one or more actuators (not shown) for rotating the base plate 306 about an axis, as indicated by the arced arrow in FIGS. 5(*a*) and 5(*b*). It is noted that there may be one or more actuators, which may both raise and lower the moveable plate 302, and rotate the base plate 306 about an axis.

Figure 6:
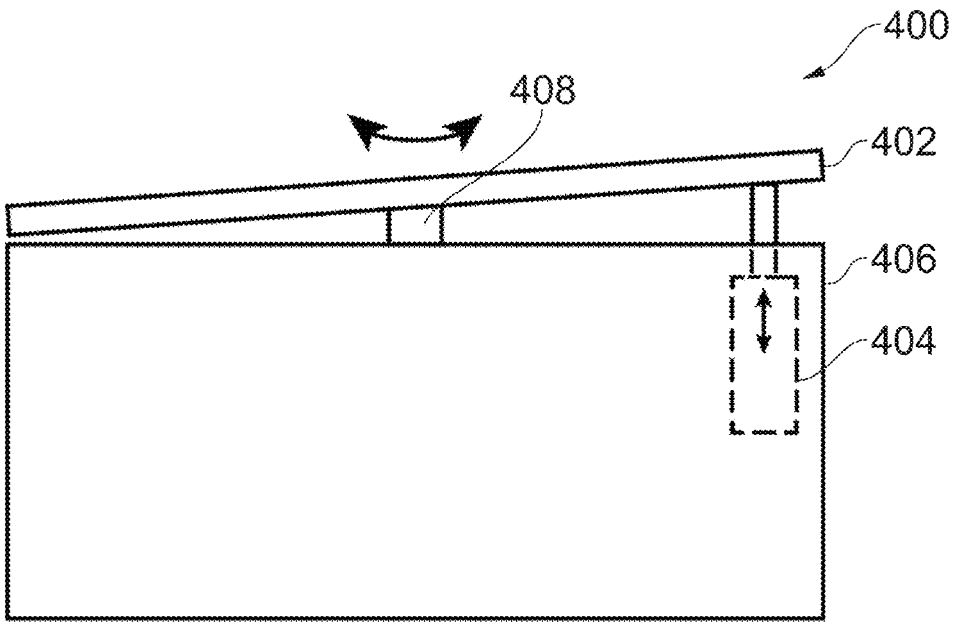
FIG. 6 illustrates a side view of the apparatus according to another embodiment of the disclosure.

FIG. 6 illustrates another embodiment of an actuation mechanism 400. The actuation mechanism 400 includes a moveable plate 402 and a base plate 406. The moveable plate 402 is connected to the base plate 406 by a pivotable rod 408. There is also provided a linear actuator 404, which acts upon the lower side, or surface, of the moveable plate 402. There may be any number of linear actuators 404. In the example where a number of linear actuators 404 are presented, when the linear actuators 404 act cooperatively, i.e., simultaneously, the moveable plate 402 is axially translated, that is raised or lowered. When the linear actuators 404 do not act cooperatively, i.e., not simultaneously, or out of timing, the moveable plate 402 is rocked along one or more axes, depending upon the number of linear actuators 404.

Figure 7:
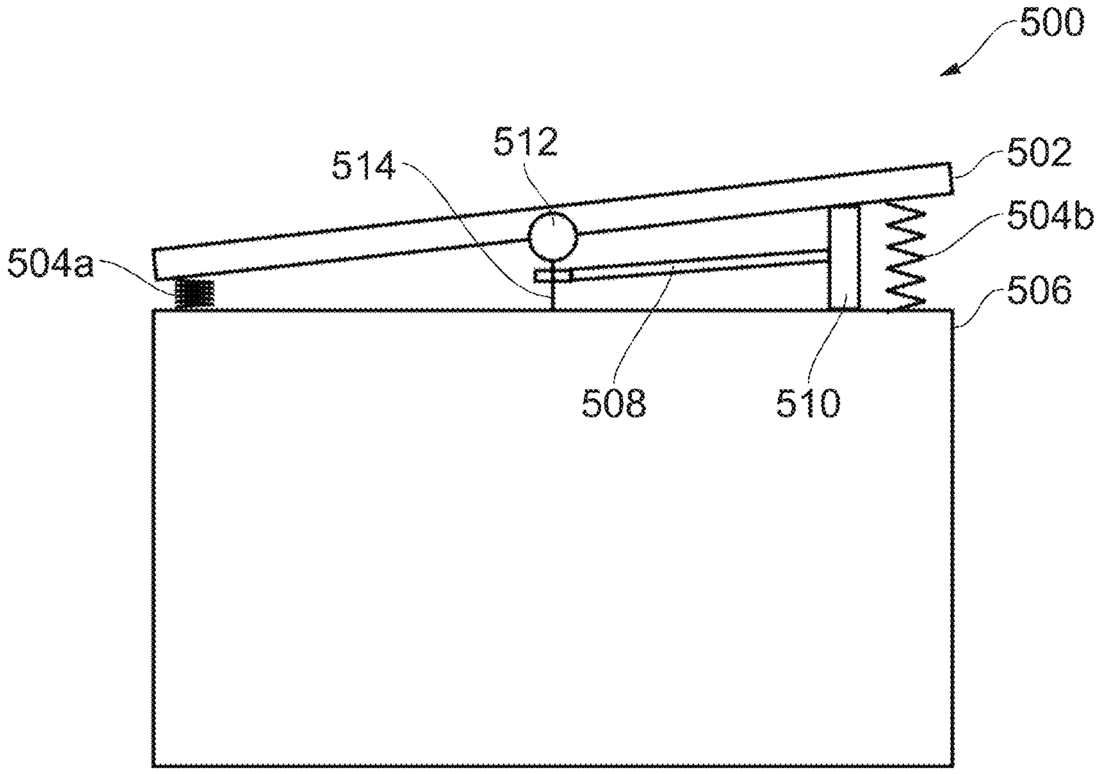
FIG. 7 illustrates a side view of the apparatus according to another embodiment of the disclosure.

FIG. 7 illustrates another embodiment of an actuation mechanism 500. The actuation mechanism 500 includes a moveable plate 502 and a base plate 506. The moveable plate 502 and the base plate 506 are connected by a central rod 514 extending axially from the base plate 506 toward a pivot point 512 of the moveable plate 502. There is also provided a series of springs 504*a*, 504*b*. Any number of springs 504*a*, 504*b* may be used. The springs 504*a*, 504*b* bias the moveable plate 502 toward the base plate 506. The springs 504*a*, 504*b* may be tension springs. Furthermore, there is provided a connecting rod 508, extending from the central rod 514 and terminating in a wheel 510. The central rod 514 may be driven by an actuator or a motor such that the wheel 510 is caused to rotate about the central rod 514. In this way, the moveable plate 502 is caused to rotate about two axes perpendicular to one another so as to provide a swirling motion of a container on the moveable plate 502.

Figure 8:
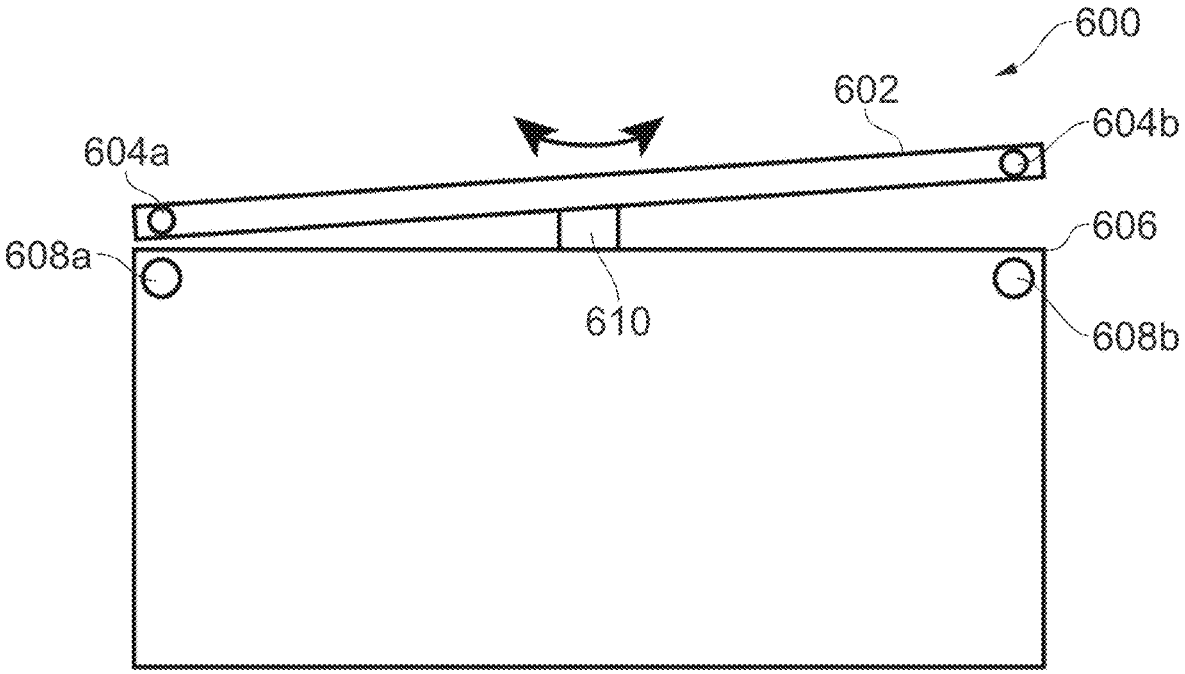
FIG. 8 illustrates a side view of the apparatus according to another embodiment of the disclosure.

FIG. 8 illustrates another embodiment of an actuation mechanism 600. The actuation mechanism 600 includes a moveable plate 602 and a base plate 606. The moveable plate 602 is connected to the base plate 606 by a pivotable rod 610. The base plate 606 is provided with electromagnets 608*a*, 608*b* on the outer edge. The moveable plate 602 is provided with permanent magnets 604*a*, 604*b* on the outer edge. The electromagnets 608*a* on the base plate 606 align with the permanent magnets 604*a* on the moveable plate 602. The electromagnets 608*b* on the base plate 606 align with the permanent magnets 604*b* on the moveable plate 602. In use, the electromagnets 608*a*, 608*b* are turned on and off sequentially such that the electromagnets 608*a*, 608*b* sequentially attract and repel the permanent magnets 604*a*, 604*b* on the moveable plate 602. The interaction between the electromagnets 608*a*, 608*b* on the base plate 606 and the permanent magnets 604*a*, 604*b* on the moveable plate 602 cause the moveable plate 602 to pivot about the pivotable rod 610. In some examples, the magnetic forces acting on the moveable plate 602 cause the moveable plate 602 to move about the base plate 606 in a wave motion.

Figure 9:
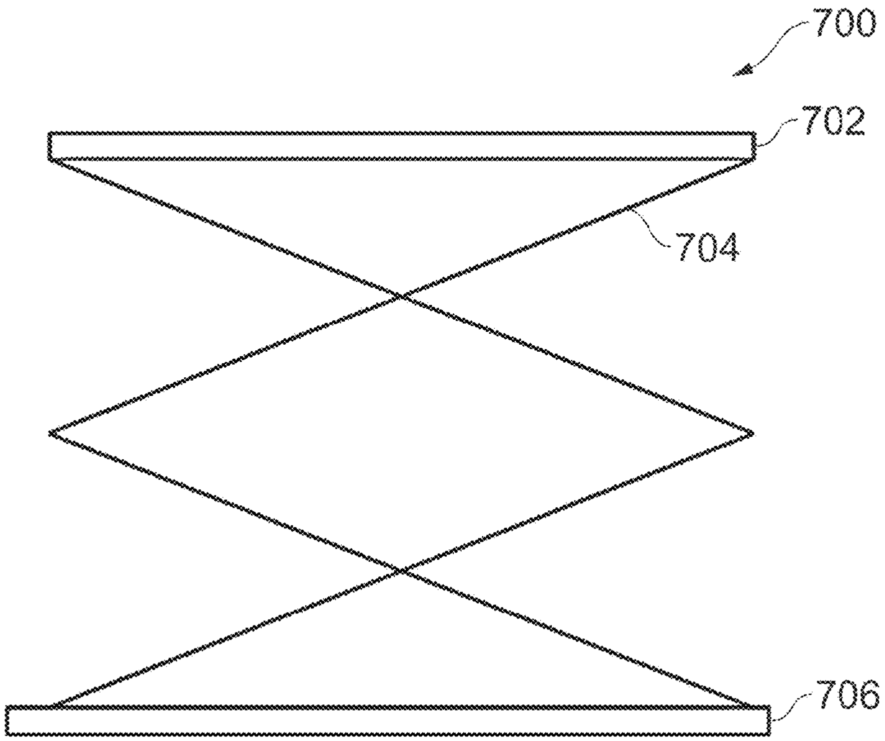
FIG. 9 illustrates a side view of the apparatus according to another embodiment of the disclosure.
Figure 10A:
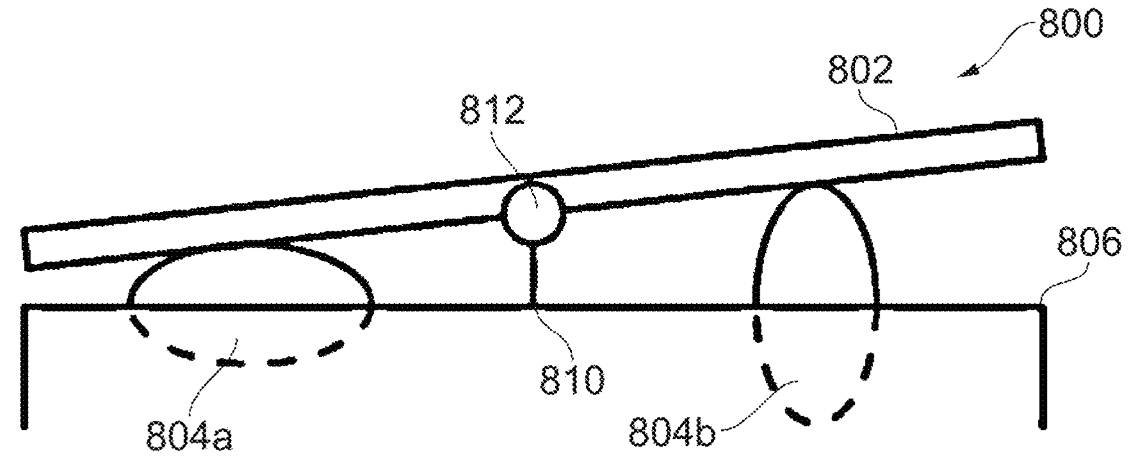
FIG. 10 illustrates (a) a first side view, (b) a second side view and (c) the first side view having the central hub removed of the apparatus according to another embodiment of the disclosure, and (d) one example of a cam member and (e) another example of a cam member for use in the apparatus of FIGS. 10(*a*) to 10(*c*)
Figure 10B:
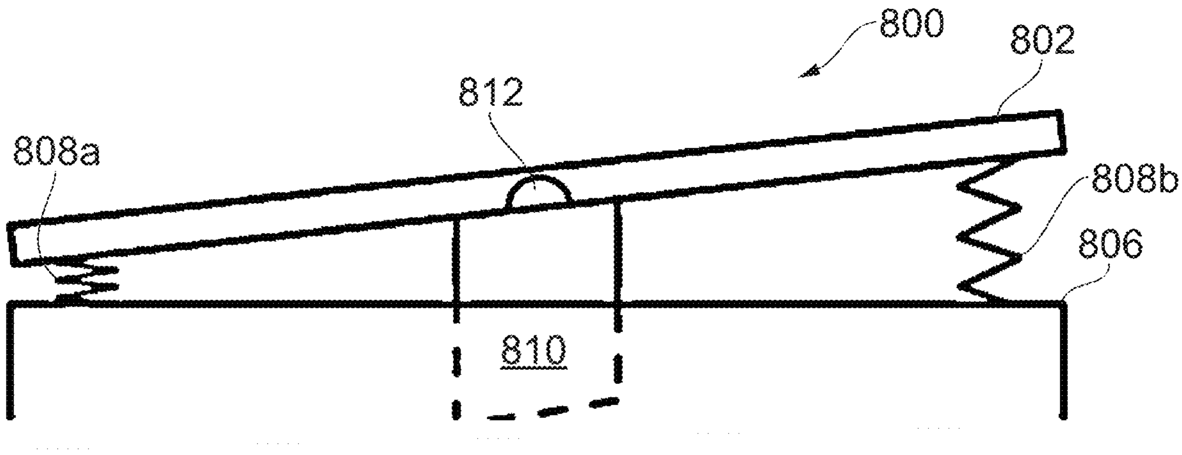
Figure 10C:
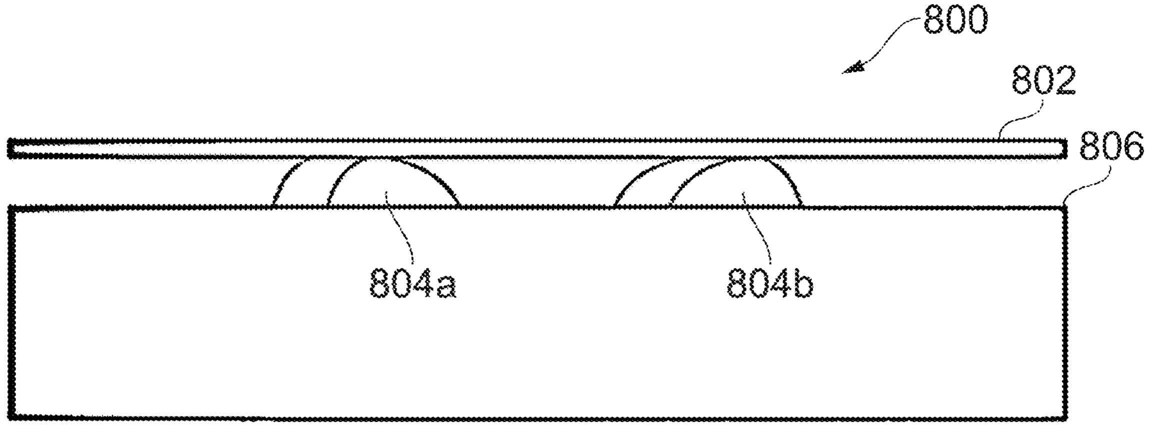
Figure 10D:
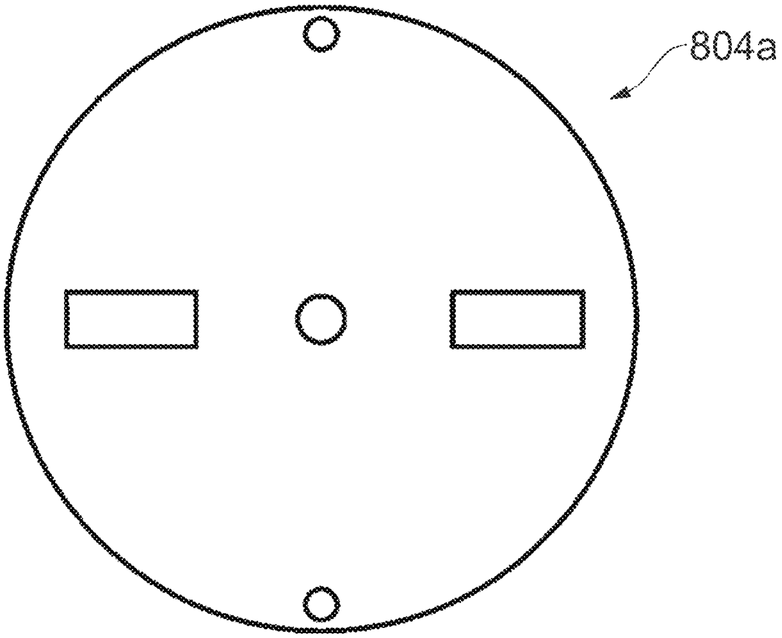
Figure 10E:
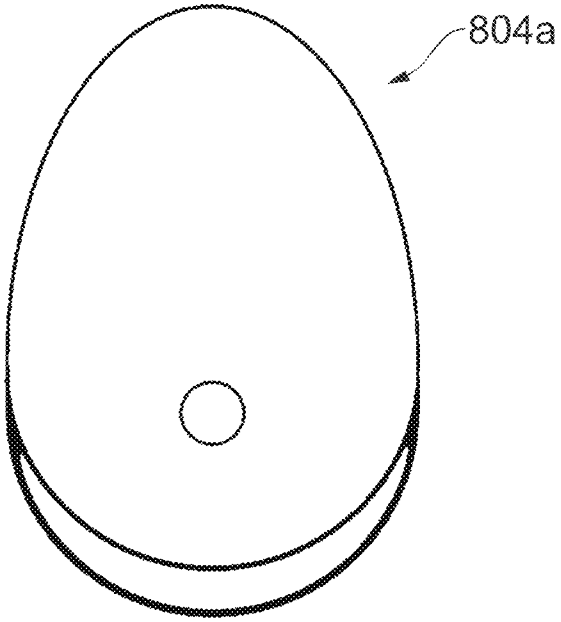

FIG. 9 illustrates another embodiment of an actuation mechanism 700. The actuation mechanism 700 includes a moveable plate 702 and a base plate 706. The base plate 706 is connected to the moveable plate 702 by a linkage 704. The linkage 704 is a series of pivotally connected rods, arranged in a scissor lift configuration. The actuation mechanism 700 may be provided with one or more actuators (not shown) that raise and lower the moveable plate 702, with respect to the base plate 706, in use. That is, the distance between the base plate 706 and the moveable plate 702 may be changed by raising and lowering the moveable plate 702, with respect to the base plate 706 by use of the one or more actuators.

FIGS. 10(*a*) to 10(*e*) illustrate another embodiment of an actuation mechanism 800. The actuation mechanism 800 includes a moveable plate 802 and a base plate 806. The base plate 806 is connected to the moveable plate 802 by a central rod 810 extending axially from the base plate 806 toward a pivot point 812 of the moveable plate 802. A first cam member 804*a* is provided on the base plate 806 and in contact with the moveable plate 802. A second cam member 804*b* is provided on an opposite side of the central rod 810, distal the first cam member 804*a*. The first cam member 804*a* is driven by one or more motors (not shown). The second cam member 804*b* is driven by one or more motors (not shown). The first cam member 804*a* is driven by the one or more motors to rotate about its pivotal axis. The second cam member 804*b* is driven by the one or more motors to rotate about its pivotal axis. In use, the first cam member 804*a* is driven such that a surface thereof engages the moveable plate 802 such that the moveable plate 802 moves about the pivot point 812. The second cam member 804*b* may be driven either instead of or in addition to the first cam member 804*a* such that a surface thereof engages the moveable plate 802 such that the moveable plate 802 moves about the pivot point 812. The first cam member 804*a* may be driven independently of the second cam member 804*b*.

In some examples, the first cam member 804*a* and the second cam member 804*b* are driven simultaneously. The cam members 804*a*, 804*b* may have a non-circular profile such that the moveable plate 802 moves non-linearly. As shown in this particular example, the first cam member 804*a* is arranged to rotate out of phase in respect of the second cam member 804*b* in order to raise one side of the moveable plate 802 and lower the other side of the moveable plate 802. As will be described, the cam members 804*a*, 804*b* may be provided with an angled surface or a non-circular profile, to tilt the moveable plate 802 from one side to the other during use. Examples of the cam members 804*a*, 804*b* are illustrated in FIGS. 10(*d*) and 10(*e*). FIG. 10(*d*) shows a cam member 804*a* having a circular profile. FIG. 10(*e*) shows a cam member 804*a* having an elongated circular profile. As shown in FIG. 10(*b*), the cam members 804*a*, 804*b* may additionally be provided with tension springs 808*a*, 808*b* that provides a resilient force between the base plate 806 and the moveable plate 802. FIG. 10(*c*) illustrates an example in use, where the first cam member 804*a* and the 804*b* are mirrored with respect to each other. The upper surface of the cam members 804, 804*b* are level such that the moveable plate 802 positioned horizontally.

Figure 11:
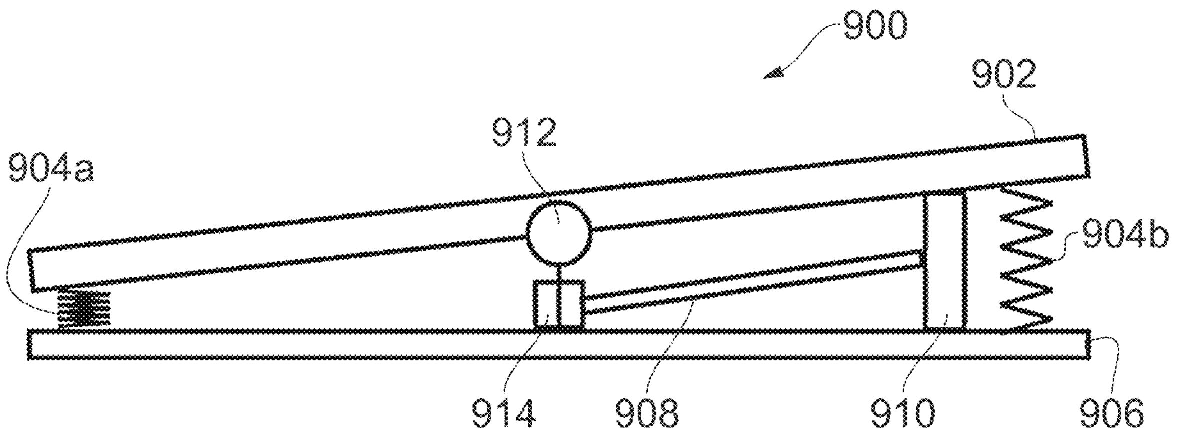
FIG. 11 illustrates a side view of the apparatus according to another embodiment of the disclosure.

FIG. 11 illustrates another embodiment of an actuation mechanism 900. The actuation mechanism 900 includes a moveable plate 902 and a base plate 906. The moveable plate 902 and the base plate 906 are connected by a central hub 914 extending axially from the base plate 906 toward a pivot point 912 of the moveable plate 902. A series of springs 904*a*, 904*b* are provided. Any number of springs 904*a*, 904*b* may be used. The springs 904*a*, 904*b* bias the moveable plate 902 toward the base plate 906. In this example, the springs 904*a*, 904*b* are tension springs. A connecting rod 908 is provided, extending radially from the central hub 914 and terminating in a wheel 910. The central hub 914 may be driven by an actuator or a motor such that the wheel 910 is caused to rotated about the central hub 914. In this way, the moveable plate 902 is caused to rotate about two axes perpendicular to one another so as to provide a swirling motion of a container on the moveable plate 902. In some examples, the wheel 910 is driven by a motor and moves around in a circular motion. This moves the moveable plate 902 in a symmetrical wave motion.

Figure 12:
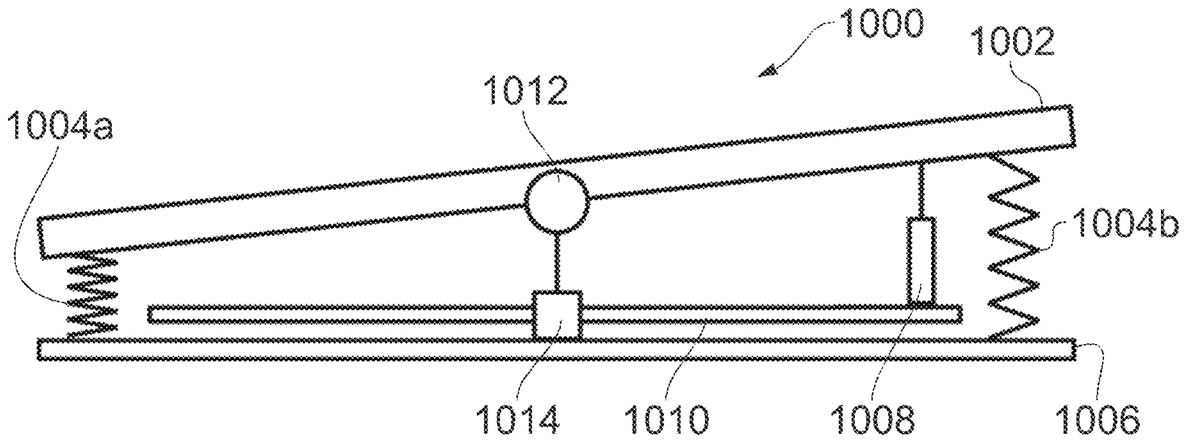
FIG. 12 illustrates a side view of the apparatus according to another embodiment of the disclosure.

FIG. 12 illustrates another embodiment of an actuation mechanism 1000. The actuation mechanism 1000 includes a moveable plate 1002 and a base plate 1006. The moveable plate 102 and the base plate 1006 are connected by a central hub 1014 that extends axially from the base plate 1006 toward a pivot point 1012 of the moveable plate 1002. Springs 1004*a*, 1004*b* are provided to bias the moveable plate 1002 toward the base plate 1006. In this embodiment, a central hub 1014 is provided on the base plate 1006. The central hub 1014 is coupled to a support plate 1010. A linear actuator 1008 is provided between the support plate 1010 and the base plate 1006. The linear actuator 1008 acts upon a lower side, or surface, of the moveable plate 1002 so as to raise and lower the moveable plate 1002, in use. The support plate 1010 may be rotationally driven by a motor (not shown).

Figure 13A:
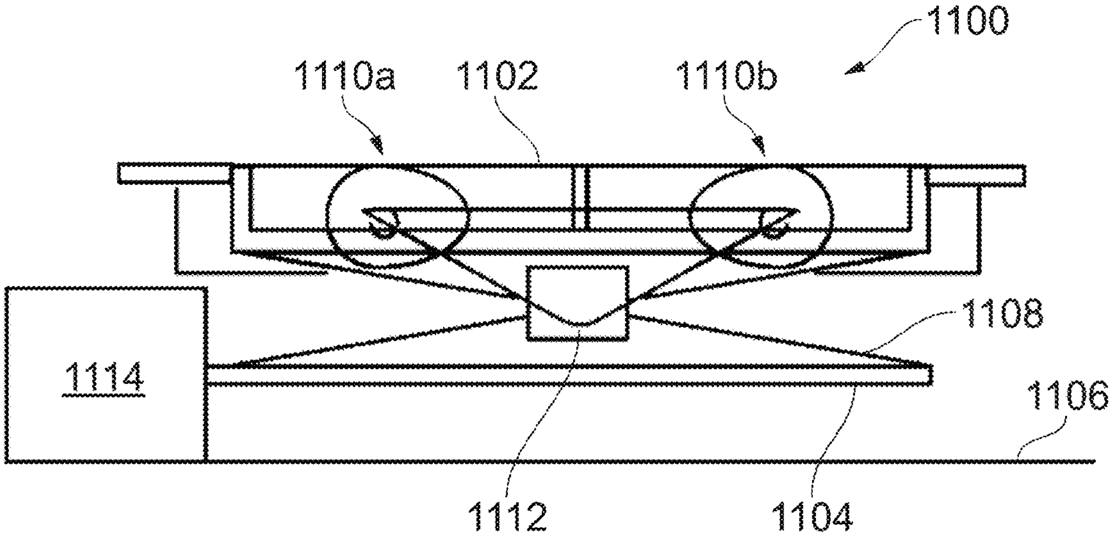
FIG. 13 illustrates (a) a side view in a first configuration, (b) a side view in a second configuration and (c) an enlarged view of the apparatus according to another embodiment of the disclosure.
Figure 13B:
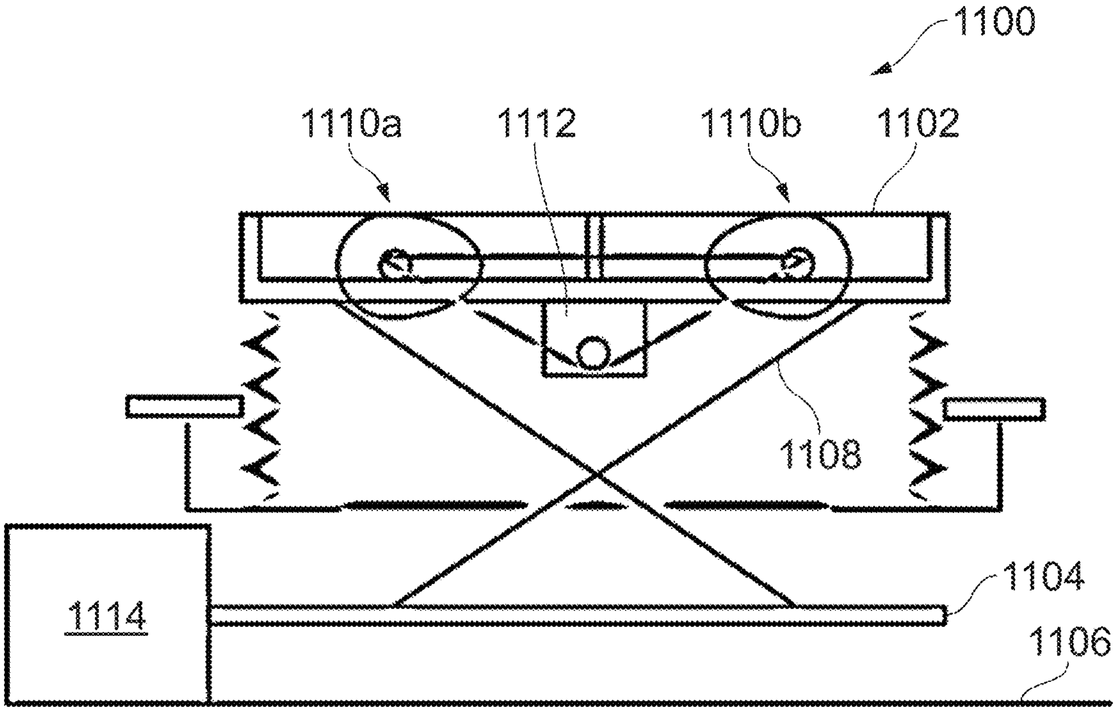
Figure 13C:
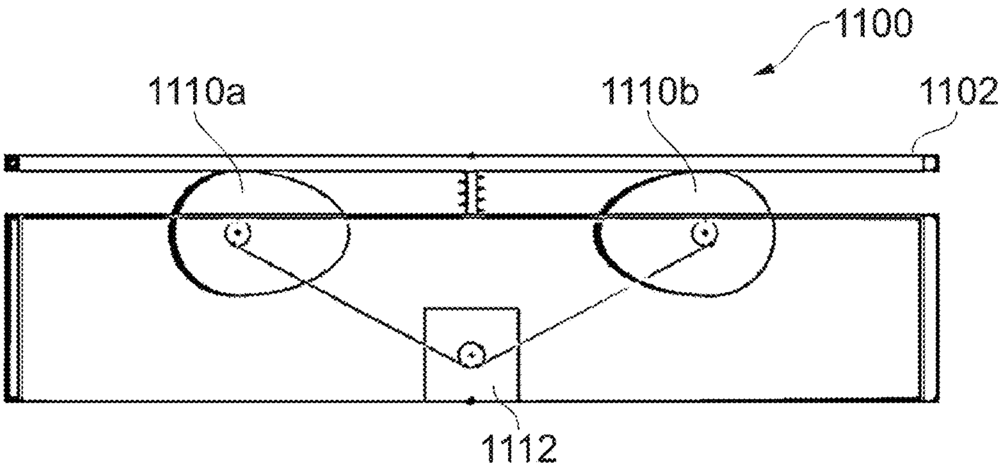

FIGS. 13(*a*) and 13(*b*) illustrate another embodiment of an actuation mechanism 1100. The actuation mechanism 1100 includes a moveable plate 1102 and a base plate 1106. A motor 1114 is positioned on the base plate 1106 and is operably coupled to a support plate 1104. The support plate 1104 is positioned between the base plate 1106 and the moveable plate 1102. The motor 1114 operates to rotate the support plate 1104, with respect to the base plate 1106. In some examples, the motor 1114 is raised and lowered with respect to the base plate 1106. The support plate 1104 is connected to the moveable plate 1102 by a linkage 1108. The linkage 1108 may be a series of pivotally connected rods. The linkage 1108 may be enclosed by a housing, such as a bellows-based housing, so as to prevent access to the linkage 1108 during use. The actuation mechanism 1100 includes an actuator 1112 for raising or lowering the moveable plate 1102, with respect to the support plate 1104, in use. In this particular embodiment, a cam system is provided. The cam system has a first cam member 1110*a* and a second cam member 1110*b*. The cam members 1110*a*, 1110*b* are integrated with the linkages 1108 in this example. However, the cam members 1110*a*, 1110*b* may in addition or instead be integrated with the actuator 1112. The cam members 1110*a*, 1110*b* are drive such that a surface thereof engages the moveable plate 1102. This moves the moveable plate 1102 with respect to the base plate 1106.

Figure 14A:
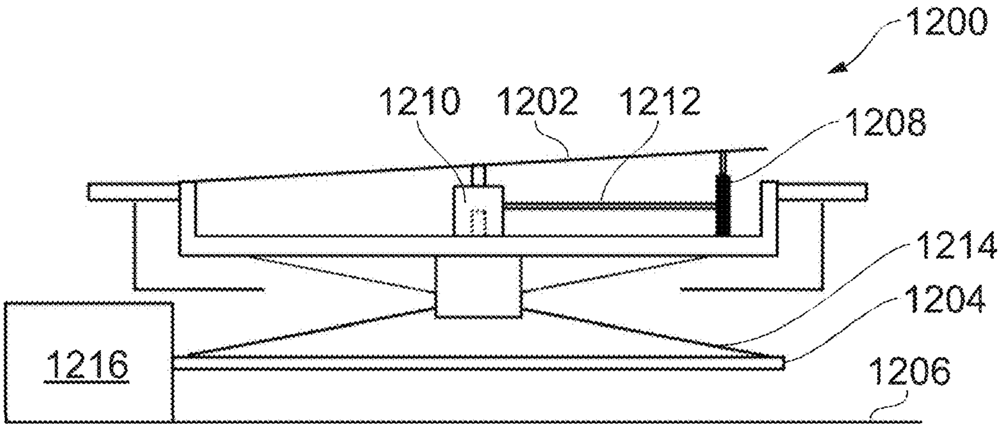
FIG. 14 illustrates (a) a side view in a first configuration and (b) a side view in a second configuration of the apparatus according to another embodiment of the disclosure.
Figure 14B:
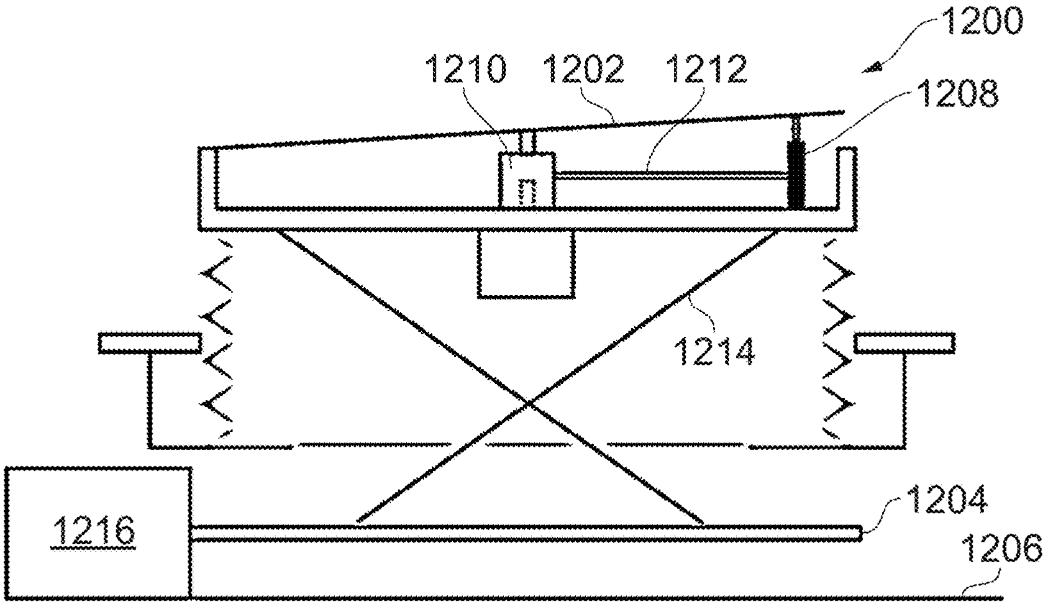

FIGS. 14(*a*) and 14(*b*) illustrate another embodiment of an actuation mechanism 1200. The actuation mechanism 1200 includes a moveable plate 1202 and a base plate 1206.

A motor 1216 is positioned on the base plate 1206 and is operably coupled to a support plate 1204. The support plate 1204 is positioned between the base plate 1206 and the moveable plate 1202. The motor 1216 operates to rotate the support plate 1204, with respect to the base plate 1206. In some examples, the motor 1216 is raised and lowered with respect to the base plate 1206. The support plate 1204 is connected to the moveable plate 1202 by a linkage 1214. The linkage 1214 may be enclosed by a housing, such as a bellows-based housing, so as to prevent access to the linkage 1214 during use. The linkage 1214 may be a series of pivotally connected rods. In use, the linkage 1214 moves the moveable plate 1202 with respect to the support plate 1204, and thus the base plate 1206. In this particular embodiment, the actuation mechanism 1200 includes a central hub 1210 extending axially toward the moveable plate 1202. Moreover, there is provided a connecting rod 1212, extending radially from the central hub 1210 and terminating in a linear actuator 1208. In use, the central hub 1210 is driven by an actuator or a motor (not shown) such that the linear actuator 1208 is caused to be driven to provide a swirling motion, once the linear actuator 1208 is actuated, for a container placed on top of the moveable plate 1202.

Figure 15:
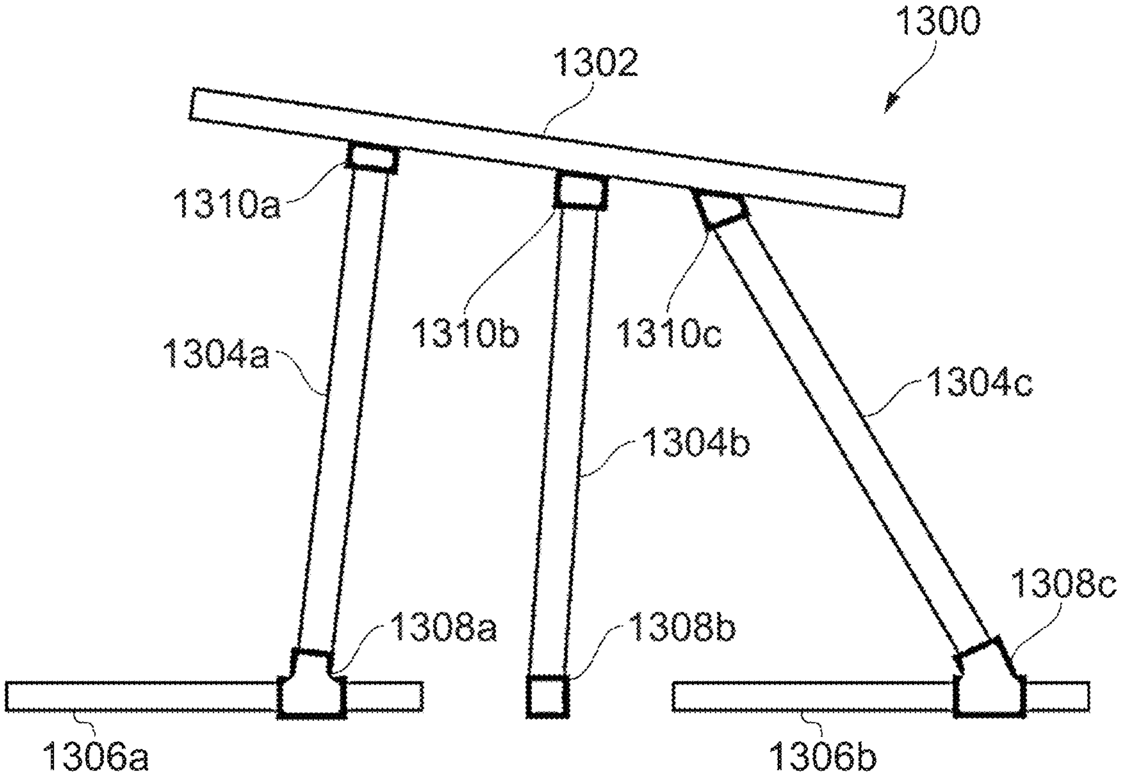
FIG. 15 illustrates a side view of the apparatus according to another embodiment of the disclosure.

FIG. 15 illustrates another embodiment of an actuation mechanism 1300. The actuation mechanism 1300 includes a moveable plate 1302 and three linkages: a first linkage 1304*a*, a second linkage 1304*b* and a third linkage 1304*c*. The linkages 1304*a*, 1304*b*, 1304*c* extend from the bottom surface of the moveable plate 1302. The first linkage 1304*a* extends from the moveable plate 1302 at a first pivot point 1310*a* toward a base plate 1306*a*. The second linkage 1304*b* extends from the moveable plate 1302 at a second pivot point 1310*b* toward a base plate (not shown). The third linkage 1304*c* extends from the moveable plate 1302 at a third pivot point 1310*c* toward a base plate 1306*b*. A first actuator 1308*a* is positioned between the first linkage 1304*a* and the base plate 1306*a*. A second actuator 1308*b* is positioned between the second linkage 1304*b* and the base plate (not shown). A third actuator 1308*c* is positioned between the third linkage 1304*c* and the base plate 1306*b*. In use, the actuators 1308*a*, 1308*b*, 1308*c* are driven sinusoidally out of phase from each other to produce a wave effect on the moveable plate 1302. In some examples, the actuators 1308*a*, 1308*b*, 1308*c* are linear actuators that slide along rails such that the pivot points move in synchronization to move the moveable plate 1302 in a wave motion.

Figure 16A:
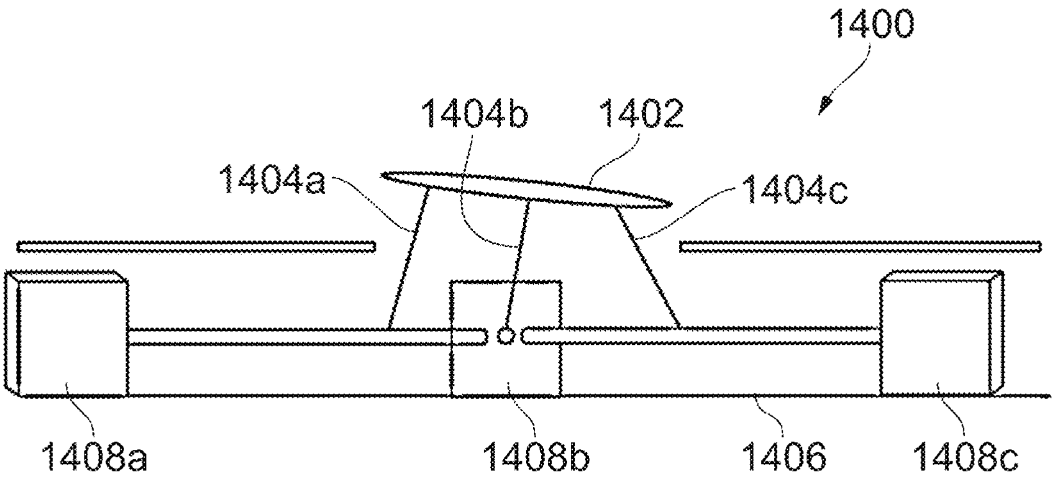
FIG. 16 illustrates (a) a side view, (b) a perspective view and (c) another perspective view including a container, of the apparatus according to another embodiment of the disclosure.
Figure 16B:
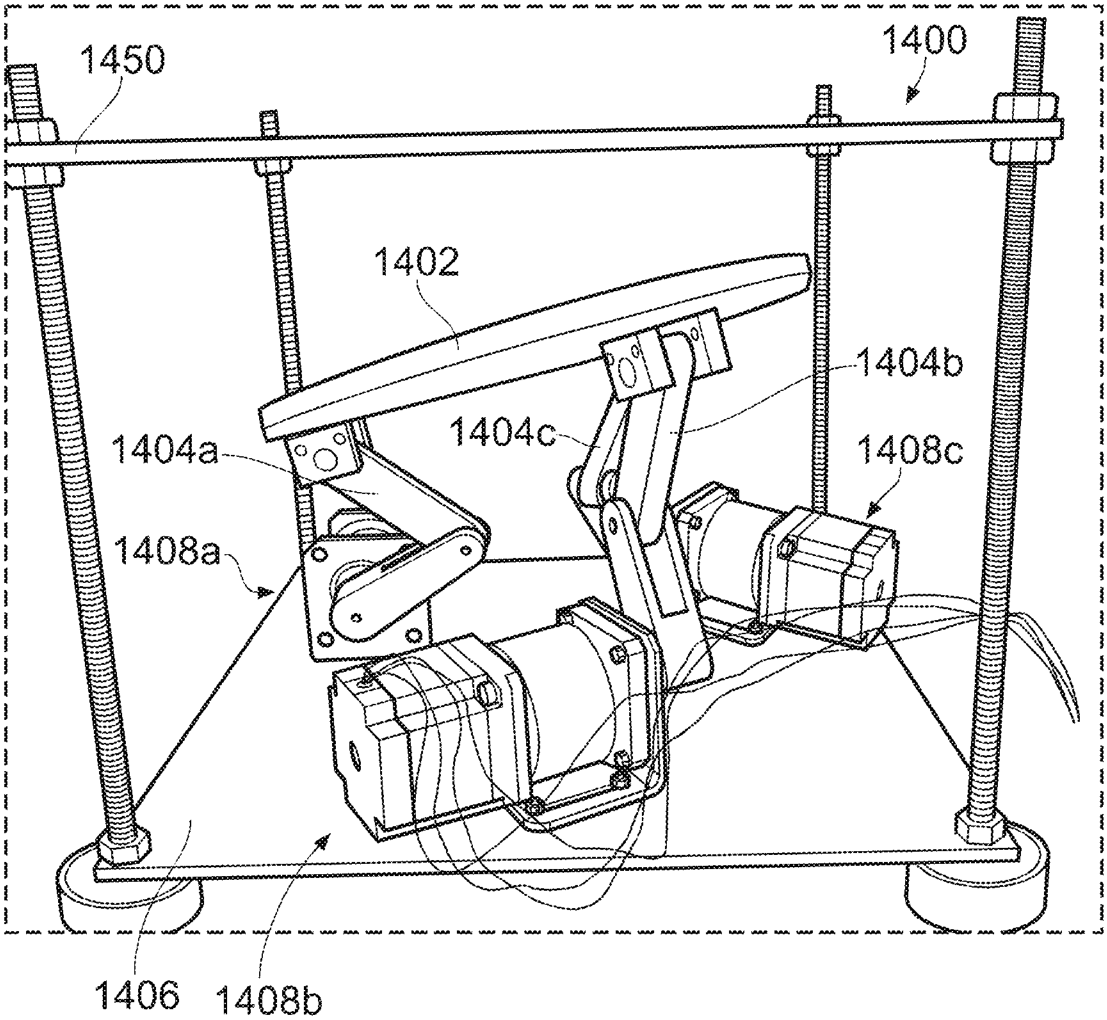
Figure 16C:
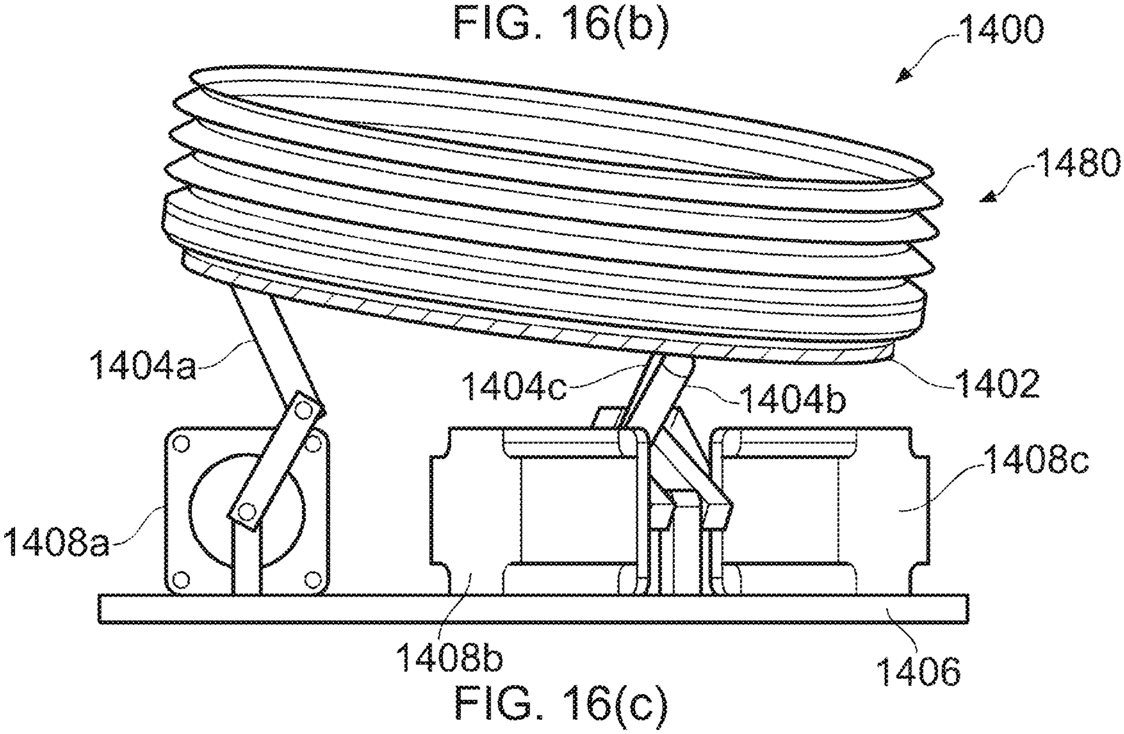

FIG. 16(*a*) illustrates another embodiment of an actuation mechanism 1400. The actuation mechanism 1400 has a moveable plate 1402 and a base plate 1406. In this particular embodiment, three motors 1408*a*, 1408*b*, 1408*c* are provided. Three linkages: a first linkage 1404*a*, a second linkage 1404*b* and a third linkage 1404*c*, are also provided extending from the moveable plate 1402. The motors 1408*a*, 1408*b*, 1408*c* are each used to drive a respective linkage 1404*a*, 1404*b*, 1404*c*. More specifically, a first motor 1408*a* drives a first linkage 1404*a*. A second motor 1408*b* drives a second linkage 1404*b*. A third motor 1408*c* drives a third linkage 1404*c*. The linkages 1404*a*, 1404*b*, 1404*c* are driven in coordination to move the moveable plate 1402 in a wave motion. Referring to FIGS. 16(*b*) and 16(*c*), a holding element 1450 is provided. A container 1480 having a base section is provided. The container 1480 will be described in more detail with reference to the later drawings.

In particular, it is noted that the apparatus includes the actuation mechanism 1400, the moveable plate 1402 and the holding element 1450. A system further includes the container 1480.

More specifically, the base of the container 1480 is placed on top of the moveable plate 1402 such that the container 1480 is arranged between the holding element 1450 and the moveable plate 1402. The container 1480 has a compressible wall. When the moveable plate 1402 is moved using the aforementioned actuation mechanism 1400, the top of the container 1480 is caused to be pushed against the holding element 1450. This compresses the wall of the container 1480.

Figure 17A:
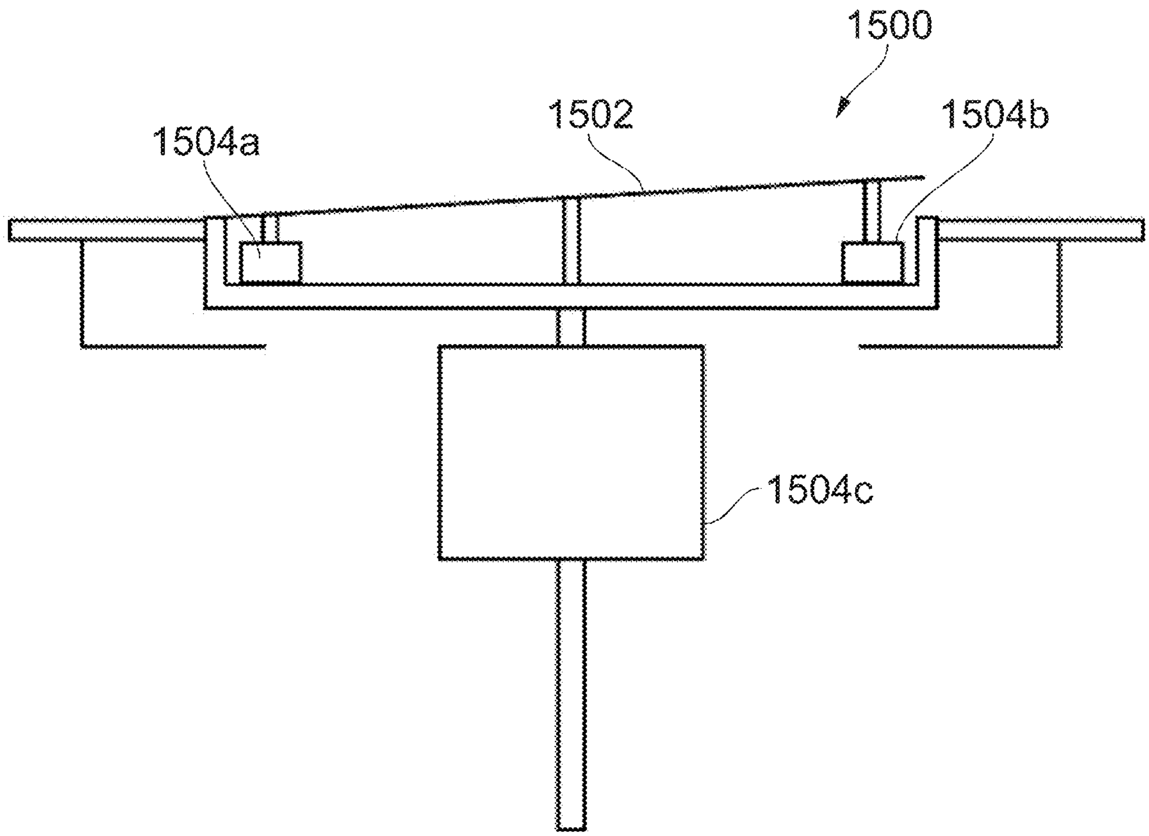
FIG. 17 illustrates (a) a side view in a first configuration and (b) a side view in a second configuration of the apparatus according to another embodiment of the disclosure.
Figure 17B:
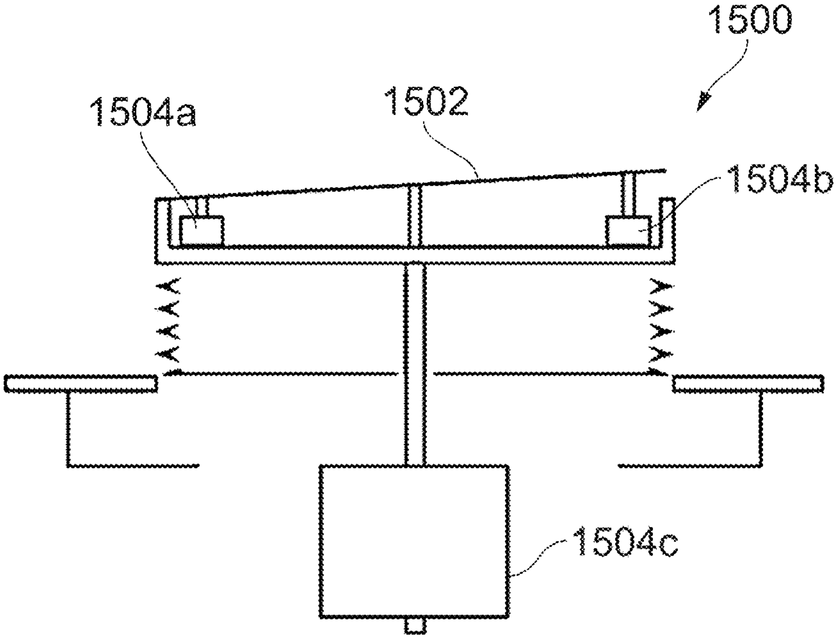
Figure 18A:
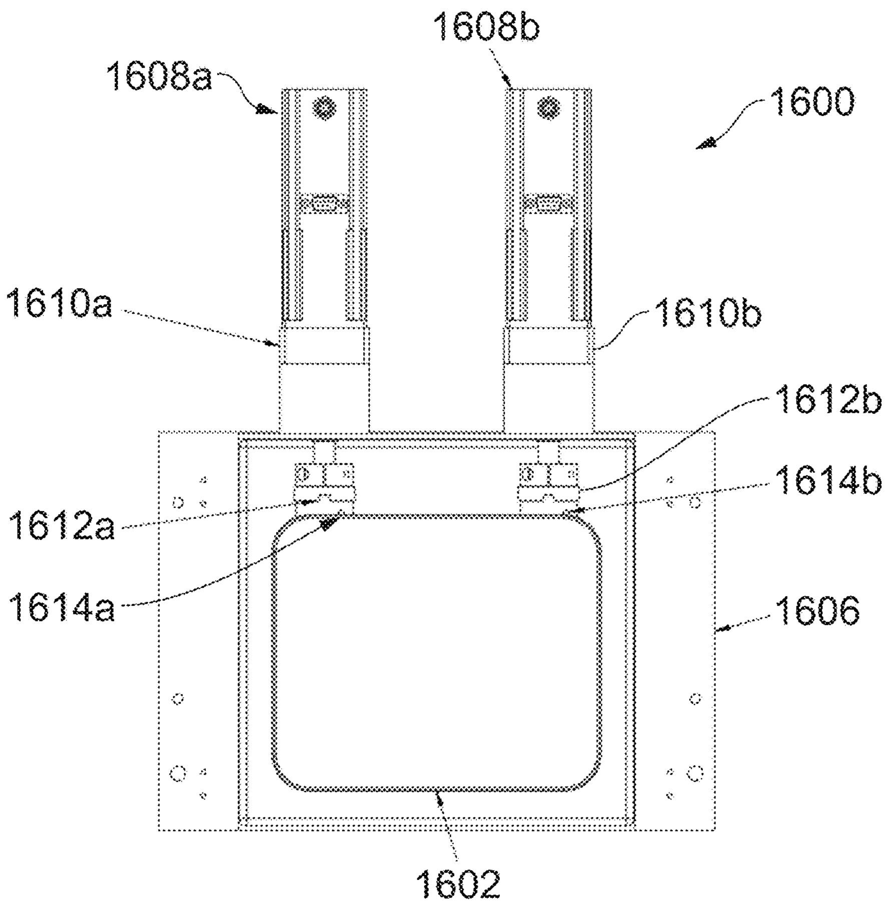
FIG. 18 illustrates (a) a top view, (b) a first side view, (c) a perspective view and (d) another side view of the apparatus according to another embodiment of the disclosure.
Figure 18B:
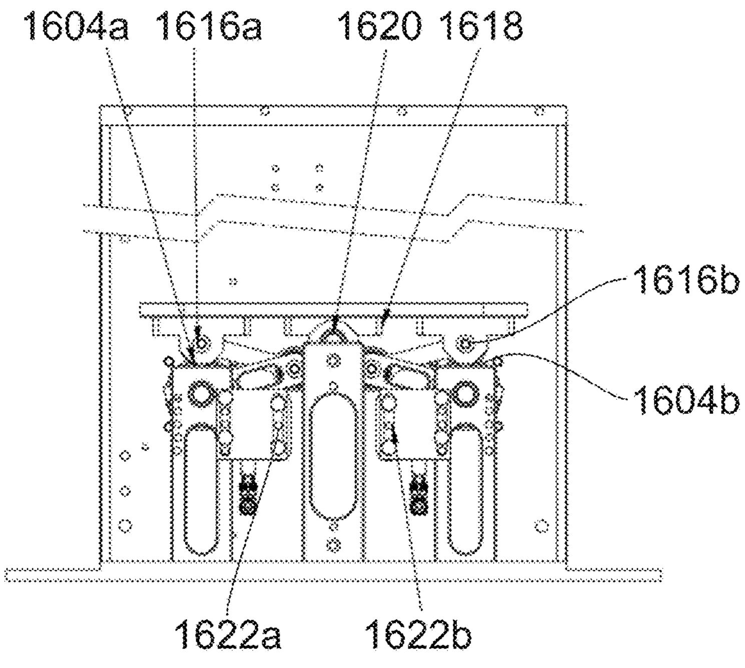
Figure 18C:
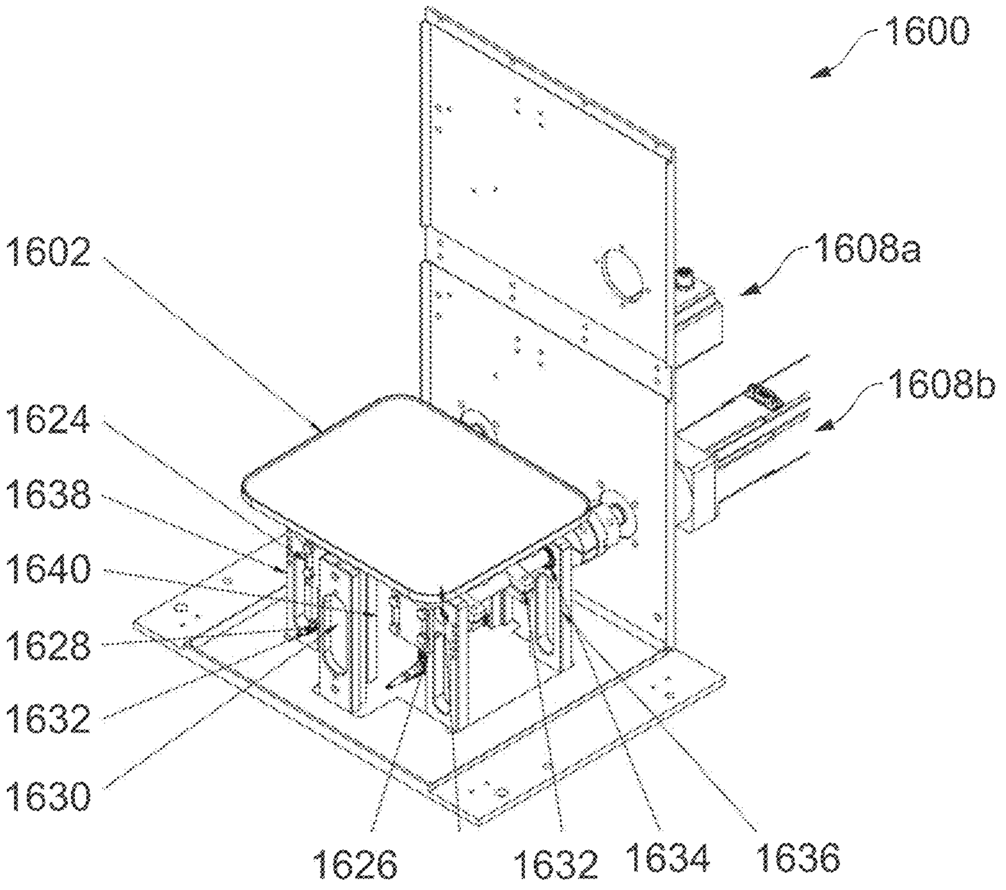
Figure 18D:
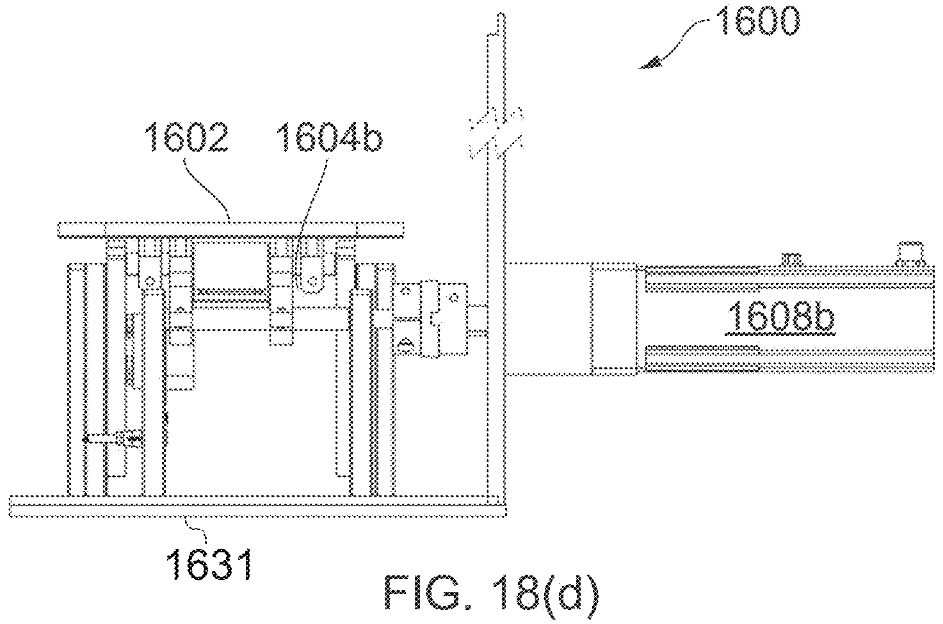

FIGS. 17(*a*) and 17(*b*) illustrate another embodiment of an actuation mechanism 1500. The actuation mechanism has a moveable plate 1502 and two linear actuators 1504*a*, 1504*b*. A first linear actuator 1504*a* is provided on a first side of the moveable plate 1502. A second linear actuator 1504*b* is provided on an opposite site of the moveable plate 1502. The linear actuators 1504*a*, 1504*b* are positioned to act upon the bottom surface of the moveable plate 1502. There may be any number of linear actuators 1504. When the linear actuators 1504 act cooperatively, i.e., simultaneously, the moveable plate 1502 is axially translated. When the linear actuators 1504 do not act cooperatively, i.e., not simultaneously, or out of timing, the moveable plate 1502 is rocked along one or more axes, depending upon the number of linear actuators 1504. In this particular embodiment, a further linear actuator 1504*c*, which is a larger linear actuator 1504*c* in this example, is provided at the bottom of the actuation mechanism, below the linear actuators 1504*a*, 1504*b*. In use, the larger linear actuator 1504*c* is provided to be raised from an upper position, shown in FIG. 17(*a*), to a lower position, shown in FIG. 17(*b*).

FIGS. 18(*a*) to 18(*d*) illustrate another apparatus 1600 according to the disclosure. The apparatus 1600 includes a moveable plate 1602 and a base plate 1606. The moveable plate 1602 and the base plate 1606 are operably coupled by a first linkage 1604*a* and a second linkage 1604*b*. The first linkage 1604*a* is driven by a first motor 1608*a*, connected to a first gearbox 1610*a* and to the first linkage 1604*a*. The second linkage 1604*b* is driven by a second motor 1608*b*, connected to a second gearbox 1610*b* and to the second linkage 1604*b*. Each motor 1608*a*, 1608*b*, specifically the gearboxes 1610*a*, 1610*b*, is coupled to a motor pivot shaft 1612*a*, 1612*b*, which is in turn coupled to a motor coupling 1614*a*, 1614*b* for driving the linkages 1604*a*, 1604*b*.

As best shown in FIG. 18(*b*), the first linkage 1604*a* is upstanding from the base plate 1606 and coupled to the moveable plate 1602 at one end. The second linkage 1604*b* is upstanding from the base plate 1606 and coupled to the moveable plate 1602 at another, opposing, end. Specifically, the first linkage 1604*a* includes a pivot bar 1616*a* connected to an underside surface of the moveable plate 1602. The second linkage 1604*b* also includes a pivot bar 1616*b* connected to an underside surface of the moveable plate 1602. The moveable plate 1602 is also connected to a central pivot clamp 1618, which is pivotable about a central pivot bar 1620. Furthermore, each linkage 1604*a*, 1604*b* includes a hard stop 1622*a*, 1622*b*, defining the lowest point, or the lowest plane, in which the moveable plate 1602 can reach.

Referring now to, in particular, FIG. 18(*c*), the apparatus 1600 further includes a mount for a sensor 1624, which can receive a sensor 1626 therein, the sensor 1626 including a sensor cable 1628. The sensor cable 1628 communicatively connects the sensor 1626 to a controller (not shown). The controller (not shown) may further be communicatively connected to the motors 1608*a*, 1608*b*.

Further, the apparatus 1600 includes a telescopic rail 1630 mounted upon a rail mounting plate 1631, the telescopic rail 1630 moveable in a longitudinal direction and operably connected to the moveable plate 1602. Thus, the moveable plate 1602 is moveable along the telescopic rail 1630.

Furthermore, each linkage 1604*a*, 1604*b* includes a hinge 1632 and bearings 1634. There is generally provided four pivot bearing blocks 1636, 1638, 1640 (fourth not shown) in which the linkages 1604*a*, 1604*b* extend through and are supported thereon.

In use, the apparatus 1600 is arranged to rotate the moveable plate 1602 about the central pivot bar 1620, thereby imparting a wave motion, or a rocking motion, to a container engaged by the moveable plate 1602. Additionally, in use, the moveable plate 1602 can be translated along a longitudinal axis, centrally and perpendicularly disposed through the moveable plate 1602, thereby imparting a compression motion to a container engaged by the moveable plate 1602.

The user may operate the apparatus 1600 according to a pre-set program stored within a controller (not shown), which, when it executes a series of operating instructions, performs the desired motion. Alternatively, the user may input parameters into the controller (not shown) to operate the apparatus 1600 according to a desired range of motion.

Although two linkages 1604*a*, 1604*b* are shown in the present embodiment, any number of linkages may be used. Additionally, although the linkages 1604*a*, 1604*b* are driven by motors 1608*a*, 1608*b*, there may alternatively by driven by other mechanisms such as actuators, for example, linear actuators.

Figure 19:
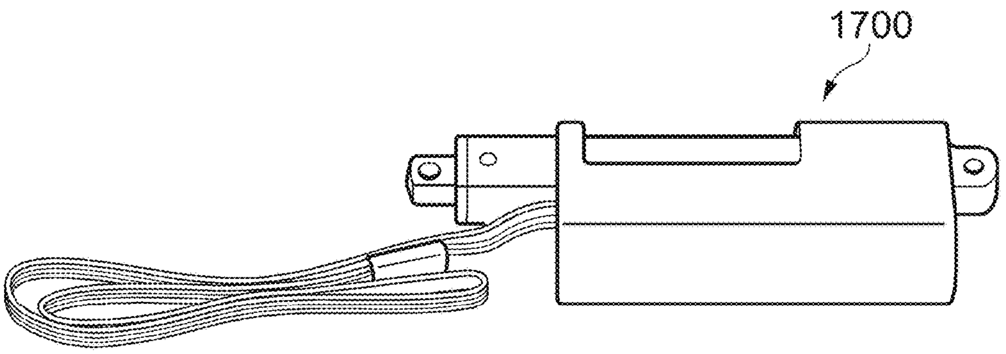
FIG. 19 illustrates a side view a linear actuator for use in the apparatus according to the disclosure.

FIG. 19 illustrates an example of a linear actuator 1700. The linear actuator 1700 may act upon, that is engage, a portion or a surface of any moveable plate as described herein. Alternatively, or additional in embodiment in which a plurality of linear actuators are provided, the linear actuator 1700 may be coupled to a portion or a surface of any moveable plate as described herein.

Figure 20A:
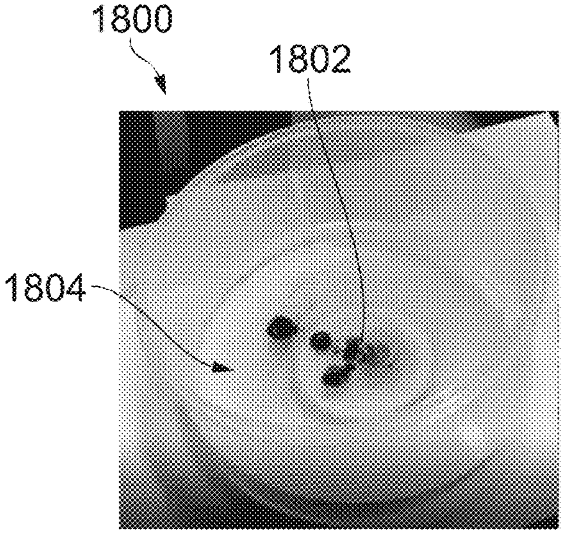
FIG. 20 illustrates (a) a container including water and food coloring prior to agitation and (b) the container including water and food coloring after a swirling agitation.
Figure 20B:
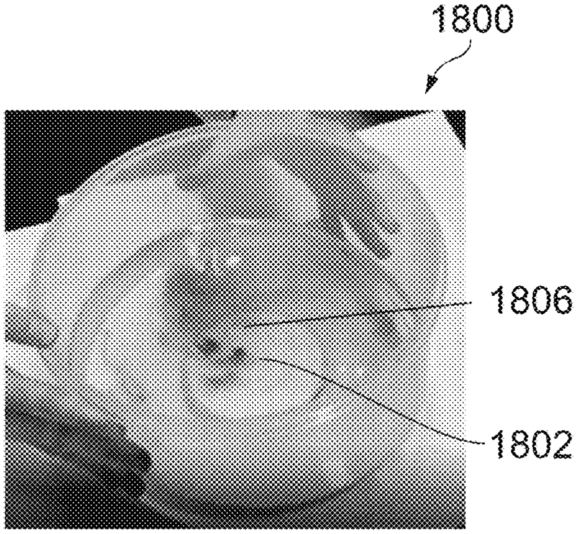

FIGS. 20(*a*) and 20(*b*) illustrate a container before and after a swirling motion, respectively. In particular, FIG. 20(*a*) shows a container 1800 including a central origin 1802 in which a longitudinal axis, extending perpendicularly to a base section of the container 1800, transects the plane of the base section of the container. Such a longitudinal axis is further described in relation to FIGS. 28(*a*) to 30(*c*). The container 1800 includes water and several droplets of food coloring 1804 to demonstrate the various agitation methods described herein. As can be seen in FIG. 20(*b*), after imparting a swirling motion to the water and the food coloring 1804 by pivoting the container 1800 about the central origin 1802, the food coloring begins to mix, as indicated by 1806. Continual swirling provides full dispersion of the food coloring 1804 within the water in the container 1800. This provides an illustration of the mixing of a cell processing medium within the container 1800, in use.

Figure 21A:
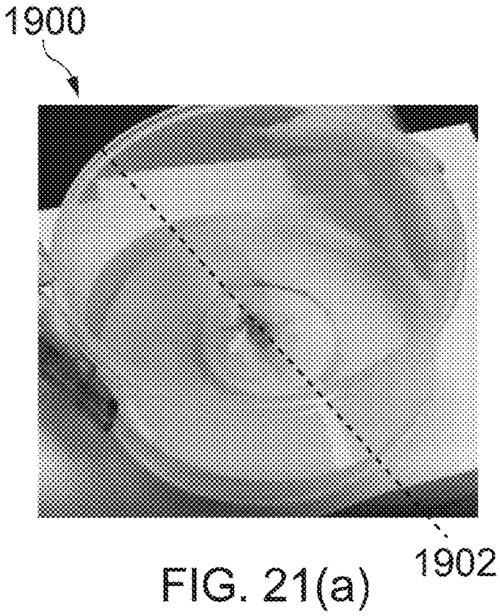
FIG. 21 illustrates (a) a container including water and food coloring prior to agitation and (b) a container including water and food coloring after a wave agitation.
Figure 21B:
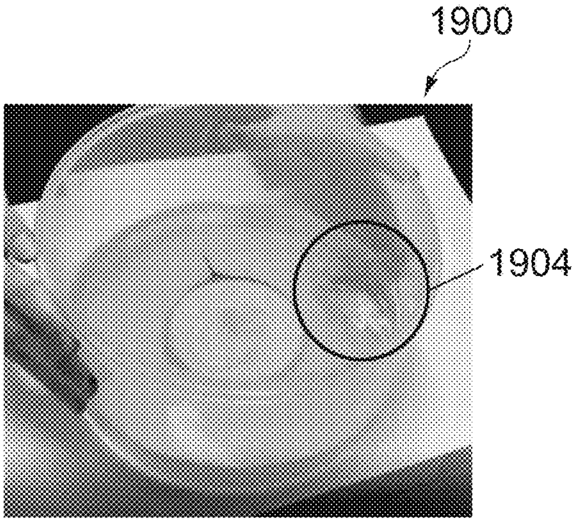

FIGS. 21(*a*) and 21(*b*) illustrate a container before and after a wave motion, respectively. In particular, FIG. 21(*a*) shows a container 1900 including an axis 1902 running perpendicular to a longitudinal axis as described in relation to FIGS. 20(*a*) and 20(*b*), and running within the plane of the base of the container 1900. The container 1900, like the container 1800 of FIGS. 20(*a*) and 20(*b*), includes water and a food coloring to demonstrate the various agitation methods described herein. As can be seen in FIG. 21(*b*), after imparting a wave motion to the water and the food coloring by rotating, tilting, or pivoting, the container 1900 about the axis 1902 (FIG. 21(*a*)), the food coloring begins to mix, particularly toward an wall element of the container 1900. In particular, there may be constructive interference, as indicated by 1904, toward the wall element of the container 1900, thereby aiding mixing of the water and the food coloring. Continual wave agitation provides full dispersion of the food coloring within the water in the container 1900. This provides an illustration of the mixing of a cell processing medium within the container 1900, in use.

Figure 22:
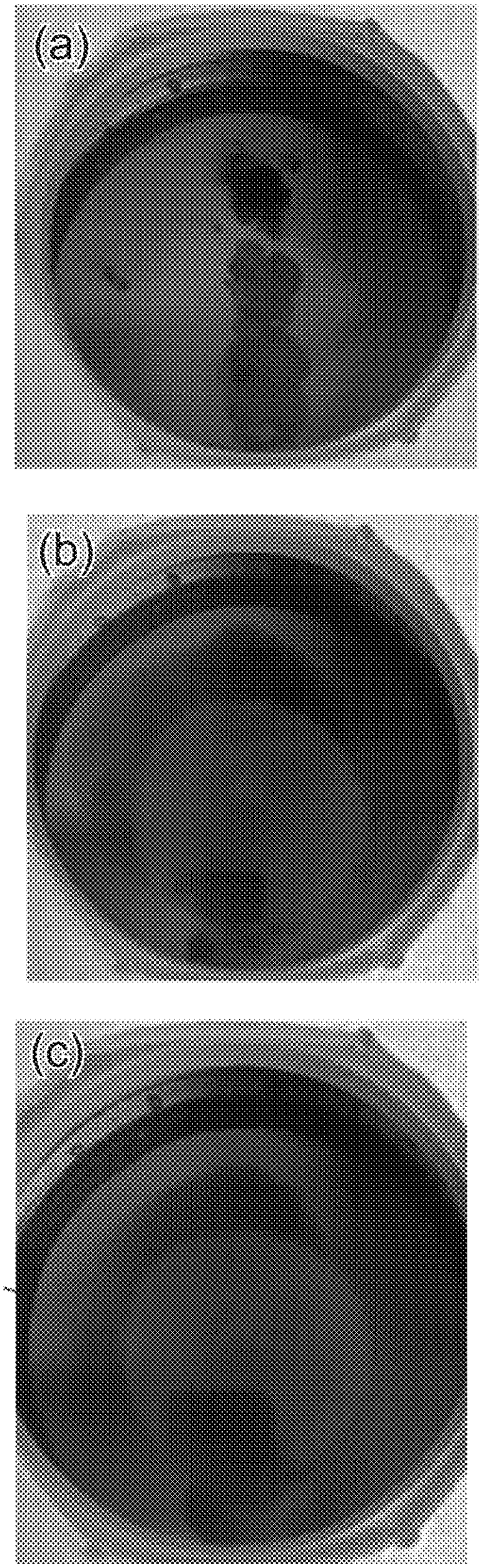
FIGS. 22(*a*) to 22(*c*) illustrate a container having water and food coloring during a swirling agitation.

FIGS. 22(*a*) to 22(*c*) illustrates a container having water and a food coloring therein for simulating the mixing of a cell processing medium within the container. FIG. 22(*a*) illustrates the container in which food coloring has been dropped into the water at time t=0 seconds. FIG. 22(*b*) illustrates the container in which the food coloring begins to mix with the water at time after t=0. FIG. 22(*c*) illustrates the container in which the food coloring is mixed with the water at time after t=0 and after that shown in FIG. 22(*b*). Throughout FIG. 22, a swirling motion, as described in relation to FIGS. 20(*a*) and 20(*b*), is imparted to the water and the food coloring within the container, at 20 revolutions per minute having a water content of 500 mL.

Figure 23:
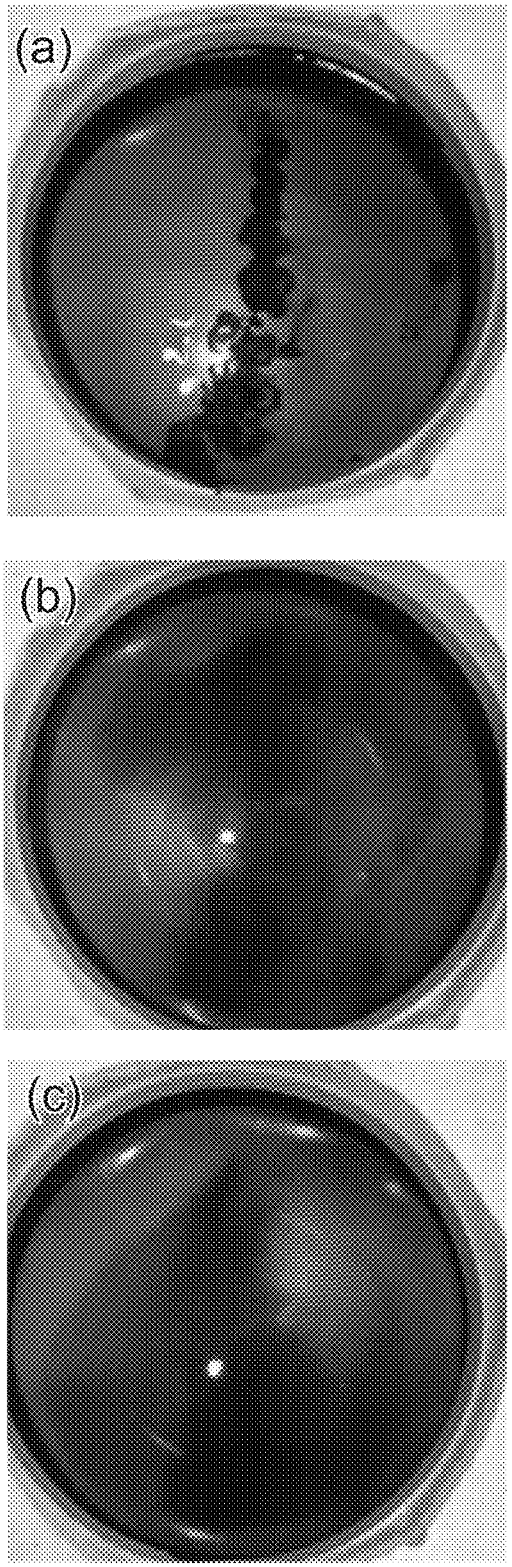
FIGS. 23(*a*) to 23(*c*) illustrate a container having water and food coloring during another swirling agitation.

FIGS. 23(*a*) to 23(*c*) illustrates a container having water and a food coloring therein for simulating the mixing of a cell processing medium within the container. FIG. 23(*a*) illustrates the container in which food coloring has been dropped into the water at time t=0 seconds. FIG. 23(*b*) illustrates the container in which the food coloring begins to mix with the water at a time after t=0 seconds. FIG. 23(*c*) illustrates the container in which the food coloring is mixed with the water at a time after t=0 seconds and after that shown in FIG. 23(*b*). Throughout FIG. 23, a swirling motion, as described in relation to FIGS. 20(*a*) and 20(*b*), is imparted to the water and the food coloring within the container, at 30 revolutions per minute having a water content of 500 mL.

Figure 24:
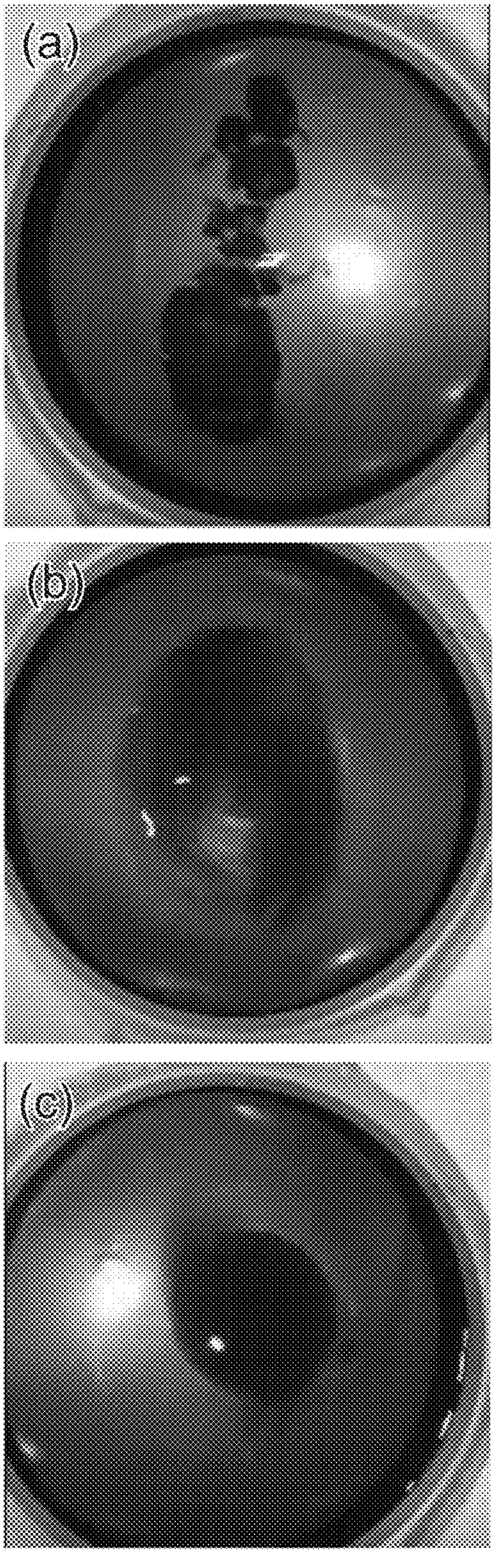
FIGS. 24(*a*) to 24(*c*) illustrate a container having water and food coloring during yet another swirling agitation.

FIGS. 24(*a*) to 24(*c*) illustrates a container having water and a food coloring therein for simulating the mixing of a cell processing medium within the container. FIG. 24(*a*) illustrates the container in which food coloring has been dropped into the water at time t=0 seconds. FIG. 24(*b*) illustrates the container in which the food coloring begins to mix with the water at time after time t=0 seconds. FIG. 24(*c*) illustrates the container in which the food coloring is mixed with the water at time after t=0 seconds and after that shown in FIG. 24(*b*). Throughout FIG. 24, a swirling motion, as described in relation to FIGS. 20(*a*) and 20(*b*), is imparted to the water and the food coloring within the container, at 60 revolutions per minute having a water content of 500 mL.

Thus, as can be seen by comparing FIGS. 22(*c*), 23(*c*) and 24(*c*), at relatively high volumes of fluid, such as 500 mL as demonstrated, a swirl motion does not appear to adequately mix the food coloring within the water. This is a good model of cell processing media within a container.

Figure 25:
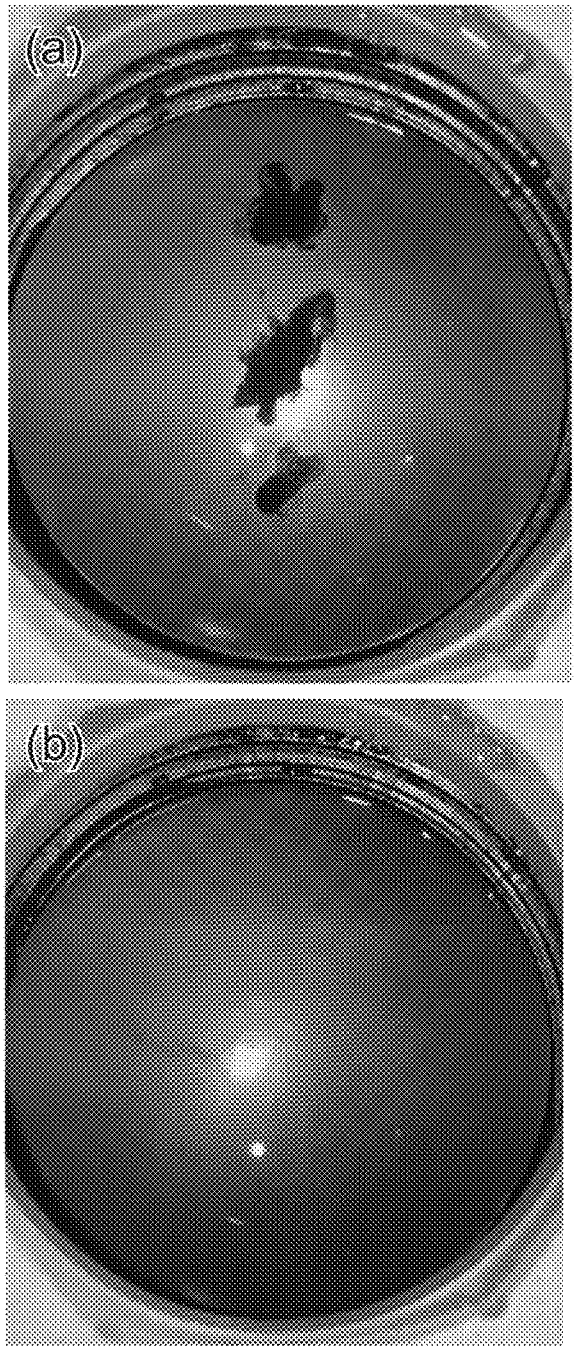
FIGS. 25(*a*) and 25(*b*) illustrate a container having water and food coloring during another swirling agitation.

As shown in FIGS. 25(*a*) and 25(*b*) a container having water and a food coloring therein for simulating the mixing of a cell processing medium within the container. FIG. 25(*a*) illustrates the container in which food coloring has been dropped into the water at time t=0 seconds. FIG. 25(*b*) illustrates the container in which the food coloring begins to mix with the water at time t=60 seconds. Unlike FIGS. 22(*a*) to 24(*c*), through FIGS. 25(*a*) and 25(*b*) a wave motion, as described in relation to FIGS. 21(*a*) and 21(*b*), is imparted to the water and the food coloring within the container, at 20 revolutions per minute having a water content of 50 mL.

Thus, as can be seen by comparing FIG. 25(*b*) with FIGS. 22(*c*), 23(*c*) and 24(*c*), a swirling motion is more suitable for mixing the contents of the container at lower fluid volumes, even at low revolutions per minute. Therefore, a swirling motion may be preferably for small volumes of fluid in cell processing.

Figure 26:
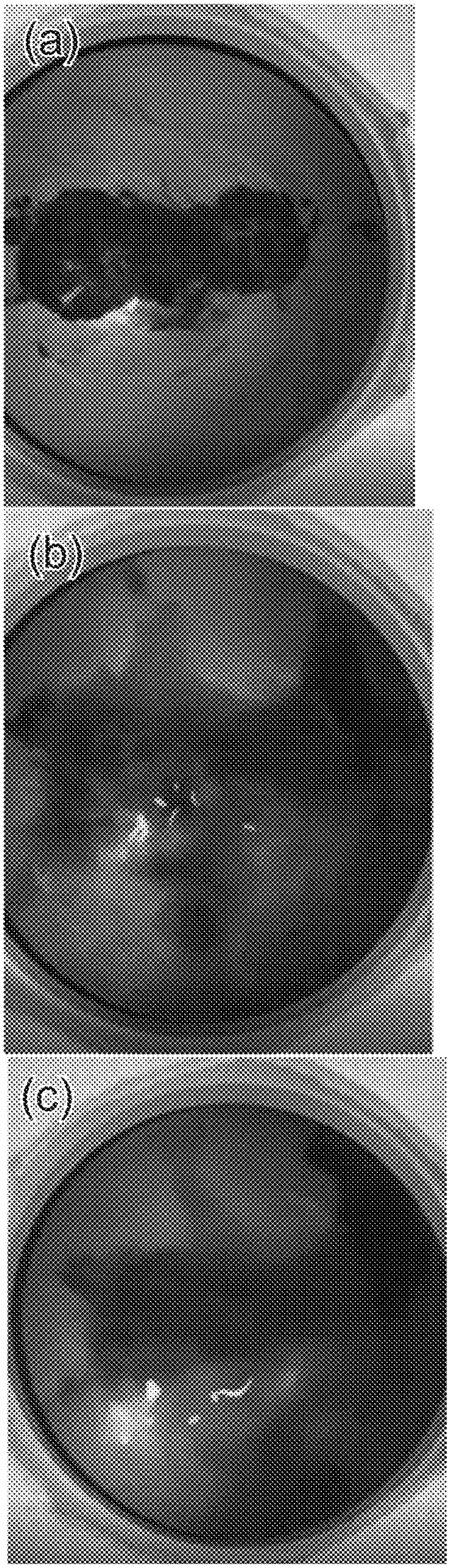
FIGS. 26(*a*) to 26(*c*) illustrate a container having water and food coloring during a linear compression agitation.

FIGS. 26(*a*) to 26(*c*) illustrates a container having water and a food coloring therein for simulating the mixing of a cell processing medium within the container. FIG. 26(*a*) illustrates the container in which food coloring has been dropped into the water at time t=0 seconds. FIG. 26(*b*) illustrates the container in which the food coloring begins to mix with the water at a time after t=0 seconds. FIG. 26(*c*) illustrates the container in which the food coloring is mixed with the water at a time after t=0 and after that shown in FIG. 26(*b*). Throughout FIG. 26, a linear compression motion, that is a compression along a longitudinal axis as described in further detail below, is imparted to the water and the food coloring within the container, at 20 cycles per minute having a water content of 500 mL. As can be seen in FIG. 26(*c*), at low cycles per minute, mixing appears to be largely due to diffusion of the food coloring in the water.

Figure 27:
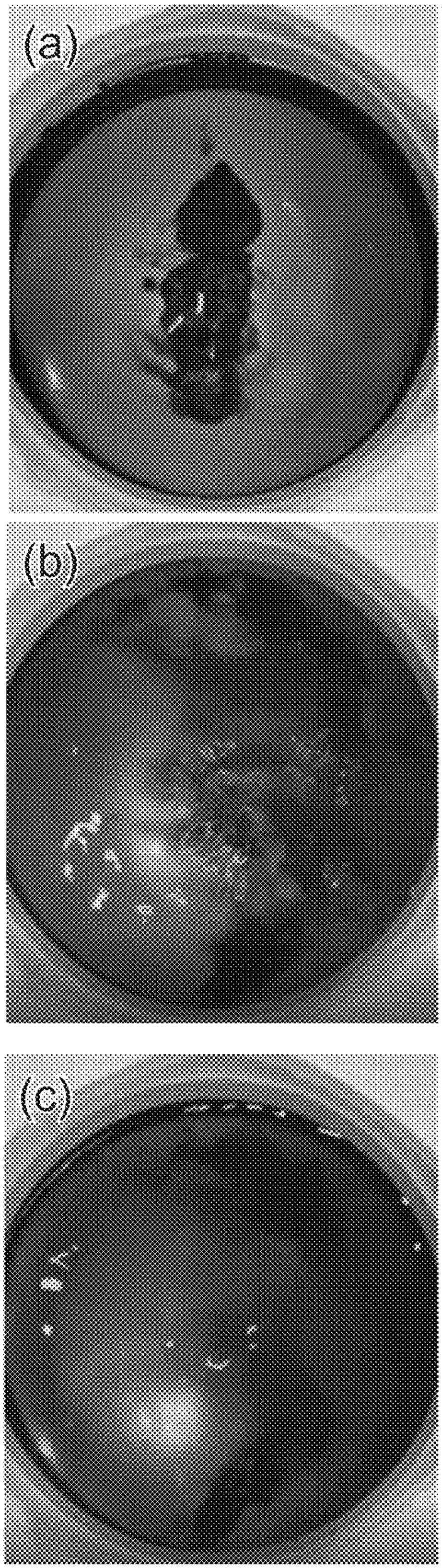
FIGS. 27(*a*) to 27(*c*) illustrate a container having water and food coloring during another linear compression agitation.

FIGS. 27(*a*) to 27(*c*) illustrates a container having water and a food coloring therein for simulating the mixing of a cell processing medium within the container. FIG. 27(*a*) illustrates the container in which food coloring has been dropped into the water at time t=0 seconds. FIG. 27(*b*) illustrates the container in which the food coloring begins to mix with the water at a time after t=0 seconds. FIG. 27(*c*) illustrates the container in which the food coloring is mixed with the water at a time after t=0 seconds and after that shown in FIG. 27(*b*). Throughout FIG. 27, a linear compression motion, that is a compression along a longitudinal axis as described in further detail below, is imparted to the water and the food coloring within the container, at 40 cycles per minute having a water content of 500 mL. As can be seen in FIG. 27(*c*), at increased cycles per minute, mixing is improved.

Figure 28:
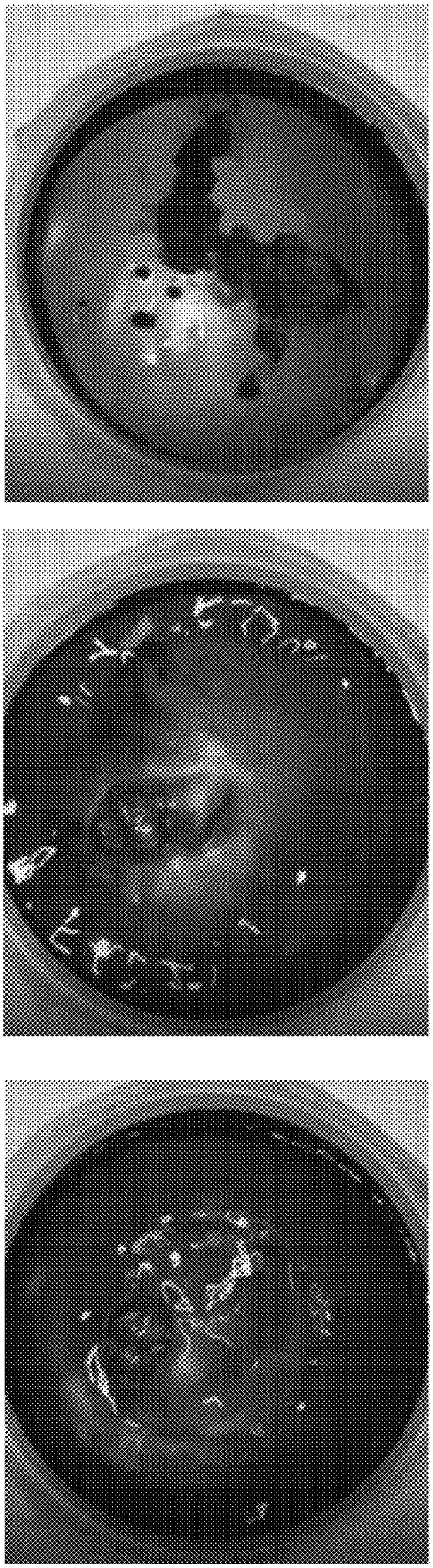
FIGS. 28(*a*) to 28(*c*) illustrate a container having water and food coloring during yet another linear compression agitation.

FIGS. 28(*a*) to 28(*c*) illustrates a container having water and a food coloring therein for simulating the mixing of a cell processing medium within the container. FIG. 28(*a*) illustrates the container in which food coloring has been dropped into the water at time t=0 seconds. FIG. 28(*b*) illustrates the container in which the food coloring begins to mix with the water at a time after t=0 seconds. FIG. 28(*c*) illustrates the container in which the food coloring is mixed with the water at time after t=0 seconds and after that shown in FIG. 28(*b*). Throughout FIG. 28, a linear compression motion, that is a compression along a longitudinal axis as described in further detail below, is imparted to the water and the food coloring within the container, at 80 cycles per minute having a water content of 500 mL. As shown in FIG. 28(*b*), occasionally, large bubbles are created during the linear compression, which can aid in aerating the mixture, which can be useful in cell processing methods. As shown in FIG. 28(*c*), good mixing is achieved for higher volumes of fluid at larger cycles per minute.

Thus, it has been found that at small volumes, particularly less than 100 mL, a swirling motion is suitable for adequately mixing a fluid in the container. Moreover, it has been found that at larger volumes, particularly 100 mL or greater, a linear compression motion is suitable for adequately mixing a fluid in the container. Thus, an agitation mechanism should be able to provide both ranges of motion, so that any volume of fluid may be adequately mixed.

Figure 29A:
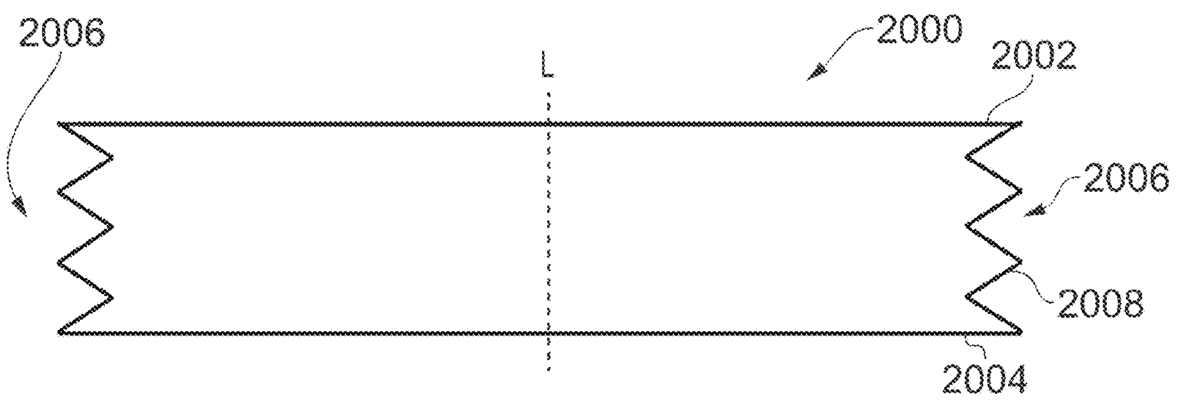
FIG. 29 illustrates (a) a side view of a container in a first configuration and (b) a side view of a container in a second configuration.
Figure 29B:
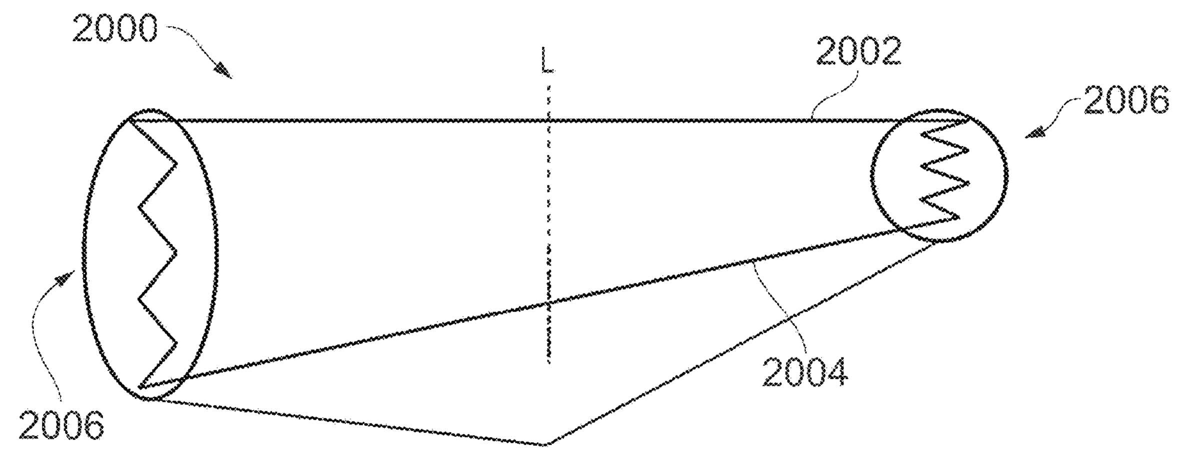
Figure 30A:
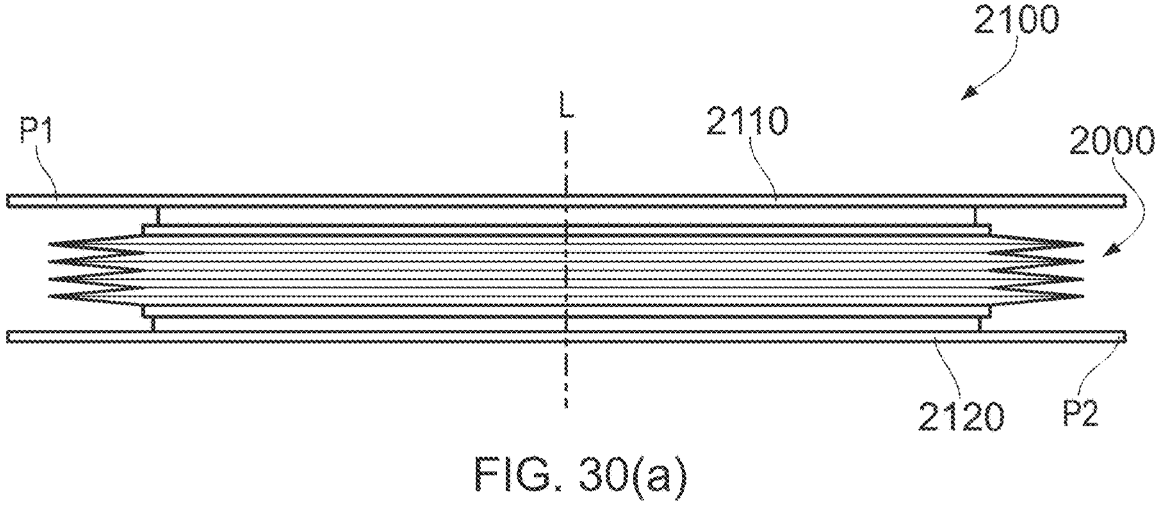
FIGS. 30(*a*) to 30(*e*) illustrate a system, including a container and an apparatus according to the disclosure, throughout the compression motion.
Figure 30B:
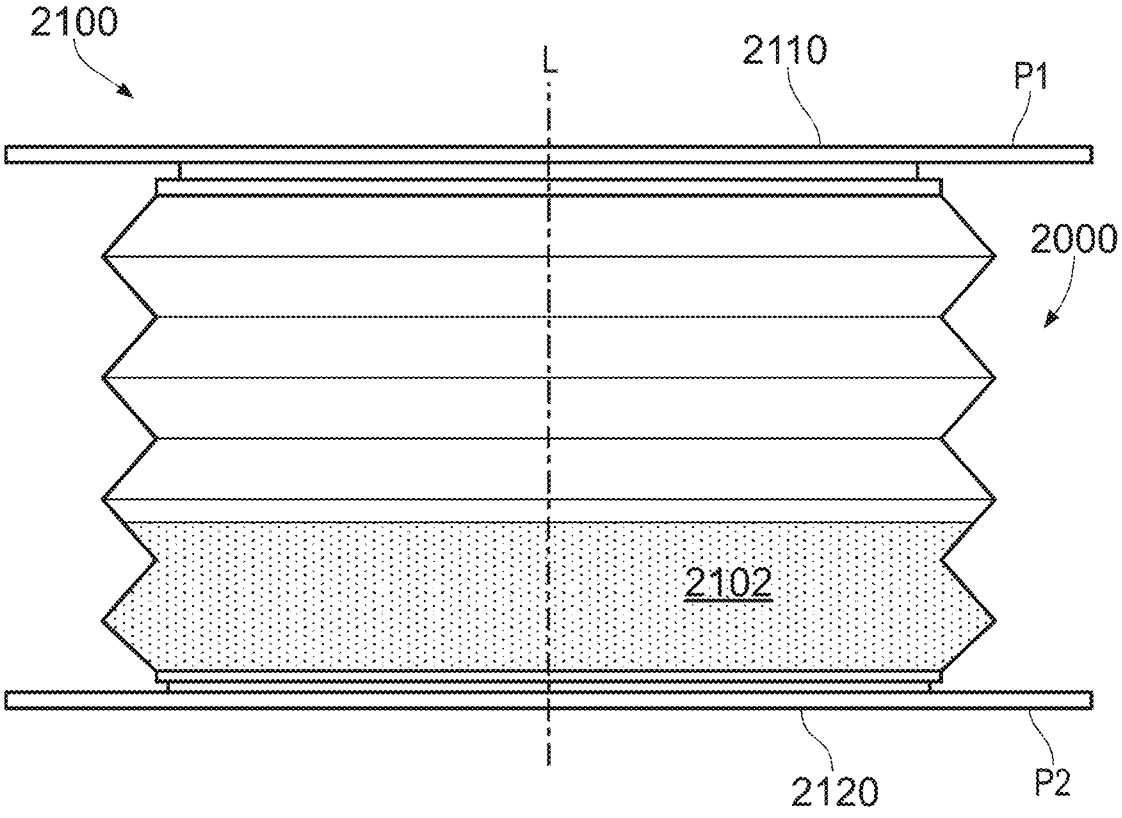
Figure 30C:
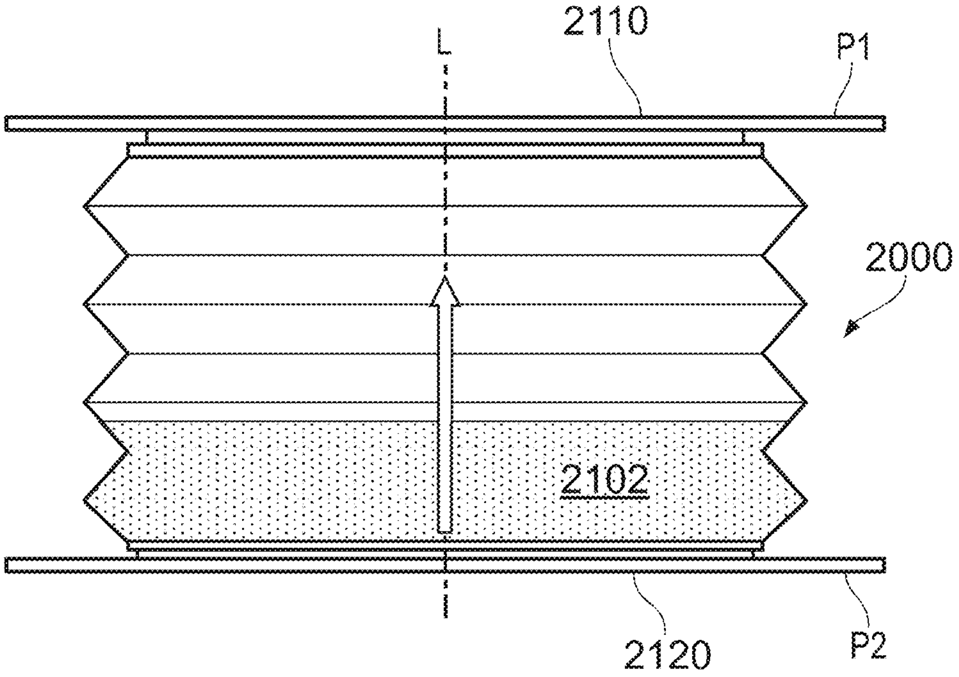
Figure 30D:
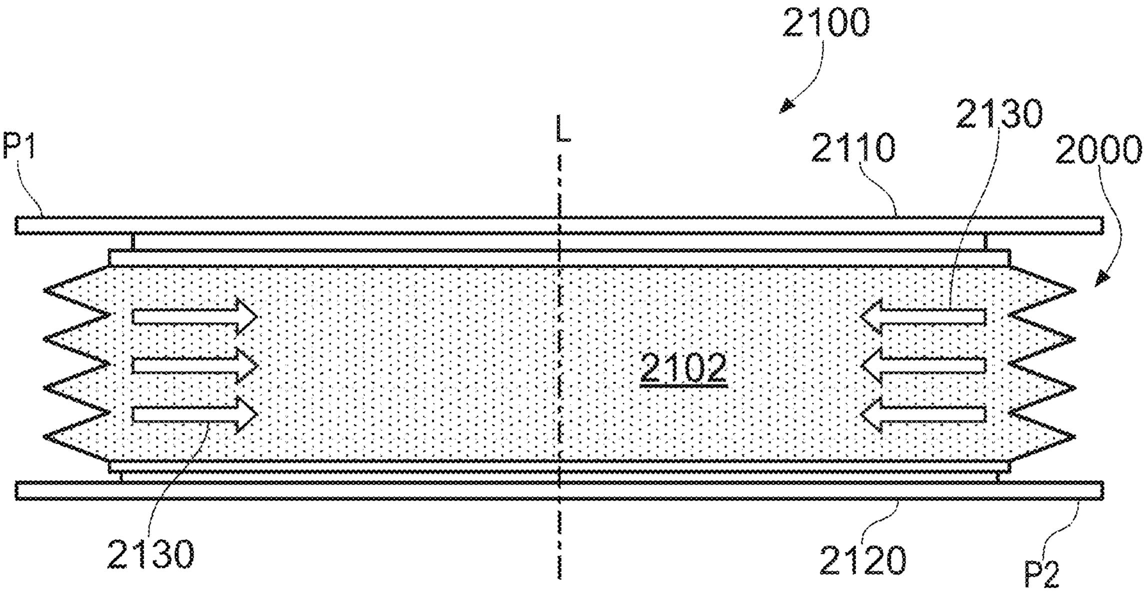
Figure 30E:
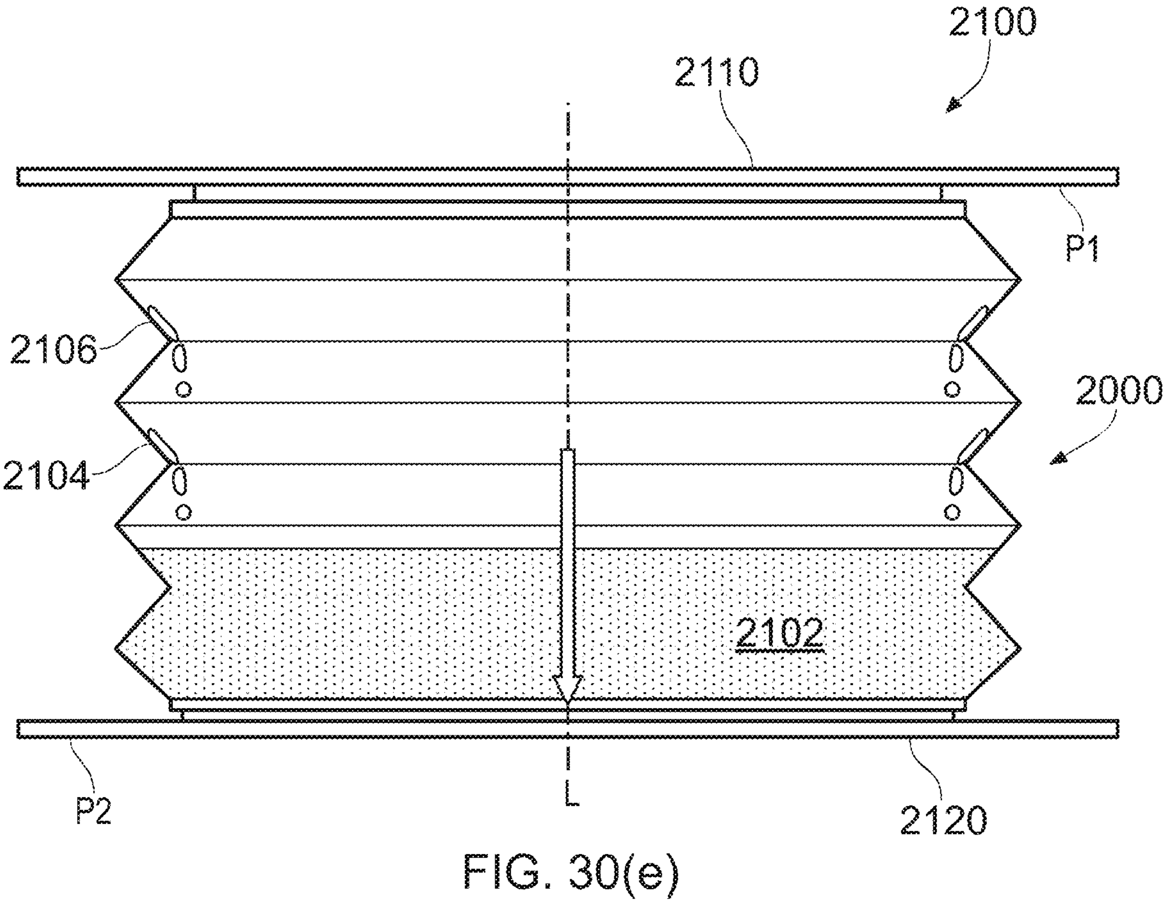

FIGS. 29(*a*) and 29(*b*) illustrate a container according to the disclosure. The container 2000 includes a top section 2002, a base section 2004 extending in parallel to the top section 2002, and a wall element 2006 therebetween. The wall element 2006 is compressible along the longitudinal axis L of the container 2000. The wall element 2006 may comprise one or more Z-folds 2008, or may form a concertina, such that it is compressible along the longitudinal axis L. FIG. 29(*a*) illustrates the container 2000 prior to compression. FIG. 29(*b*) illustrates the container 2000 after compression of a portion of the wall element 2006. Generally, each of the top section 2002 and the base section 2004 generally define a plane, each plane being parallel to one another and substantially perpendicular to the longitudinal axis L.

FIGS. 30(*a*) to 30(*e*) illustrate an apparatus 2100 including a container 2000, according to the disclosure. The apparatus 2100 includes a holding element 2110 and a moveable plate 2120. The moveable plate 2120 can be any moveable plate as described herein, and moveable by any actuation mechanism as described herein. The holding element 2110 holds a top section of the container 2000 within a first plane P1, and the moveable plate 2120 forms a second plane P2, substantially parallel to the first plane P1, for moving the base section of the container 2000. Prior to operation, i.e., actuation and moving of the moveable plate 2120, the first and second planes P1, P2 extend substantially horizontally, and substantially perpendicular to the longitudinal axis L.

As shown in FIG. 30(*a*), the container 2000 may be compressed along the longitudinal axis L, such that the first plane P1 remains stationary and such that the moveable plate 2120, and thus the second plane P2, is caused to move. Compression along the longitudinal axis L may cause mixing of media within the container 2000 as described above. In the example show, a 50 ml transduction may take place. The liquid may have a depth of approximately 2.75 mm.

As shown in FIG. 30(*b*), the container 2000, containing media 2102, may be expanded, or decompressed, along the longitudinal axis L, such that the first plane P1 remains stationary and such that the moveable plate 2120, and thus the second plane P2, is caused to move. Expansion along the longitudinal axis L may be beneficial in the cell processing method, for example, for cell cultivation or growth. In the example shown, a 500 mL expansion may take place. The liquid may have a depth of approximately 27 mm.

As shown in FIG. 30(*c*), the container 2000 may be subjected to further compression, thus agitating the media 2102 therein, along the axis L as indicated by the arrow. This causes the container 2000, specifically the wall element thereof, to be compressed along the longitudinal axis L. That is, the first plane P1 remains stationary and the moveable plate 2120, and the second plane P2, are moved.

As shown in FIG. 30(*d*), as the headspace within the container 2000 above the media 2102 is reduced, media 2102 residing within the wall element of the container 2000 is forced inwardly (directional arrows 2130 and 2120), toward the longitudinal axis L. This motion causes agitation within the container 2000 of the media 2102. This may be beneficial to a number of steps in the cell processing method.

As shown in FIG. 30(*e*), as the container 2000 is expanded, or decompressed, along the longitudinal axis L, media 2104, 2106, which has collected within the wall element of the container 2000 during compression, is caused to flow, drop or drip, into the bulk of the media 2102, thereby causing further agitation within the container. This may be beneficial to a number of steps in the cell processing method.

The compression may force medium to be compression out of the folds as the container is raised and lowered repeatedly. Compression pauses to a set period of time may also be provided—that is, a compression may be held, or stopped, such that the container is in a compressed state for a predetermined period of time. This allows cell sedimentation before medium exchange. The compression steps may result in excellent mixing and gaseous transfer. Such a process may also be scalable. Thus, there may be a number of advantages associated with such a compression process described herein for cell processing methods.

Figure 31A:
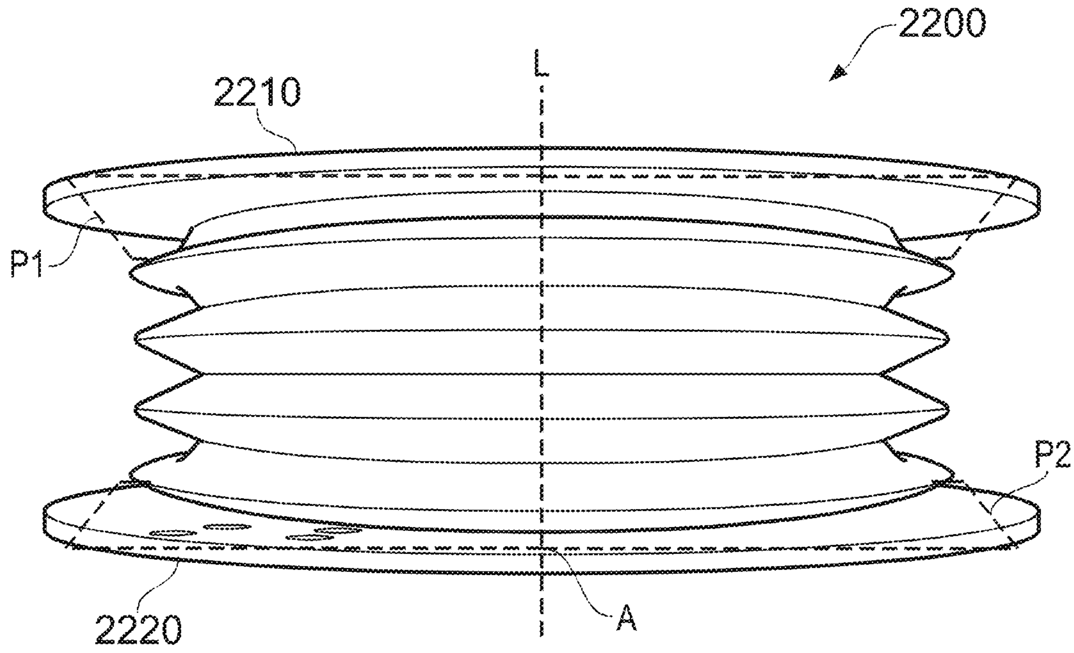
FIG. 31 illustrates (a) a side view of a system including a container and an apparatus according to the disclosure in a first configuration, (b) a side view of the system in a second configuration after rotation about an axis and (c) a side view of the system in a third configuration.
Figure 31B:
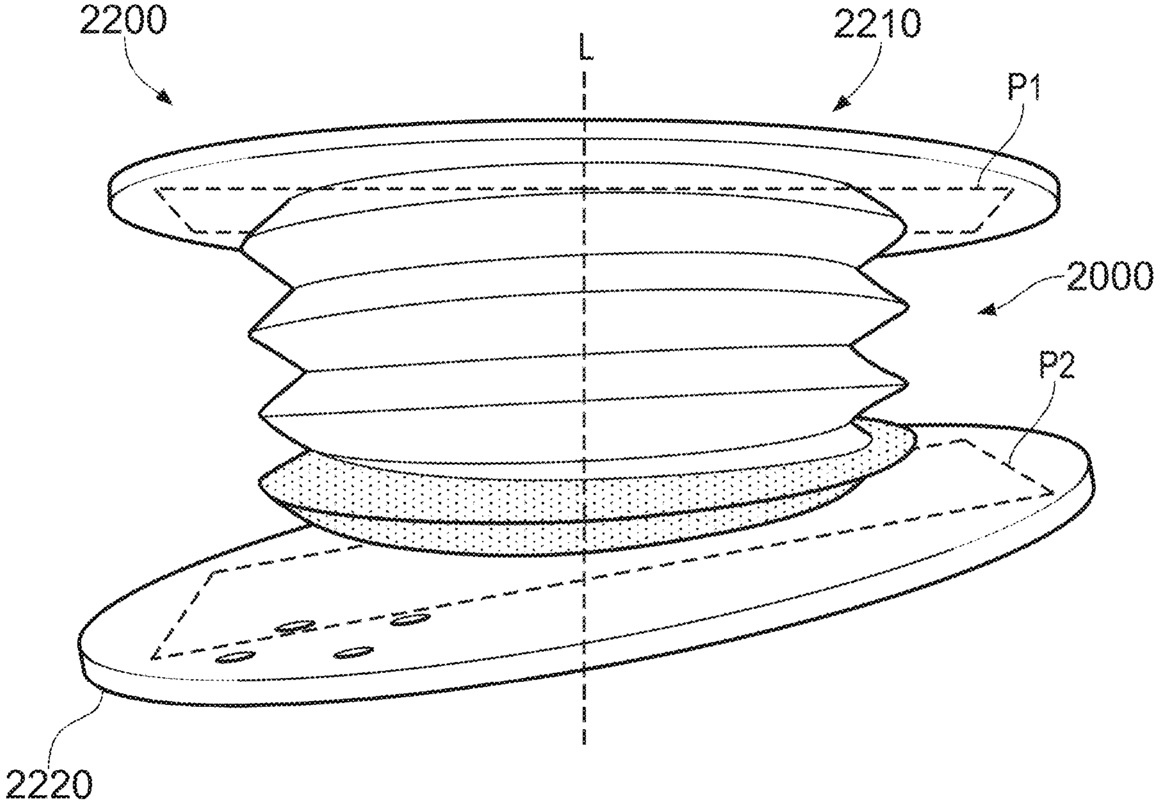
Figure 31C:
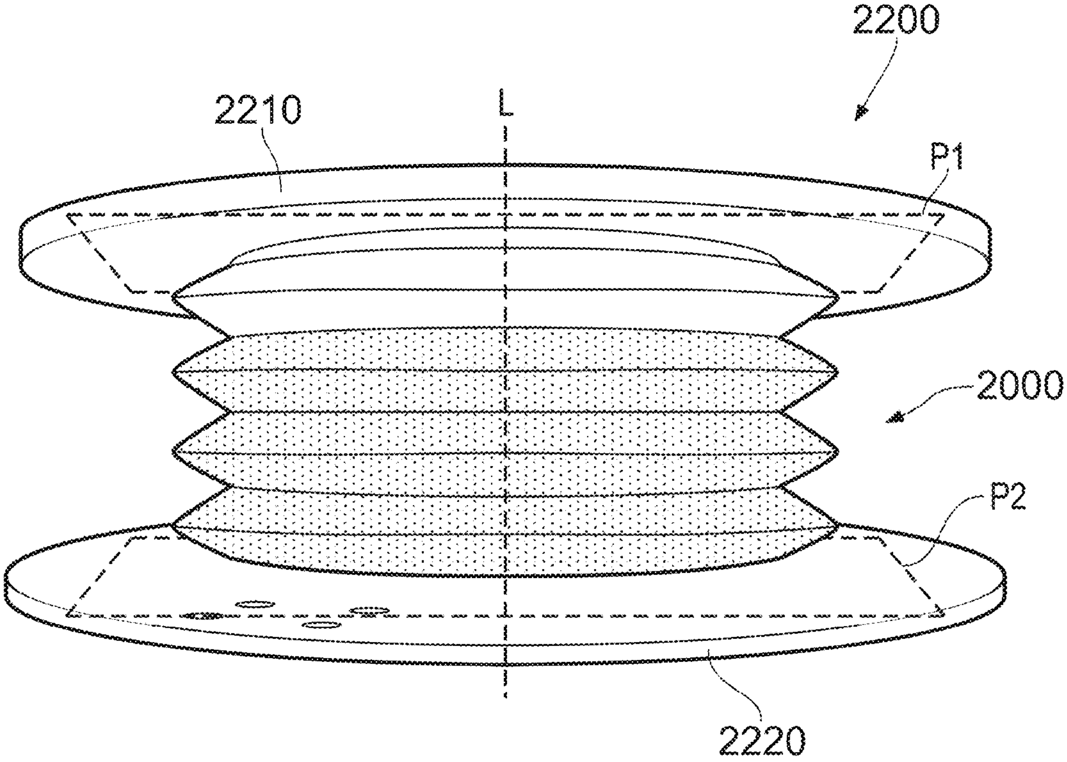

FIGS. 31(*a*) to 31(*c*) illustrate a further apparatus 2200 of the disclosure. The apparatus 2200 includes a holding element 2210 for receiving and holding a top section of the container 2000 within a first plane P1. The apparatus 2200 further includes a moveable plate 2220 for acting upon, or engaging, a base section of the container 2000, the moveable plate 2220 defining a second plane P2. The first plane P1 and the second plane P2 are substantially parallel and extend substantially perpendicularly to the longitudinal axis L.

As shown in FIG. 31(*a*), a static phase or step of a method is shown, in which the container 2000 is not agitated in any way. This may be beneficial to a number of steps in the cell processing method.

As shown in FIG. 31(*b*), an agitation phase or step of a method is shown, in which the container 2000 is agitated so as to cause agitation, or turbulence, of media within the container 2000. In this particular example, the agitation phase includes rotating the moveable plate 2220 about at least one axis within the plane P2, for example, the axis A indicated in FIG. 31(*a*). The plane P2 moves as the moveable plate 2220 moves. Thus, as the moveable plate 2220 moves, the plane P2, or a portion thereof, moves toward the plane P1, which remains stationary. Thus, a distance between at least a portion of the plane P2 and the plane P1 is decreased. The movement of the moveable plate 2220 about the axis A causes a portion of the wall element of the container 2000 to be compressed, as shown in FIG. 31(*b*). As the moveable plate 2220 rotates, or tilts, in the opposition direction, an opposing portion of the wall element of the container 2000 is compressed. Thus, a wave motion, as described above, may be effected upon the media within the container 2000. Furthermore, the moveable plate 2220 may be pivotable about an origin, in which the longitudinal axis L intersects the second plane P2, such that the origin remains stationary and all other points move. In this example, a swirling motion, as described above, may be effected upon the media within the container 2000. In other examples, the moveable plate 2220 may be rotatable or arranged to be tilted about any number of axes within the second plane P2 to cause any desired agitative effect on the media within the container 2000.

As shown in FIG. 31(*c*), a compression phase or step of a method is shown, in which the container 2000, specifically the wall element, is compressed along the longitudinal axis L such that the first plane P2 is caused to move closer toward the first plane P1. Thus, as shown in FIG. 31(*c*), the headspace above the media within the container 2000 may be changed, for example, air may be pushed out of the container 2000. Further compression may cause agitation as described above.

Figure 32:
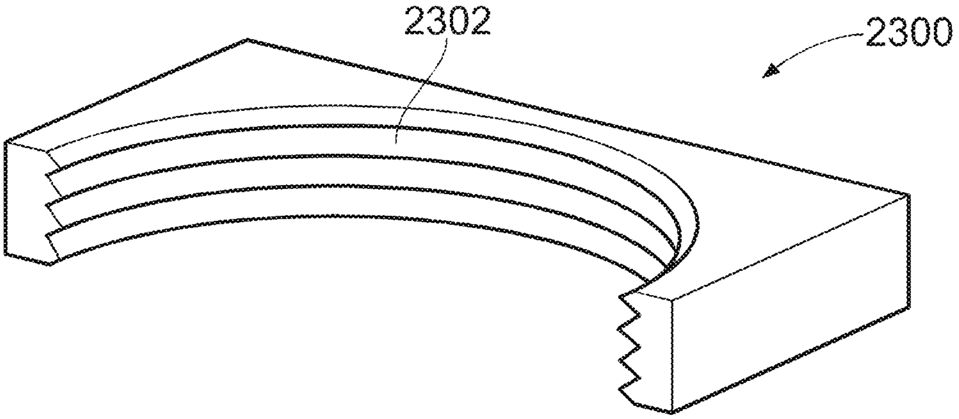
FIG. 32 illustrates a mold for a container.
Figure 33A:
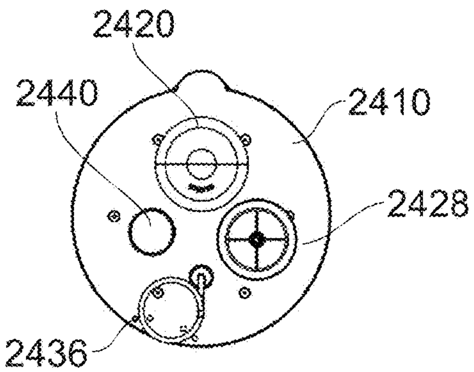
FIG. 33 illustrates (a) a top down view, (b) a side view, (c) a bottom view and (d) an exploded perspective view of a platform and containers suitable for use with the apparatus and system according to the disclosure.
Figure 33B:
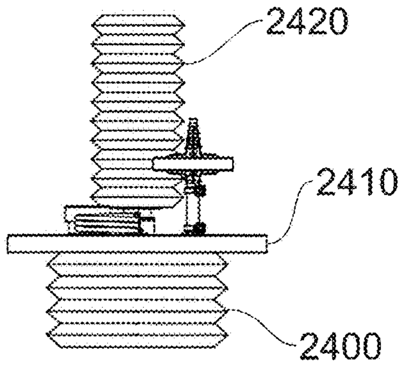
Figure 33C:
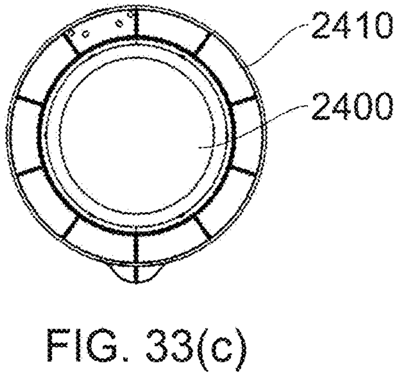
Figure 33D:
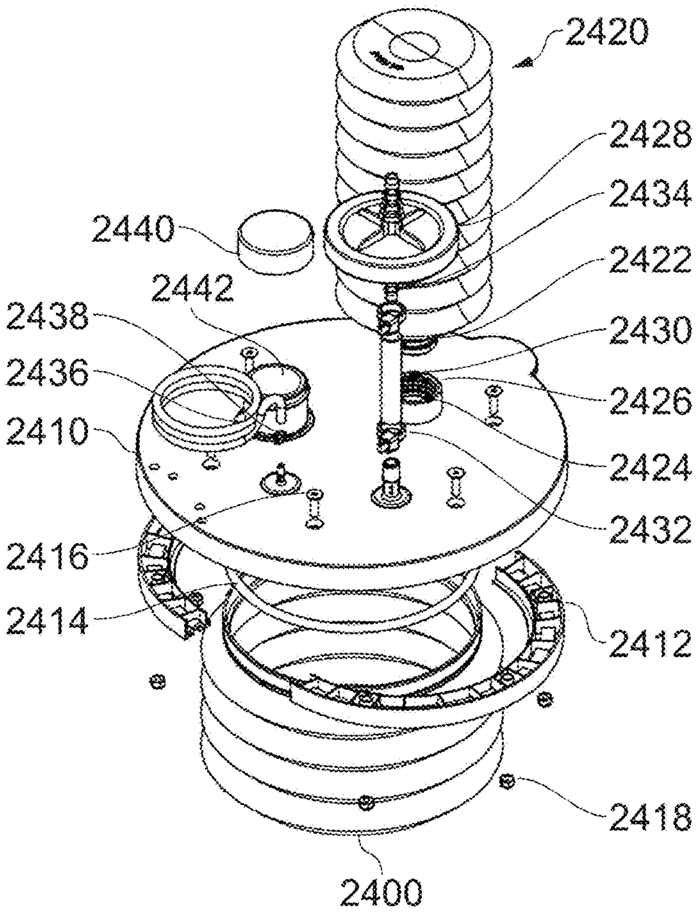
Figure 34A:
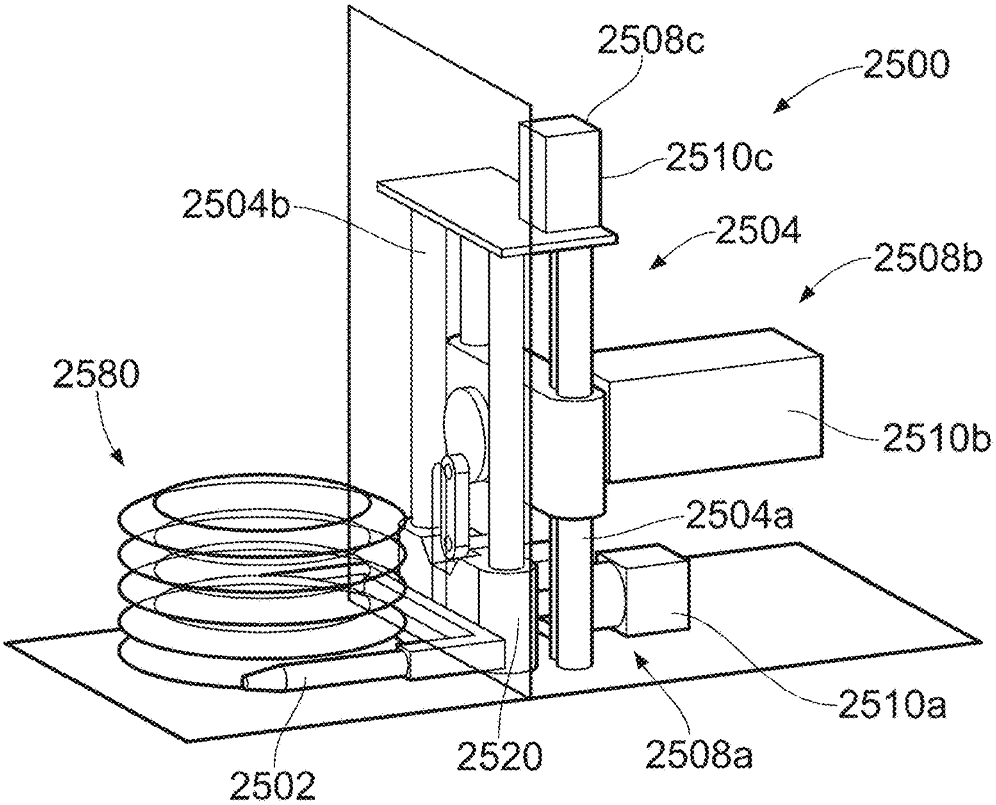
FIG. 34 illustrates (a) a perspective view of a schematic of the apparatus according to another embodiment of the disclosure, (b) a front view of the schematic of (a), (c) a schematic view of one motor and linkage of the apparatus of (a), and (d) a schematic view of another motor and linkage of the apparatus of (a)
Figure 34B:
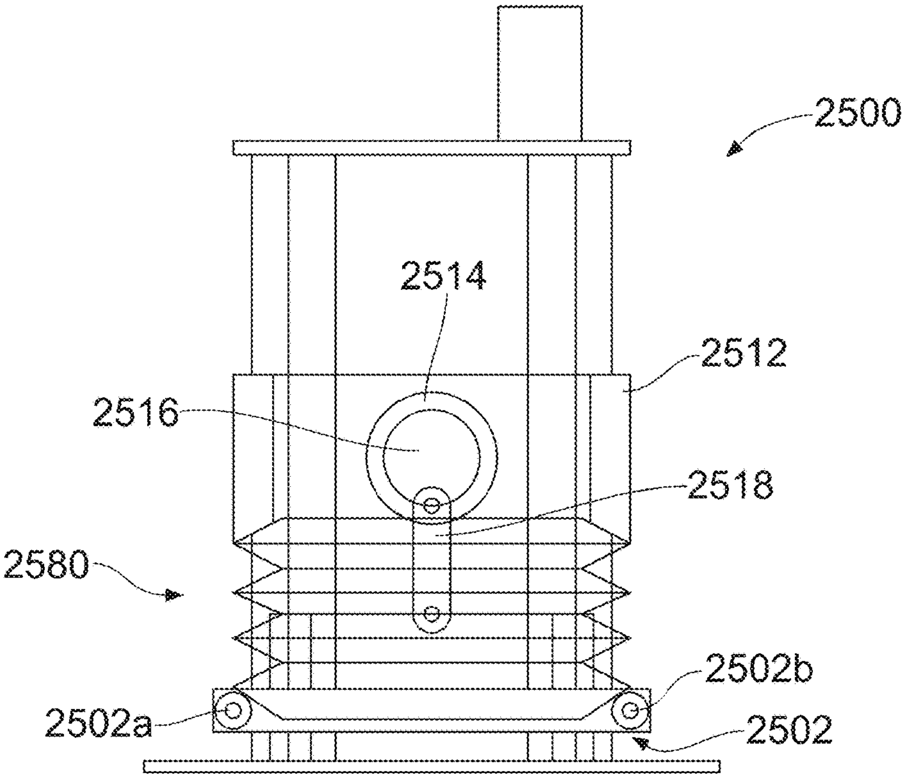
Figure 34C:
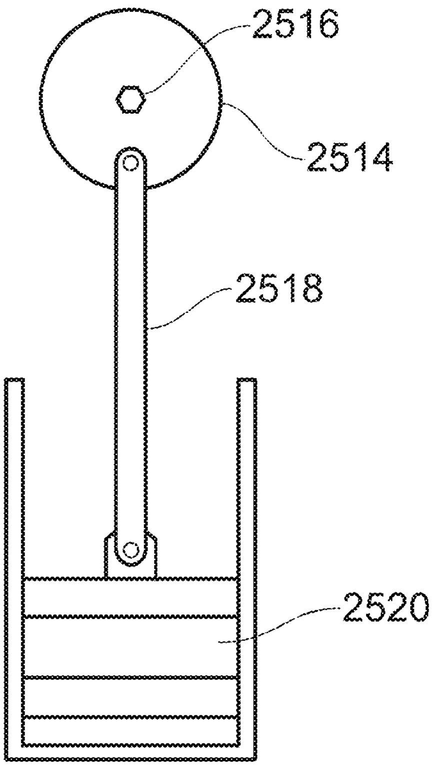
Figure 34D:
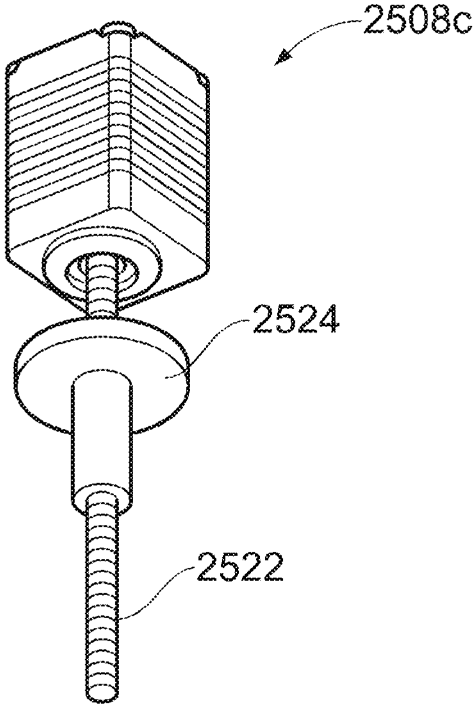

FIG. 32 illustrates a mold or an insert 2300 for producing a container as described herein. The mold 2300 may be suitable for blow-molding. As such, the container may be formed by blow-molding. The mold 2300 includes a series of protrusions, or ridges, 2302, arranged to provide the series of Z-folds, or the concertina arrangement, of the containers described herein.

FIGS. 33(*a*) to 33(*d*) illustrate an example of a container 2400, a platform 2410 and other components that may be used in combination with the apparatuses or systems described herein. FIG. 33(*d*) shows a container 2400 having a top section that is substantially open thereby forming a fluid passageway, and a base section that is substantially closed. There is a wall element extending between the top section and the base section as described in relation to FIGS. 29(*a*) and 29(*b*). The wall element may comprise a compressible portion, for example, Z-folds as shown in FIGS. 33(*b*) and 33(*d*). The container 2400 may form a bellows, for example, a 4-fold bellows, or a concertina arrangement.

Referring further to FIG. 33(*d*), the container 2400 is attachable to a platform 2410, which may be regarded as a cell processing platform, at an underside thereof. There may also be provided a clip 2412, which may form the holding element as described herein. The clip 2412 may be provided in two halves as shown. The container 2400 may be sealed by way of an O-ring 2414 that is urged between the top section of the container 2400 and the underside of the platform 2410. The clip 2412 may be coupled to the platform 2410 by way of bolts 2416 and corresponding nuts 2418.

The platform 2410 may have any number of features. For example, the platform 2410 may have a series of fluid inlets having attachment elements for attaching various pieces of equipment. The platform 2410 may have one or more, preferably one, fluid outlet in fluid communication with the fluid inlets. For example, as shown in FIG. 33(*d*), the attachment elements of the inlets of the platform 2410 may be coupled to a secondary container 2420 having a neck 2422 including a screw thread for screwing to a corresponding screw thread of an attachment mechanism 2424 of the platform 2410. The attachment mechanism 2424 may also include an O-ring 2426 to ensure a fluid or liquid tight seal. The platform 2410 may also include a male connector element 2428 for connecting the platform 2410 to one or more tubes or other pieces of equipment. The male connector element 2428 is fluid coupled to a fluid inlet of the platform 2410 by tubing 2430, for example, flexible tubing, held in place by a cable tie 2432. A filter 2434 may also be present between the flexible tubing 2430 and the male connector element 2428. The platform 2410 may also include tubing 2436 coupled to an inlet of the platform 2410 for connecting to other pieces of equipment. The tubing 2436 may be flexible tubing. The tubing 2436 is coupled to the fluid inlet of the platform 2410 by a cable tie 2438. The platform 2410 may also include a cap 2440 for covering one or more elements, for example, a sampling element 2442 or the inlets, of the platform 2410.

In use, the secondary container 2420 acts as a breathing container for the container 2400. That is, as the container 2400 is compressed or decompressed or otherwise moved by, for example, a moveable plate of the disclosure, the secondary container 2420 allows for the compensation of pressure increases and/or decreases in the container 2400. In particular, as the container 2400 is acted upon, at its base section by the moveable plate, fluid, for example, air, may be forced out of the container 2400, through the platform 2410, and into the secondary container 2420. Likewise, if the container 2400 is pulled downwardly, or otherwise decompressed, then fluid, for example, air, may be drawn into the container 2400, through the platform 2410 from the secondary container 2420. Thus, the secondary container 2420 acts as a breathing container in that it accounts for pressure changes in the container 2400.

FIGS. 34(*a*) to 34(*d*) illustrate another apparatus 2500, and components thereof, in accordance with the disclosure. As best shown in FIGS. 34(*a*) and 34(*b*), the apparatus 2500 includes a moveable plate 2502, formed with two protruding arms 2502*a*, 2502*b* for frictionally engaging a side wall adjacent a base of a container 2580. The apparatus 2500 is depicted without the holding element, for clarity only, though this is discussed in further detail in relation to FIGS. 35(*a*) to 35(*e*) below.

The apparatus includes a linkage 2504 connecting the moveable plate 2502 to a first motor 2508*a*, a second motor 2508*b* and a third motor 2508*c*. Each motor has respective gearboxes 2510*a*, 2510*b*, 2510*c*. The first motor 2508*a* is arranged to rotate the moveable plate 2502 about an axis formed within a plane thereof. The second and third motors 2508*b*, 2508*c*, are arranged to move the moveable plate 2502 in a longitudinal direction as described in more detail below.

Specifically, the linkage 2504 illustrated includes a first longitudinal rail 2504*a* and a second longitudinal rail 2504*b*. Each longitudinal rail 2504*a*, 2504*b* is generally formed as a pair of complementary rails in this particular embodiment. The linkage 2504 further includes a crank housing 2512, including a crank 2514 driven by a shaft 2516, which is connected to the second motor 2508*b*, which is slidable along the first longitudinal rail 2504*a* in an upward and/or downward direction.

The linkage 2504 further includes a slider portion 2520, connected to the moveable plate 2502, which is slidable along the second longitudinal rail 2504*b* in an upward and/or downward direction. The crank 2514 is connected to the slider portion 2520 by a connecting rod 2518. The slider portion 2520 also includes a shaft (not shown) extending therethrough so as to couple the moveable plate 2502 to the first motor 2508*a*.

Referring further to FIG. 34(*c*), the crank arrangement discussed above is illustrated in more detail. In particular, there is provided the crank 2514 driven by the shaft 2516 by the second motor (not shown). The crank 2514 is coupled to a connecting rod 2518, which terminates in the slider portion 2520. The crank 2514 has a diameter of 40 mm in the depicted example, but other diameters are equally contemplated. The crank 2514 may be replaceable, such that it can be replaced by larger or smaller diameter cranks such that the displacement of the moveable plate during use is adjusted accordingly. For example, for larger displacements, a larger diameter crank may be used. For example, for smaller displacements, a smaller diameter crank may be used.

In use, as the crank 2514 is caused to rotate, and thus the connecting rod 2518 moves, the slider portion 2520 is caused to axially move upwardly and then, as the crank 2514 continues to rotate, is caused to axially move downwardly. As such, the slider portion 2520 is moveable between a first position, or a home position, and a second position, or an elevated position, by the crank 2514. The slider portion 2520 then returns to the first position, or the home position, upon continuing rotation of the crank 2514. In this way, the crank arrangement allows for rapid upward and downward movement of the moveable plate, thus imparting a full compression and decompression cycle to a received container, during use, with each rotation of the crank 2514.

Referring further to FIG. 34(*d*), the third motor 2508*c* is illustrated in more detail. In particular, the third motor 2508*c* is shown as a lead screw thread motor or a ball screw thread motor, including a drivable threaded shaft 2522. The driveable threaded shaft 2522 is threadedly coupled to a corresponding screw threaded portion 2522, which forms part of the crank housing 2512 (see FIG. 34(*a*)). As such, as the threaded shaft 2522 is driven, the screw threaded portion 2522 of the crank housing 2512 is caused to axial move, either upwardly or downwardly depending upon the rotational direction of the driven shaft 2524. As such, the crank housing 2512 is moveable along the first longitudinal rail 2504*a* (see FIG. 34(*a*)). Thus, owing to the crank arrangement discussed above, the moveable plate 2502 (see FIG. 34(*a*)) is similarly moveable, along the second longitudinal rail 2504*b* (see FIGS. 34(*b*) and (*c*)). In this way, the lead screw or ball screw arrangement allows for slower upward and downward movement of the moveable plate.

Referring to FIGS. 34(*a*) to 34(*d*), during use, a container 2580 is received within the apparatus 2500, specifically between the moveable plate 2502 and a holding element (not shown). The first motor 2508*a* is caused to be actuated, so as to rotate the moveable plate 2502 about an axis within the plane of the moveable plate 2502. Furthermore, the second motor 2508*b* is caused to be actuated, either intermittently or continuously, so as to cause axial translation of the moveable plate 2502 along a longitudinal axis, parallel to the first and second longitudinal rails 2504*a*, 2504*b*. As discussed above, the second motor 2508*b* causes the shaft 2516 to rotate, thereby rotating the crank 2514. As the crank 2514 rotates, the connecting rod 2518 is caused to move, thereby axially moving the slider portion 2520 along the second longitudinal rail 2504*b*. Owing to the configuration of the crank arrangement, the slider portion 2520, and thus the moveable plate 2502, is caused to move axially upwardly and downwardly, thereby imparting a compression and decompression motion to the container 2580. Further, due to this configuration, the axial movement of the slider portion 2520, by the second motor 2508*b*, is limited to a predetermined region along the longitudinal axis. Furthermore, the third motor 2508*c* is caused to be actuated, so as to cause rotation of the driven shaft 2524, thereby axially translating the crank housing 2512 upwardly or downwardly, depending upon the direction of rotation of the driven shaft 2524. As such, the crank housing 2512 is caused to axially move along the first longitudinal rail 2504*a*, thereby imparting a slow compression or decompression motion to the container 2580.

For completeness, the person skilled in the art would readily appreciate that the motors 2508*a*, 2508*b*, 2508*c* can be actuated in any order, or indeed in combination with one another. The above description of the use of the apparatus 2500 is not intended to be limiting in any sense.

Figure 35:
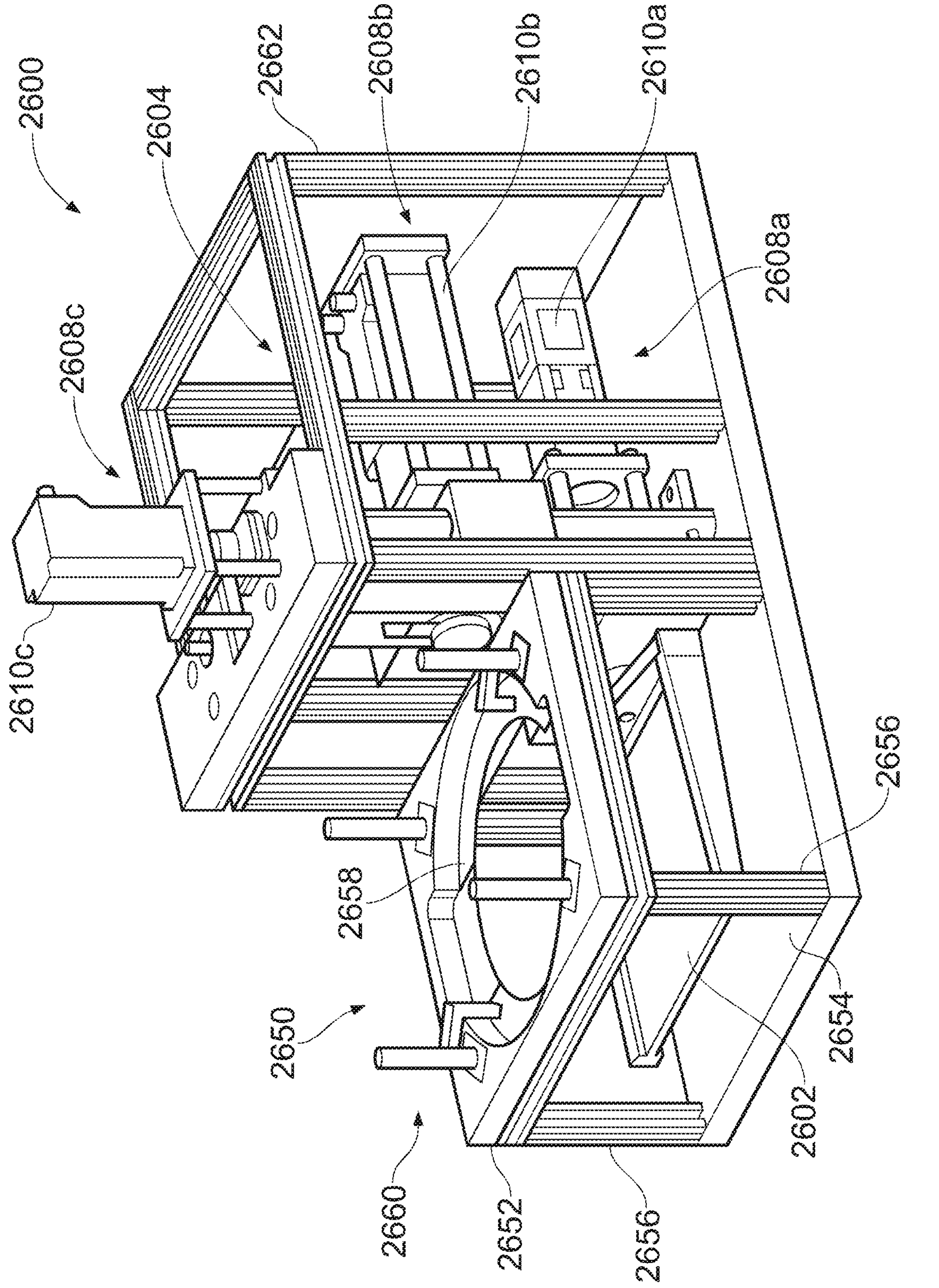
FIG. 35 illustrates a detailed perspective view of the apparatus of FIGS. 34(*a*) and (*b*)
Figure 36A:
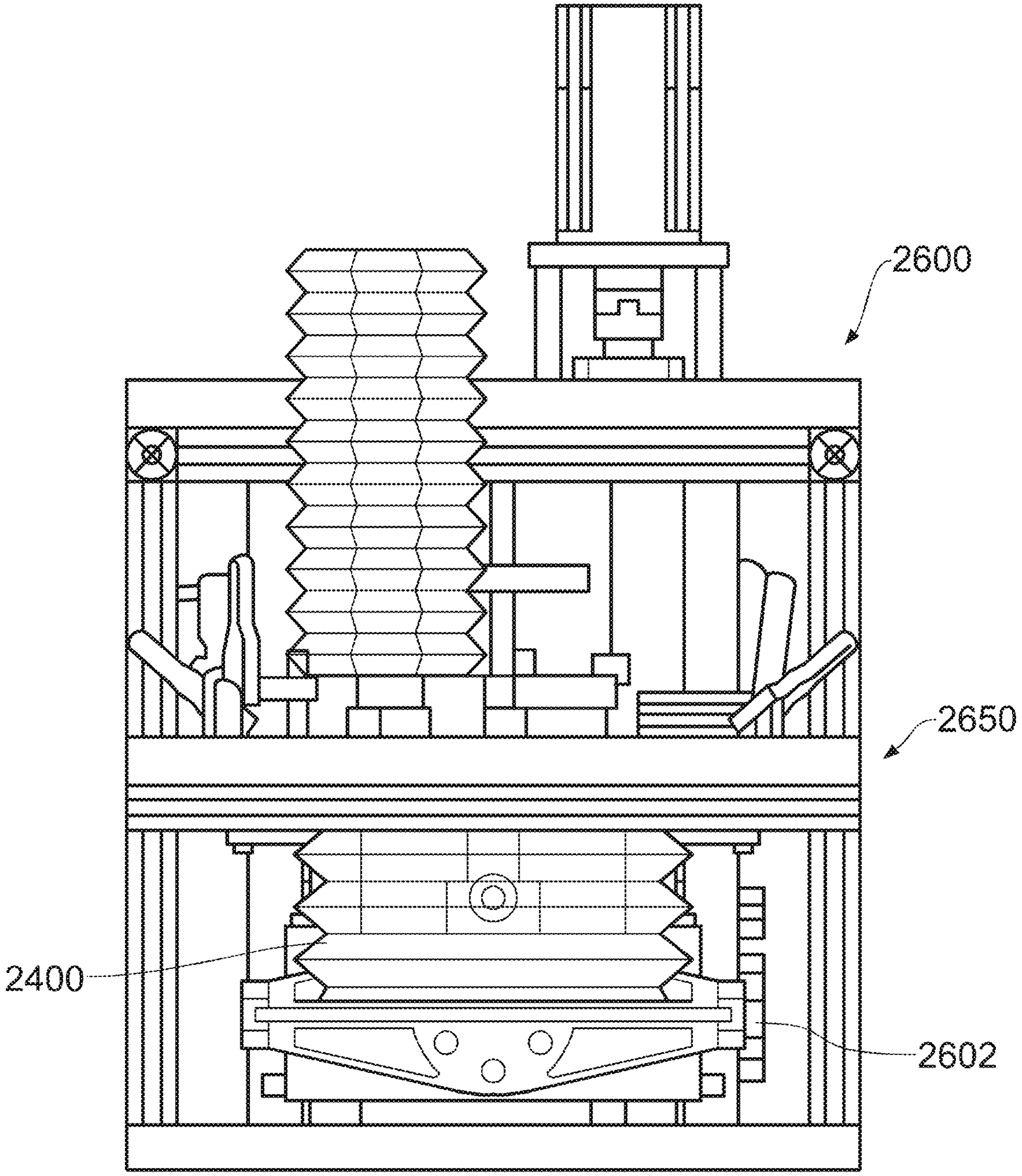
FIG. 36 illustrates (a) a front view, (b) a front perspective view, (c) a rear perspective view, (d) a side view and (e) a top view of the apparatus of FIG. 35 having the platform and containers of FIGS. 33(*a*) to 33(*d*) attached thereto.
Figure 36B:
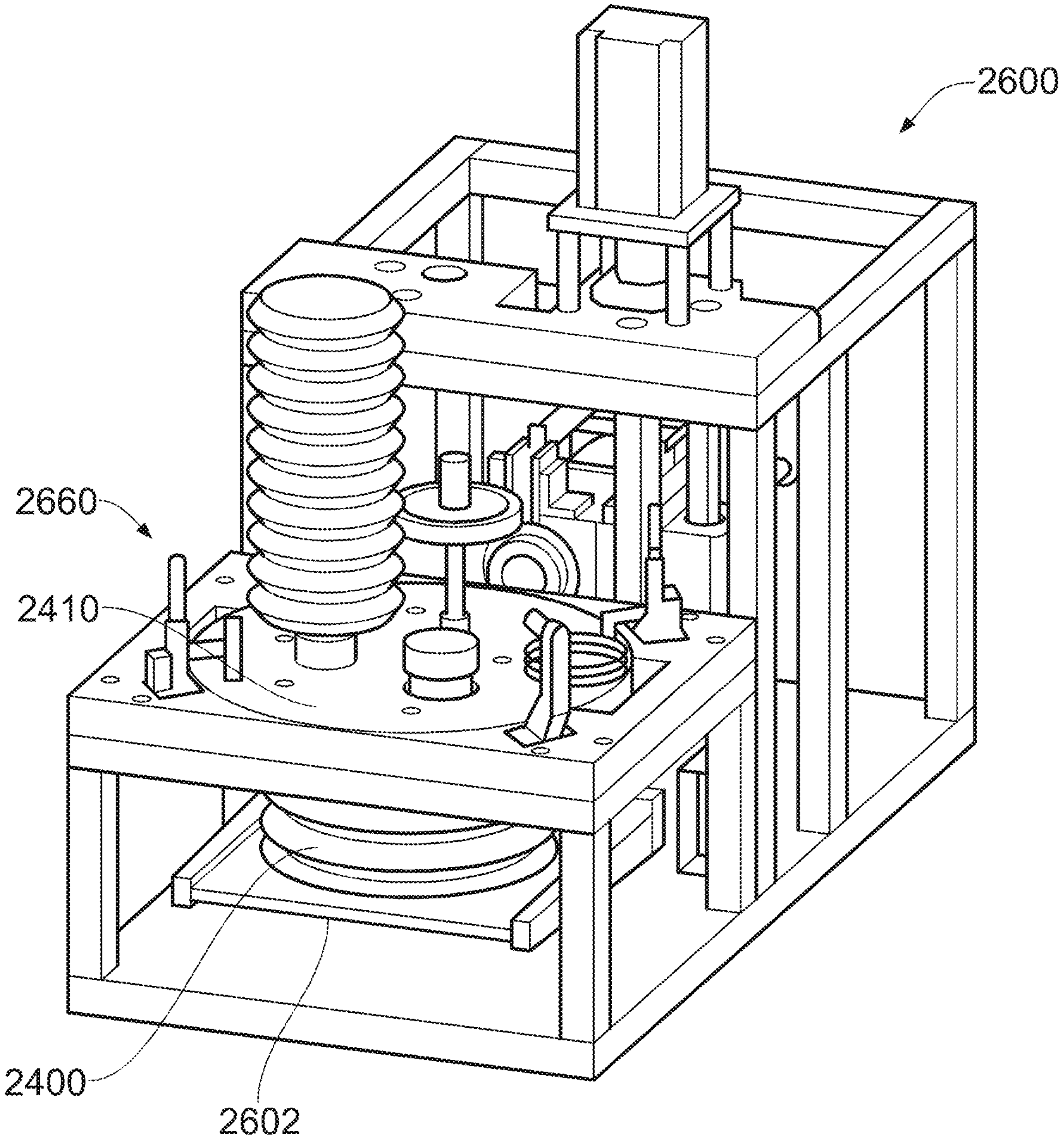
Figure 36C:
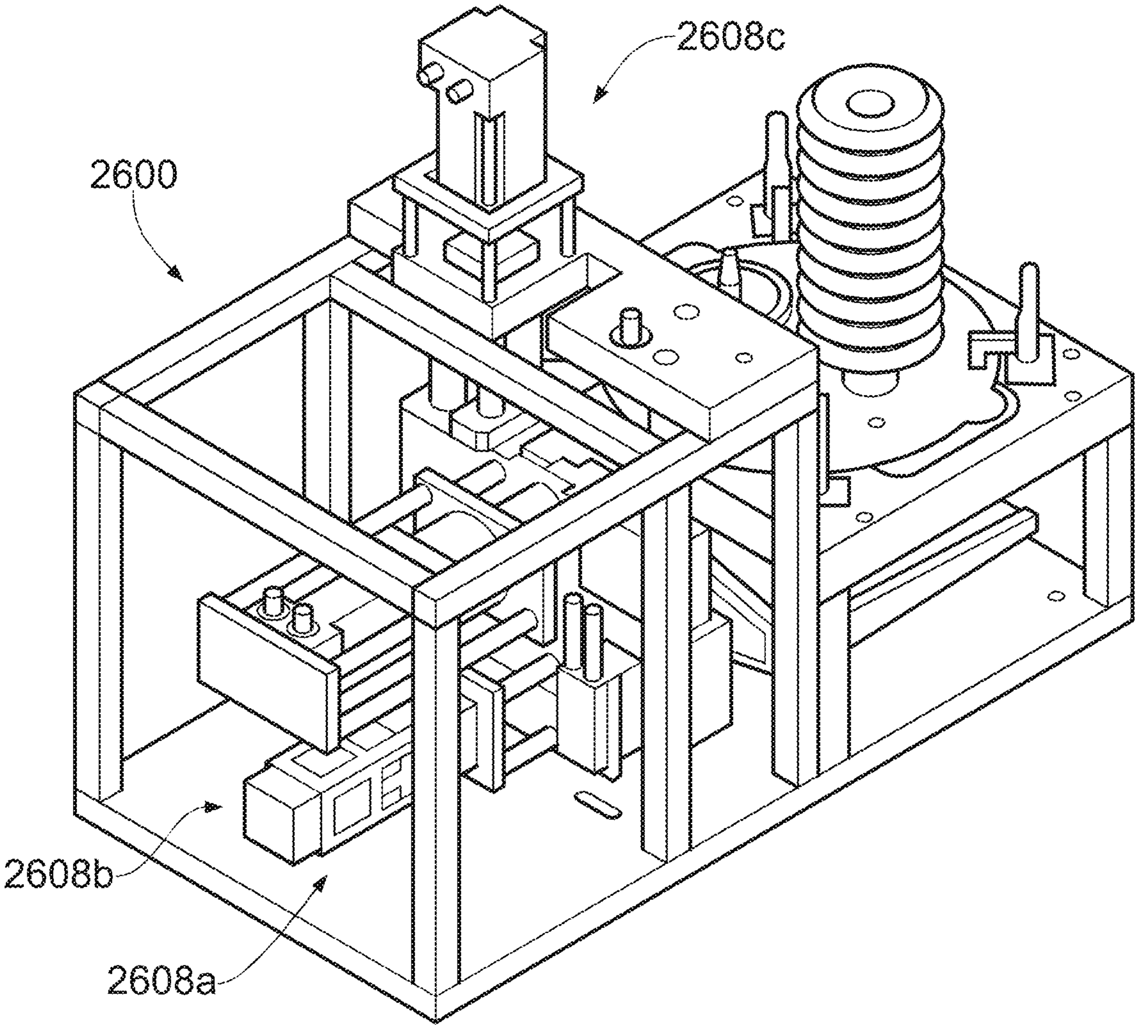
Figure 36D:
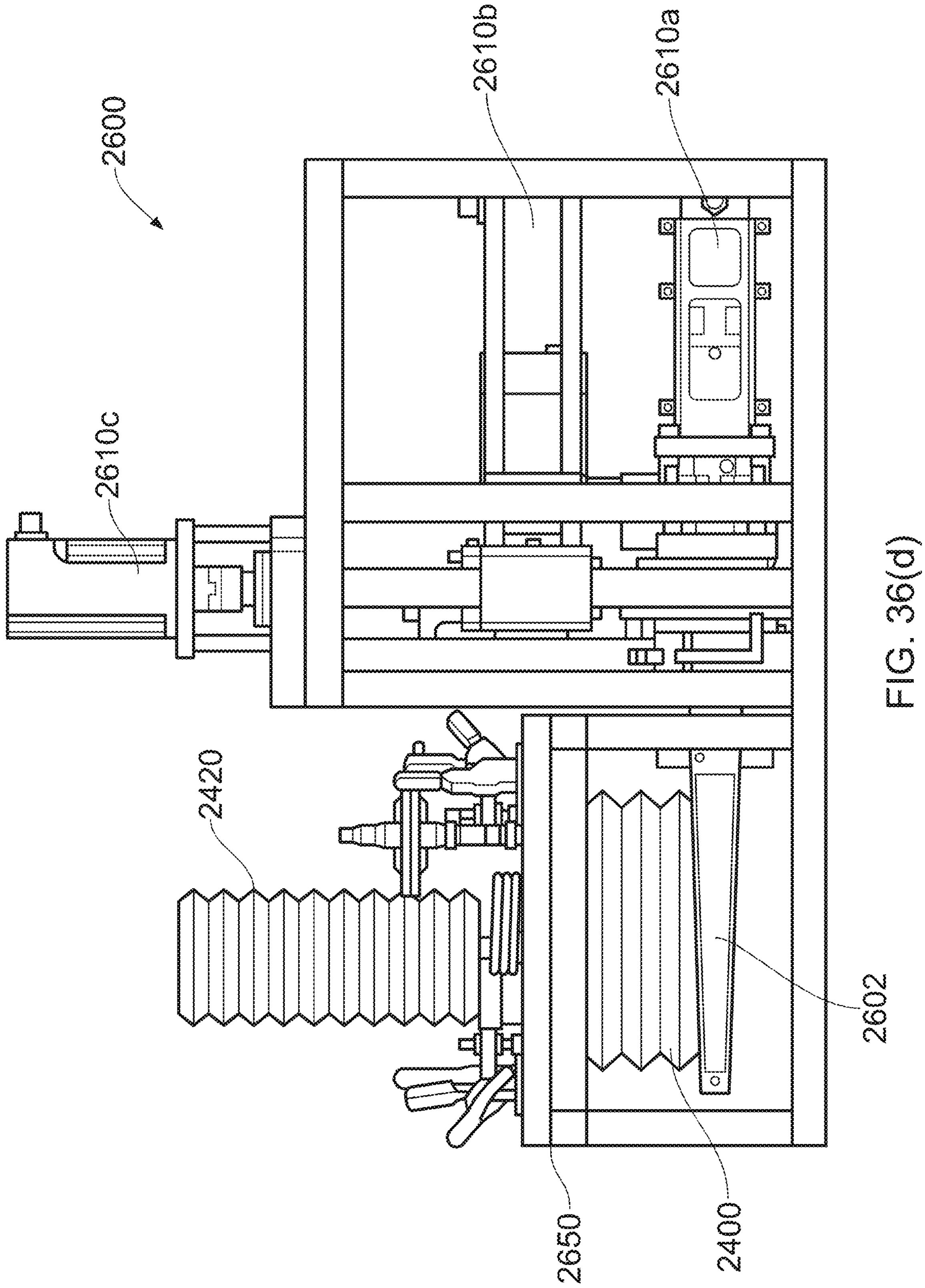
Figure 36E:
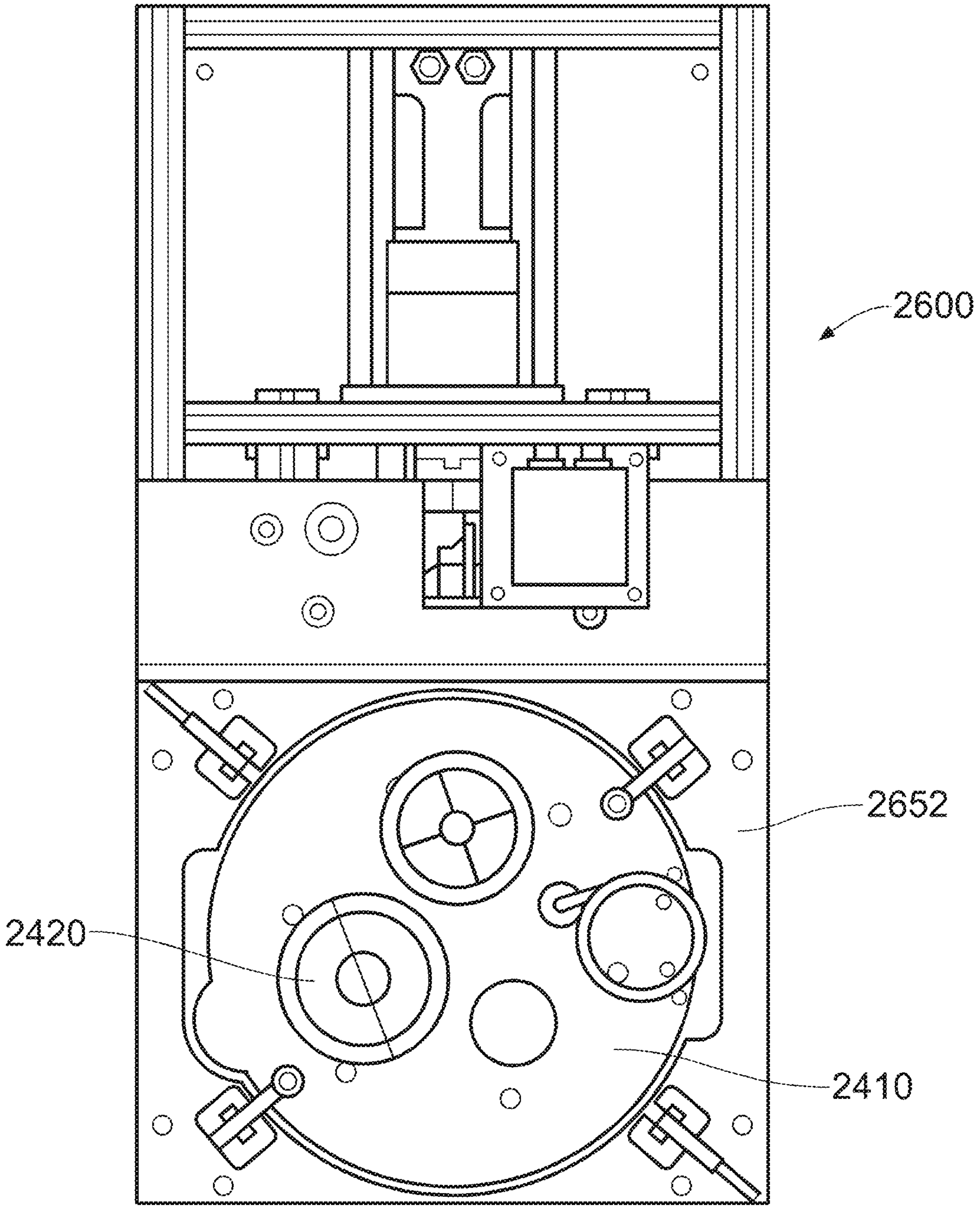

FIGS. 35 and 36(*a*) to 36(*d*) illustrate another apparatus 2600 of the disclosure, which operates based upon the same principle as noted in the apparatus 2500 above of FIGS. 34(*a*) to 34(*d*).

FIG. 35 illustrates the apparatus 2600 including a moveable plate 2602 operated by the linkage 2604, motors 2608*a*, 2608*b*, 2608*c* and gearboxes 2610*a*, 2610*b*, 2610*c* as described in relation to FIGS. 34(*a*) to 34(*d*). Further explanation will not be provided for brevity. The apparatus 2600 further includes a holding element 2650. The holding element 2650 is formed of an upper plate 2652, arranged to receive a top portion of a container in use, and a lower plate 2654. The moveable plate 2602 is arranged between the upper plate 2652 and the lower plate 2654. The upper plate 2652 is connected to the lower plate 2654 by a plurality of legs 2656 extending therebetween and coupled to each plate 2652, 2654 at their ends. The upper plate 2652 generally includes a recessed surface 2658 for receiving a top portion of a container in use and as described further below. The upper plate 2652 also includes a plurality of clamps 2660 arranged to clamp a top portion of a container, in use, to the upper plate 2652.

The apparatus 2600 also includes a frame 2662 formed about the actuation mechanism, including the linkage 2604, motors 2608*a*, 2608*b*, 2608*c* and the gearboxes 2610*a*, 2610*b*, 2610*c*. Although not illustrated in this drawing for clarity, the frame 2662 also includes a plurality of panels enclosing the components of the actuation mechanism, thereby preventing user access during use. Further, the panels may prevent the ingress liquid, or other cell processing components such as media, cells, or similar, into the actuation mechanism. The frame 2662 and the panels may be regarded as forming a housing for the actuation mechanism.

FIGS. 36(*a*) to 36(*e*) illustrate the apparatus 2600, described in relation to FIG. 35, having the container 2400 and platform 2410 of FIGS. 33(*a*) to 33(*d*) attached thereto. In particular, a base section of the container 2400 is engageable with the moveable plate 2602. In this particular embodiment, the base section of the container 2400 is allowed to engage, and disengage, freely with the moveable plate 2602, but in other examples the base section of the container 2400 may be fixedly coupled or attached, such as through adherence, fastening means or the like, to the moveable plate 2602. Further, the platform 2410, which is coupled to the top section of the container 2400, is received within the recessed surface 2658 (see FIG. 35) and clamped thereto by a plurality of clamps 2660. As such, the container 2400 is positioned between the moveable plate 2602 and the holding element 2650, so as to allow for compression, decompression, or other movement, of the container 2400 during use.

During use, the respective motors 2608*a*, 2608*b*, 2608*c* are actuated so as to cause desired movement of the container 2400, in a manner analogous to that described in relation to FIGS. 34(*a*) to 34(*d*). In particular, the first motor 2608*a* controls rotational movement of the base of the container 2400, about an axis formed within the plane of the moveable plate 2602, the second motor 2608*b* controls rapid compression/decompression of the container 2400, specifically by axially translating the base of the container 2400 toward, or away from, the holding element 2650, and the third motor 2608*c* controls slow compression/decompression of the container 2400, specifically by axially translating the base of the container 2400 toward or away from, the holding element 2650. The first motor 2608*a* thus may be useful for imparting a swirling or rocking motion to the base of the container 2400. The second motor 2608*b* thus may be useful for imparting a compression mixing motion, i.e., rapid compression followed by rapid decompression, to the container 2400. The third motor 2608*c* thus may be useful for imparting a breathing motion, for example, by causing fluid, such as air, media or the like, to be expelled from the container 2400 and into the secondary container 2420, described in further detail in relation to FIGS. 33(*a*) to 33(*d*). As such, distinct motors may be provided for the distinct, or indeed composite during use, motions imparted to the container 2400.

Figure 37:
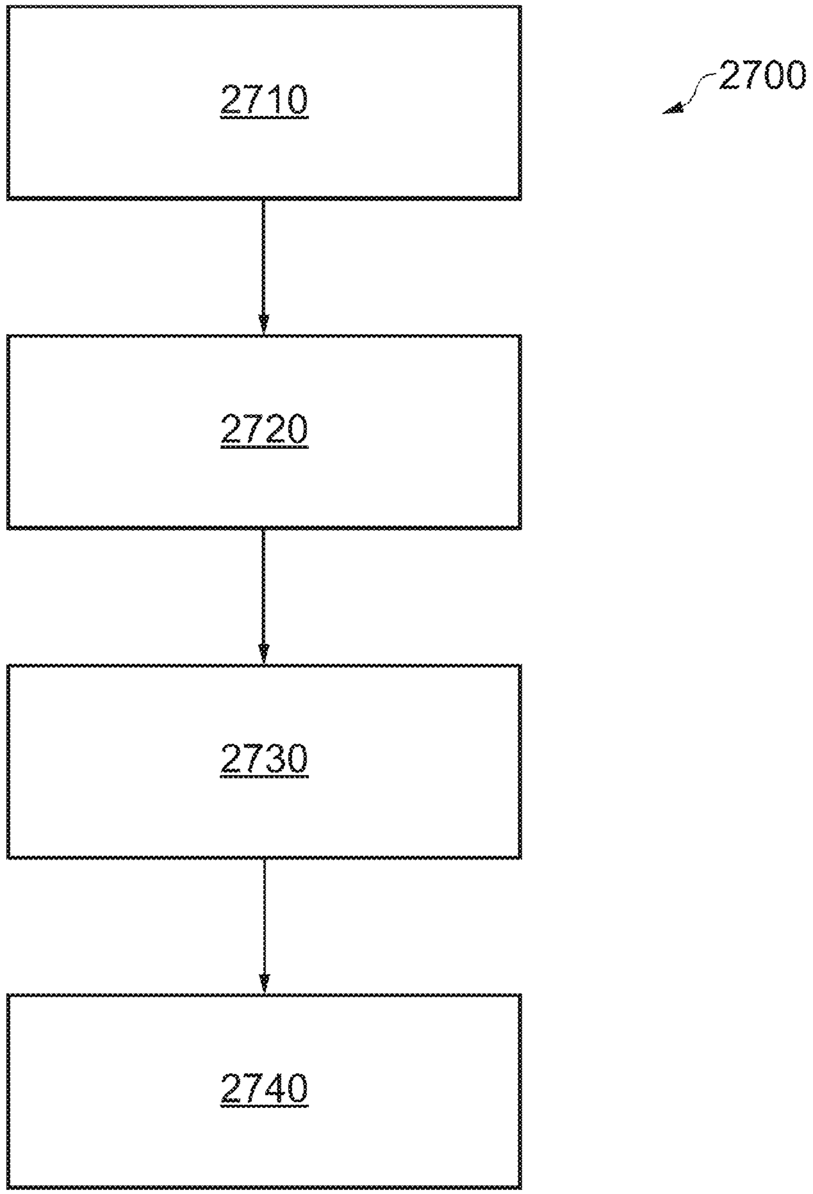
FIG. 37 illustrates a method according to the disclosure.

In some examples herein, there may be a method 2700, illustrated by FIG. 37, for cell processing. The method 2700 may include the step of providing 2710 a compressible container including a population of cells in a liquid medium. The method 2700 may include the step of statically processing 2720 the population of cells in the liquid medium within the compressible container. The method 2700 may include the step of dynamically processing 2730 the population of cells in the liquid medium within the compressible container.

The step of statically processing 2720 the population of cells in the liquid medium may comprise not subjecting the population of cells to any movement or force. That is, there may be a static phase of cell processing.

The step of dynamically processing 2730 the population of cells in the liquid medium may include agitating the population of cells in the liquid medium. The step of agitating the population of cells in the liquid medium may include imparting a wave motion to the population of cells and the liquid medium, imparting a swirling motion to the population of cells and the liquid medium, compressing the compressible container, or a combination thereof. The step of compressing the compressible container may include compressing the compressible container along a longitudinal axis that is perpendicular to a top section and a base section of the container.

There may be provided a separate step, or a step in combination with any other step, of compressing 2740 the compressible container including the cell population in the liquid medium.

Further embodiments and examples are provided below with reference to FIGS. 38 to 42.

EXAMPLES

The disclosure will now be described with reference to the following non-limiting examples, which demonstrate various embodiments of the disclosure. It is noted that the container 2400 and the platform 2410 of FIGS. 33(*a*) to 33(*d*) was utilized in combination with the apparatus 1600 of FIGS. 18(*a*) to 18(*d*) for the below examples:

Materials

The following materials were utilized:

CD3+ T cells, healthy donor 1 (HD1) (Isolated from leukopak, Access Biologicals LLC)

X-VIVO 15 (LZBE02-053Q, Lonza)

5% Normal human AB serum (H4522, Sigma)

rhIL-2 (100 units·mL$^{-1}$) (202-IL-050, R&D Systems)

Activation: CTS Dynabeads (3:1 bead-cell ratio) (40203D, ThermoFisher)

Transduction: GFP Lentiviral vector (MOI:1) (0010VCT, Takarabio)

Methods

The following methods were utilized:

$$\text{Seeding density (Day 0)} = 1\times10^{6}\ \text{cells.mL}^{-1}$$

$$\text{Seeding volume (Day 0)} = 50\ \text{mL}$$

Feeding: Fed batch, volume doubled from set timepoint at end of static period (Day 3). Not dictated by cell density from sampling. Media volume additions contain fresh IL2 cytokine (100 units·mL).

Controls: FEP static culture bags (CellGenix VueLife) of increasing volume (see below) to replicate manual process for both static and early expansion phase with the same seeding density and feeding strategy (without agitation).

Viable cell density and fold expansion: Cellometer Auto 2000, Nexcelom

Figure 38:
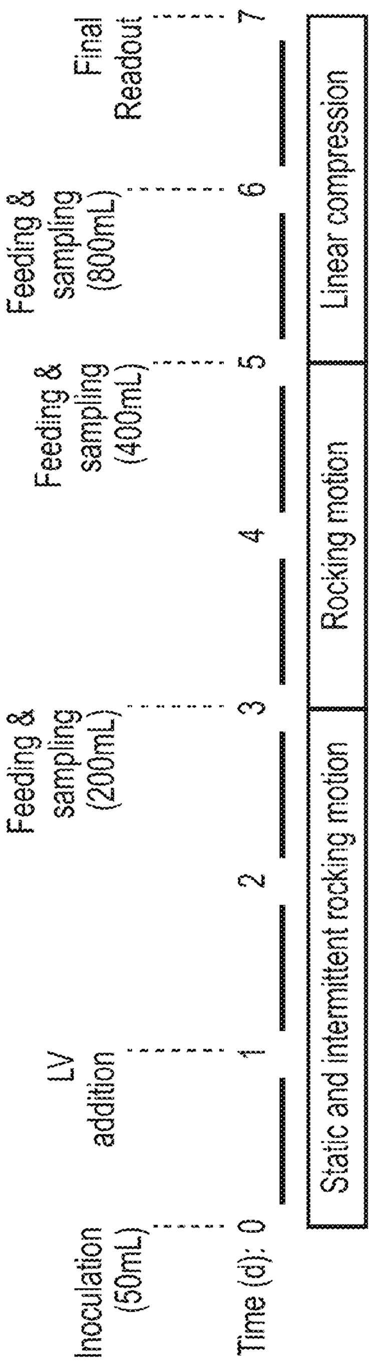
FIG. 38 illustrates an exemplary testing run timeline.

Testing Run Timeline:

The general testing run timeline is shown in FIG. 38. In particular, inoculation is provided at Day 0. Lentiviral vector is added at Day 1. From Day 0 to Day 3, static and/or intermittent rocking motion is imparted to the container by the apparatus. Feeding, i.e., the supply of nutrients in media, is undertaken on Day 3, and samples also taken on Day 3 for testing. From Day 3 to Day 5, a rocking motion is imparted to the container by the apparatus. Further feeding is undertaken on Day 5, and samples also taken on Day 5 for testing.

Finally, from Day 5 to Day 7, linear compression is imparted to the container by the apparatus. Further feeding is undertaken on Day 6 and samples also taken on Day 6 for testing. A final readout, such as for cell viability and the number of total viable cells, is taken at, or following, Day 7. Whilst this testing run provides a general process for culturing cells using the apparatus, further specific examples are noted below.

Example 1

For the Primary T-cell Run 1 (FIGS. 39 and 41), the cells and culture media were placed in a bioreactor, specifically a container 2400 illustrated in FIGS. 33(*a*) to 33(*d*). The cell culture process is substantially as described above in the testing run timeline. In this particular example, inoculation was provided at Day 0 at a volume of 50 mL utilizing the above materials, followed by lentiviral vector addition. A sample was taken on Day 3, and a feeding volume of 150 mL provided to the container. Further samples were taken on Days 4, 5 and 6. Further feeding, at a feeding volume of 100 mL, was provided on Day 6. Further feeding was provided on Days 7, 8, 9, and 10 at feed volumes of 100 mL, 400 mL, 100 mL and 50 mL, respectively. Samples were taken on Days 7, 8, 9, 10 and 11.

Additionally, the following process, or specifically the following agitation, steps were used:

1. Days 0 to 3 and Days 4 to 5: none (i.e., static culture)
2. Days 3 to 4: rocking motion A (60 rpm, displacement amplitude of 20 mm)
3. Days 5 to 6: rocking motion B (20 rpm, displacement amplitude of 10 mm)
4. Days 6 to 11: linear compression (60 cpm, displacement amplitude of 20 mm)

Figure 39:
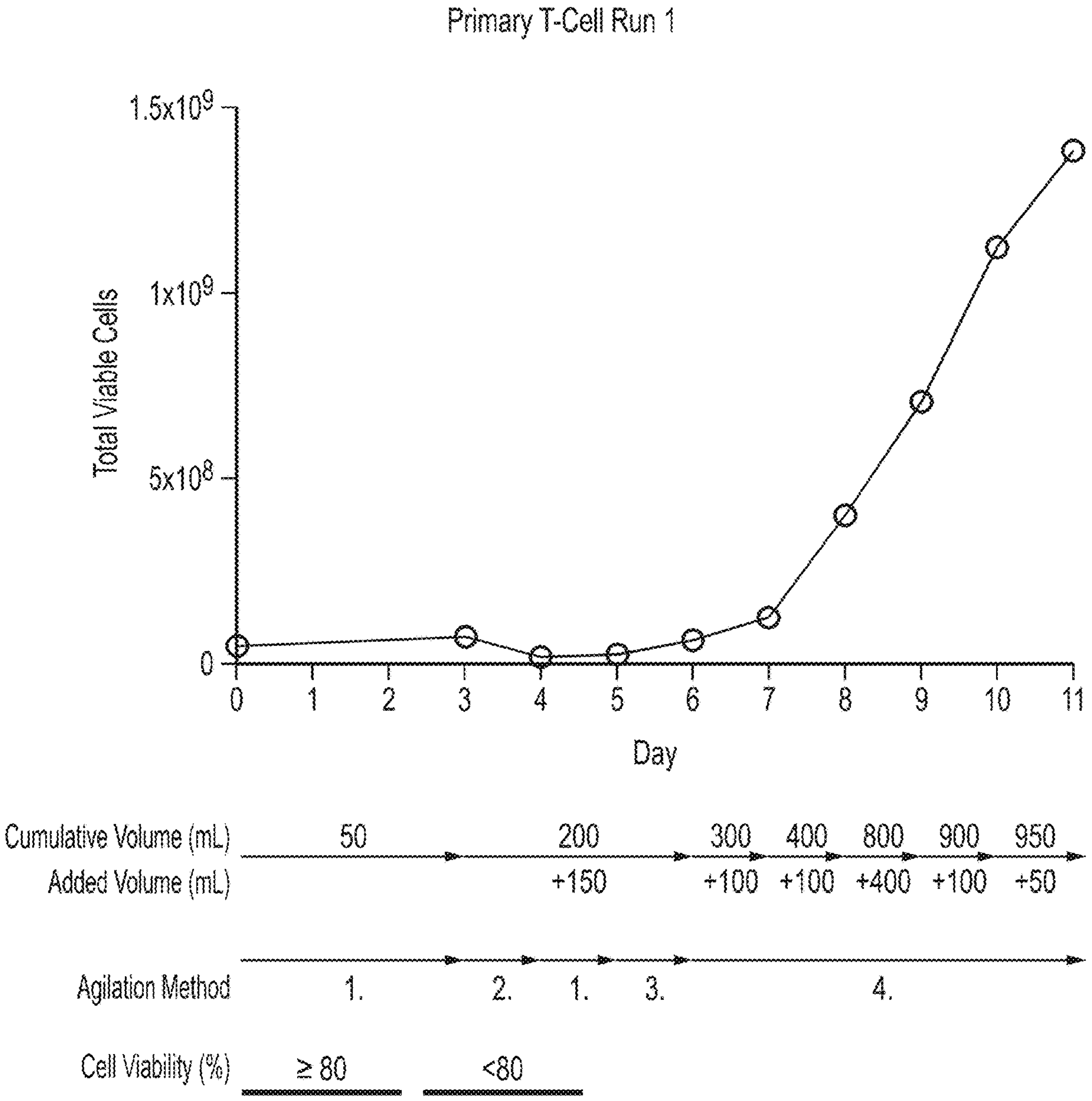
FIG. 39 illustrates the results of an exemplary primary T-cell run timeline using the apparatus/system according to the disclosure.
Figure 41:
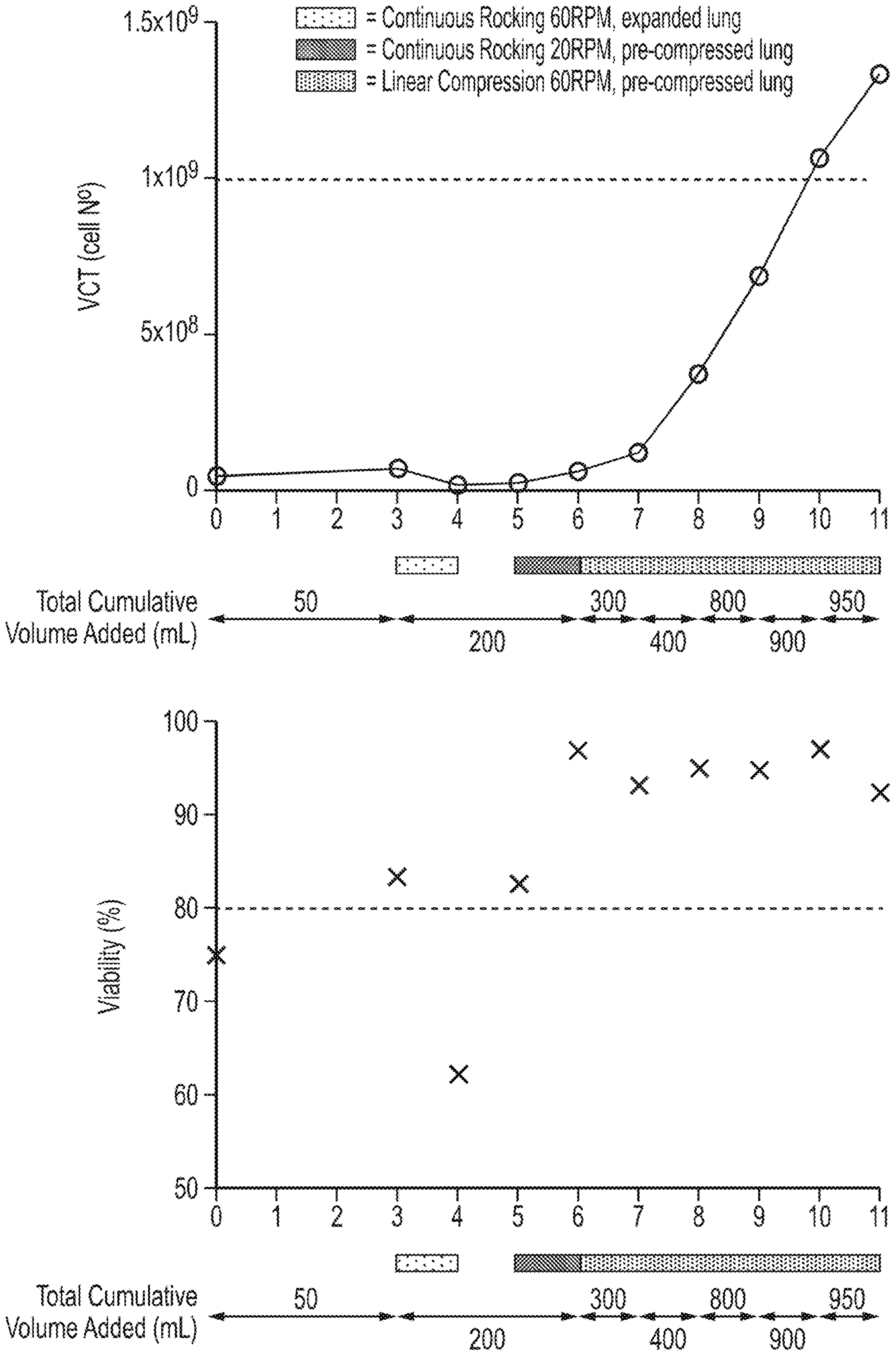
FIG. 41 illustrates the further results from the exemplary primary T-cell run timeline illustrated in FIG. 39.

The relevant agitation steps (either 1, 2, 3 or 4) are indicated in FIGS. 39 and 41 at the appropriate time intervals. The total viable cells are illustrated in FIGS. 39 and 41 for this particular agitation regime, whilst FIG. 41 also illustrates the cell viability.

The key outcomes of the primary T-cell run 1 were that:

One vessel can used for all volumes: no manual transfers were required

Rocking motion A (Day 3 to 4): cell death was observed

Cell yield after 4 days of compression mixing was $>1\times10^9$

Final viability was within release criteria (≥80%)

Example 2

For the Primary T-cell Run 2 (FIGS. 40 and 42), the cells and culture media were placed in a bioreactor, specifically a container 2400 illustrated in FIGS. 33(*a*) to 33(*d*). The cell culture process is substantially as described above in the testing run timeline. In this particular example, inoculation was provided at Day 0 at a volume of 50 mL, followed by lentiviral vector addition. A sample was taken on Day 3, and a feeding volume of 150 mL provided to the container. Further samples were taken on Days 4 and 5. Further feeding, at a feeding volume of 200 mL, was provided on Day 5. Further feeding was provided, and samples taken, on Day 6, at a feed volume of 400 mL. Samples were subsequently taken on Days 7 and 8.

Additionally, the following process, or specifically the following agitation, steps were used:

1. Days 0 to 3: none (i.e., static culture)
2. Days 3 to 4: rocking motion C (20 rpm, displacement amplitude of 20 mm)
3. Days 4 to 5: rocking motion B (20 rpm, displacement amplitude of 10 mm)
4. Days 6 to 8: linear compression (60 cpm, displacement amplitude of 20 mm)

Figure 40:
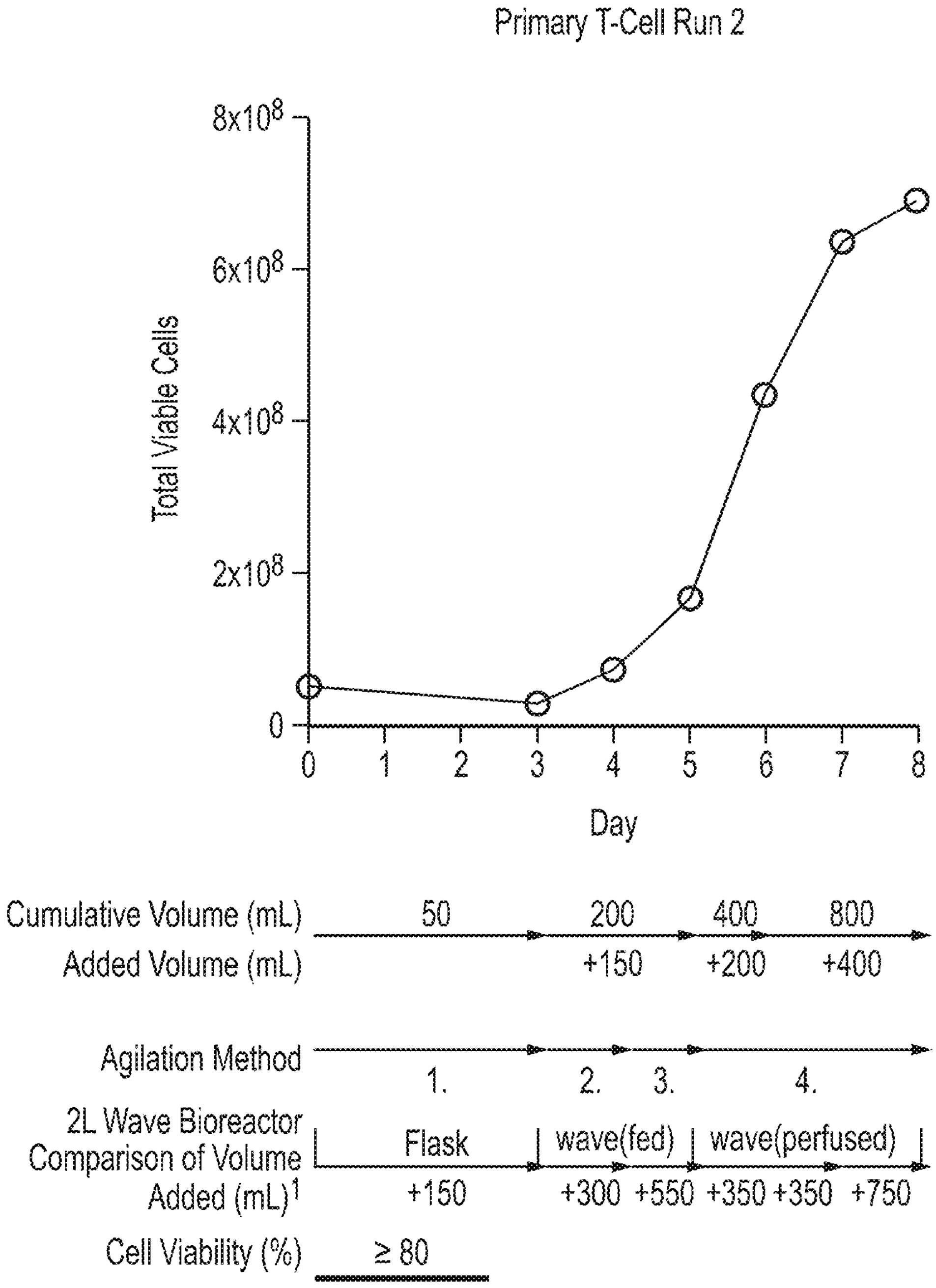
FIG. 40 illustrates the results of another exemplary primary T-cell run timeline using the apparatus/system according to the disclosure.
Figure 42:
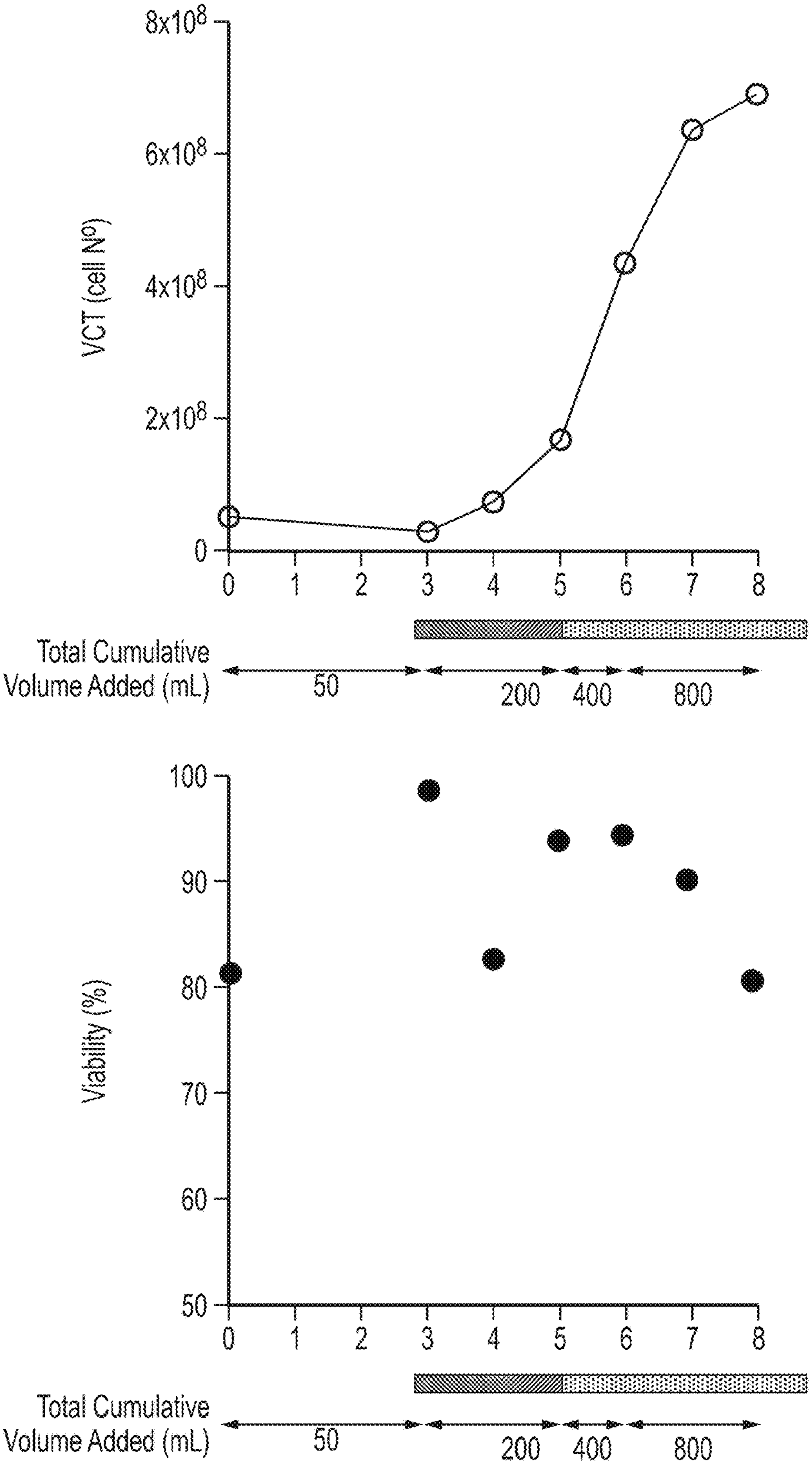
FIG. 42 illustrates the further results from exemplary primary T-cell run timeline illustrated in FIG. 40.

The relevant agitation steps (either 1, 2, 3 or 4) are indicated in FIGS. 40 and 42 at the appropriate time intervals. The total viable cells are illustrated in FIGS. 40 and 42 for this particular agitation regime, whilst FIG. 42 also illustrates the cell viability.

The key outcomes of the primary T-cell run 2 were that:

One vessel can used for all volumes: no manual transfers were required

Rocking motion C (Day 3 to 4): cell death was observed

Cell yield after 5 days of agitated mixing was $>6\times10^6$

Viability within release criteria throughout (≥80%)

As illustrated in FIG. 40, ~60% less culture medium used over 8 days in the present container compared to a standard WAVE perfusion protocol (estimated based on a standard protocol for perfusion culture of T lymphocytes in the WAVE Bioreactor System 2/10, GE Healthcare Life Sciences (Application note 28-9650-52 AC)).

It will be appreciated by persons skilled in the art that the above embodiment(s) have been described by way of example only and not in any limitative sense, and that various alterations and modifications are possible without departing from the scope of the disclosure as defined by the appended claims. Various modifications to the detailed designs as described above are possible, for example, variations may exist in shape, size, arrangement, assembly or the like.

In particular, any of the discussed actuation mechanisms may be utilized in any embodiment of the apparatuses, systems or methods discussed herein. Furthermore, any of the discussed holding elements may be utilized in any embodiment of the apparatuses, systems or methods discussed herein. Yet further, any of the discussed containers, platforms or other like cell processing components may be utilized in any embodiment of the apparatuses, systems of methods discussed herein.

Whilst the above examples also illustrate exemplary uses of the disclosed apparatus and system, the person skilled in the art would appreciate that it is equally applicable to other cell types, media types, transduction and activation reagents, and the like. Equally, the person skilled in the art would appreciate that other mixing/agitation regimes are equally contemplated as part of the disclosure, for example, the rate, the time periods, the amplitudes or the like of the rocking, swirling and/or compression regimes discussed herein.

The invention claimed is:

1. An apparatus for use in performing one or more unit operations in cell processing comprising:

a holding element arranged to receive a top section of a container within a first plane;

a moveable plate, spaced apart from the holding element, arranged to operably engage a base section of a container, the moveable plate defining a second plane substantially parallel to the first plane; and an actuation mechanism operably coupled to the moveable plate to rotate the moveable plate about at least one axis within the second plane, thereby reducing a distance between at least a portion of the second plane and the first plane, the actuation mechanism configured to move the moveable plate along a longitudinal axis, the longitudinal axis substantially perpendicular to the first plane and the second plane, to reduce a distance between the second plane and the first plane.

2. The apparatus according to claim 1, wherein the actuation mechanism is arranged to rotate the moveable plate about an axis within the second plane.

3. The apparatus according to claim 1, wherein the actuation mechanism is arranged to rotate the moveable plate about a plurality of axes within the second plane.

4. The apparatus according to claim 1, wherein the actuation mechanism is arranged to rotate the moveable plate between 0 degrees and 90 degrees about the at least one axis.

5. The apparatus according to claim 1, wherein the longitudinal axis intersects the second plane at an origin, wherein the actuation mechanism is arranged to pivot the moveable plate about the origin.

6. The apparatus according to claim 5, wherein the origin is centrally located within the second plane.

7. The apparatus according to claim 5, wherein the moveable plate is pivotable about the origin such that each point within the second plane, excluding the origin, forms an angle with respect to the longitudinal axis between 0 and 180 degrees, excluding 90 degrees.

8. The apparatus according to claim 1, wherein the holding element comprises: a platform operably engageable with a top section of a container, a clamping mechanism operably engageable with a top section of a container, or a sealing plate operably engageable with a top section of a container.

9. The apparatus according to claim 1, wherein the actuation mechanism comprises a base plate spaced apart from, and substantially parallel to, the moveable plate, the base plate operably coupled to the moveable plate.

10. The apparatus according to claim 9, wherein the base plate comprises at least one actuator, the at least one actuator operably coupled to, or operably engageable with, the moveable plate.

11. The apparatus according to claim 9, wherein the base plate comprises at least one rail, the at least one rail upstanding from the base plate substantially perpendicularly to the base plate, the moveable plate slidably coupled to the at least one rail, and wherein at least one actuator is arranged to slide at least a portion of the moveable plate along the at least one rail.

12. The apparatus according to any claim 9, wherein the base plate comprises a first linkage operably coupled to the moveable plate, the first linkage drivable by a first motor.

13. The apparatus according to claim 12, wherein the base plate further comprises a second linkage operably coupled to the moveable plate, the second linkage driven by a second motor.

14. The apparatus according to claim 13, wherein the first linkage and the second linkage are operably coupled at opposing edges of the moveable plate.

15. The apparatus according to claim 13, wherein the base plate further comprises a third linkage operably coupled to the moveable plate, the third linkage driven by a third motor.

16. The apparatus according to claim 15, wherein the first linkage, the second linkage and the third linkage are operably coupled to the moveable plate in a triangular arrangement.

17. The apparatus according to claim 1, wherein the actuation mechanism comprises a first motor, operably coupled to the moveable plate, and configured to rotate the moveable plate about the at least one axis within the second plane.

18. The apparatus according to claim 17, wherein the actuation mechanism further comprises a second motor, operably coupled to the moveable plate, and configured to move the moveable plate along the longitudinal axis to reduce the distance between at least the portion of the second plane and the first plane.

19. The apparatus according to claim 18, wherein the actuation mechanism further comprises a third motor, operably coupled to the moveable plate, and configured to move the moveable plate along the longitudinal axis, to reduce a distance between at least a portion of the second plane and the first plane.

20. The apparatus according to claim 19, wherein the actuation mechanism further comprises a linkage, the linkage comprising:

a crank housing, comprising a rotatable crank, slidable along a first longitudinal rail, extending substantially parallel to the longitudinal axis; and a slider portion, operably coupled to the moveable plate, slidable along a second longitudinal rail, extending substantially parallel to the first longitudinal rail, the slider portion operably coupled to the rotatable crank by a connecting rod, wherein the second motor is operably coupled to rotate the rotatable crank and move the slider portion along the second longitudinal rail, and wherein the third motor is operably coupled to the crank housing so as to move the crank housing along the first longitudinal rail.

21. The apparatus according to claim 20, wherein the third motor comprises a ball screw motor or a lead screw motor, operably coupled to a corresponding screw threaded portion of the crank housing, wherein the crank housing is moveable along the first longitudinal rail.

22. The apparatus according to claim 20, further comprising a controller communicatively coupled to the actuation mechanism.

23. The apparatus according to claim 22, further comprising one or more positioning sensors, at least one positioning senor communicatively coupled to the controller, wherein the controller configured to generate a signal to the actuation mechanism based upon a signal received from the at least one positioning sensor.

24. A system for use in performing one or more unit operations in cell processing comprising:

an apparatus comprising:

a holding element arranged to receive a top section of a container within a first plane;

a moveable plate, spaced apart from the holding element, arranged to operably engage a base section of a container, the moveable plate defining a second plane substantially parallel to the first plane; and an actuation mechanism operably coupled to the moveable plate to rotate the moveable plate about at least one axis within the second plane, thereby reducing a distance between at least a portion of the second plane and the first plane, the actuation mechanism configured to move the moveable plate along a longitudinal axis, the longitudinal axis substantially perpendicular to the first plane and the second plane, to reduce a distance between the second plane and the first plane; and a container having a base section, a top section in parallel to the base section, and a compressible wall element extending substantially perpendicularly therebetween, wherein the container is at least partially disposed between the holding element and the moveable plate, the actuation mechanism arranged to move the moveable plate such that at least a portion of the compressible wall element is at least partially compressed along a longitudinal axis perpendicular to the first plane and the second plane.

25. The system according to claim 24, wherein the base section of the container is fixedly attached to the moveable plate.

26. A method of processing cells, the method comprising:

providing a cell processing medium in a container, the container having a base section, a top section in parallel to the base section, and a compressible wall element extending substantially perpendicularly therebetween;

holding the top section of the container within a first plane using a holding element of an apparatus, the apparatus comprising:

the holding element arranged to receive the top section of the container within the first plane;

a moveable plate, spaced apart from the holding element, arranged to operably engage the base section of the container, the moveable plate defining a second plane substantially parallel to the first plane; and an actuation mechanism operably coupled to the moveable plate to rotate the moveable plate about at least one axis within the second plane, thereby reducing a distance between at least a portion of the second plane and the first plane, the actuation mechanism configured to move the moveable plate along a longitudinal axis, the longitudinal axis substantially perpendicular to the first plane and the second plane, to reduce a distance between the second plane and the first plane;

engaging the base section of the container with the moveable plate defining the second plane substantially parallel to, and spaced apart from, the first plane; and rotating the base section of the container about at least one axis within the second plane with the actuation mechanism, to cause turbulence of the cell processing medium within the container.

27. The method according to claim 26, wherein the step of rotating the base section of the container comprises rotating the base section of the container about an axis within the second plane.

28. The method according to claim 26, wherein the longitudinal axis intersects the second plane at an origin, wherein the step of rotating the base section of the container comprises pivoting the base section of the container about the origin.

29. The method according to claim 28, wherein the origin is centrally located within the second plane.

* * * * *